(12) United States Patent
O'Shea et al.

(10) Patent No.: US 12,365,878 B2
(45) Date of Patent: Jul. 22, 2025

(54) ONCOLYTIC ADENOVIRUS WITH ENHANCED REPLICATION PROPERTIES COMPRISING MODIFICATIONS IN E1A, E3, AND E4

(71) Applicant: Salk Institute for Biological Studies, La Jolla, CA (US)

(72) Inventors: Clodagh O'Shea, San Diego, CA (US); Michael Lyman, La Jolla, CA (US); William Partlo, La Jolla, CA (US); Shigeki Miyake-Stoner, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 1151 days.

(21) Appl. No.: 17/067,496

(22) Filed: Oct. 9, 2020

(65) Prior Publication Data
US 2021/0024587 A1 Jan. 28, 2021

Related U.S. Application Data

(63) Continuation of application No. PCT/US2019/026626, filed on Apr. 9, 2019.

(60) Provisional application No. 62/655,009, filed on Apr. 9, 2018.

(51) Int. Cl.
*A61K 35/761* (2015.01)
*A61P 35/00* (2006.01)
*C07K 14/005* (2006.01)
*C12N 7/00* (2006.01)

(52) U.S. Cl.
CPC ............. *C12N 7/00* (2013.01); *A61K 35/761* (2013.01); *A61P 35/00* (2018.01); *C07K 14/005* (2013.01); *C12N 2710/10321* (2013.01); *C12N 2710/10322* (2013.01); *C12N 2710/10332* (2013.01); *C12N 2710/10371* (2013.01)

(58) Field of Classification Search
CPC ........ A61K 35/761; C12N 2710/10011; C12N 2710/10032; C12N 2710/10311; C12N 2710/10332
See application file for complete search history.

(56) References Cited

U.S. PATENT DOCUMENTS

| | | |
|---|---|---|
| 5,543,328 A | 8/1996 | McClelland et al. |
| 5,559,099 A | 9/1996 | Wickham et al. |
| 5,670,488 A | 9/1997 | Gregory et al. |
| 5,677,178 A | 10/1997 | McCormick |
| 5,731,190 A | 3/1998 | Wickham et al. |
| 5,801,029 A | 9/1998 | McCormick |
| 5,846,782 A | 12/1998 | Wickham et al. |
| 5,846,945 A | 12/1998 | McCormick |
| 5,856,181 A | 1/1999 | McCormick |
| 5,922,315 A | 7/1999 | Roy |
| 5,945,335 A | 8/1999 | Colosi |
| 5,962,311 A | 10/1999 | Wickham et al. |
| 5,965,541 A | 10/1999 | Wickham et al. |
| 5,972,706 A | 10/1999 | McCormick |
| 6,020,172 A | 2/2000 | Both |
| 6,069,134 A | 5/2000 | Roth et al. |
| 6,127,525 A | 10/2000 | Crystal et al. |
| 6,133,243 A | 10/2000 | Kirn |
| 6,153,435 A | 11/2000 | Crystal et al. |
| 6,296,845 B1 | 10/2001 | Sampson et al. |
| 6,329,190 B1 | 12/2001 | Wickham et al. |
| 6,410,010 B1 | 6/2002 | Zhang et al. |
| 6,455,314 B1 | 9/2002 | Wickham et al. |
| 6,465,253 B1 | 10/2002 | Wickham et al. |
| 6,475,480 B1 | 11/2002 | Mehtali et al. |
| 6,506,379 B1 | 1/2003 | Clackson et al. |
| 6,506,602 B1 | 1/2003 | Stemmer |
| 6,569,677 B1 | 5/2003 | Legrand et al. |
| 6,596,268 B1 | 7/2003 | Coffey et al. |
| 6,635,466 B2 | 10/2003 | Davidson et al. |
| 6,635,476 B1 | 10/2003 | Murphy |
| 6,649,157 B2 | 11/2003 | Coffey et al. |
| 6,737,234 B1 | 5/2004 | Freimuth |
| 6,740,525 B2 | 5/2004 | Roelvink et al. |
| 6,797,702 B1 | 9/2004 | Roth et al. |
| 6,811,774 B2 | 11/2004 | Haddada et al. |
| 6,824,771 B1 | 11/2004 | Curiel et al. |

(Continued)

FOREIGN PATENT DOCUMENTS

| | | |
|---|---|---|
| CN | 1330715 A | 1/2002 |
| CN | 1380420 A | 11/2002 |

(Continued)

OTHER PUBLICATIONS

Hibma et al., "Increased apoptosis and reduced replication efficiency of the E3 region-modified dl309 adenovirus in cancer cells," *Virus Res* 145:112-120, 2009.

(Continued)

*Primary Examiner* — Jeffrey S Parkin
(74) *Attorney, Agent, or Firm* — Klarquist Sparkman, LLP

(57) ABSTRACT

Tumor-selective recombinant adenoviruses that possess deletions or modifications in the E3 region are described. Recombinant adenoviruses that express adenovirus death protein (ADP) but have a deletion of at least three of the remaining six E3 genes exhibit enhanced virus replication. The recombinant adenoviruses further include additional modifications to allow selective replication in tumor cells and to detarget viruses from the liver. Use of the recombinant adenoviruses for cancer treatment is described.

35 Claims, 15 Drawing Sheets

Specification includes a Sequence Listing.

(56) References Cited

U.S. PATENT DOCUMENTS

| | | |
|---|---|---|
| 6,838,285 B2 | 1/2005 | Farmer et al. |
| 6,841,540 B1 | 1/2005 | Curiel et al. |
| 6,849,446 B2 | 2/2005 | Tikoo et al. |
| 6,867,022 B1 | 3/2005 | Imperiale |
| 6,869,936 B1 | 3/2005 | Vogels et al. |
| 6,878,549 B1 | 4/2005 | Vogels et al. |
| 6,905,678 B2 | 6/2005 | Havenga et al. |
| 6,911,199 B2 | 6/2005 | Vigne et al. |
| 6,911,200 B2 | 6/2005 | Yu et al. |
| 6,913,922 B1 | 7/2005 | Bout et al. |
| 6,929,946 B1 | 8/2005 | Vogels et al. |
| 6,951,755 B2 | 10/2005 | Wickham et al. |
| 6,984,635 B1 | 1/2006 | Schreiber et al. |
| 7,001,596 B1 | 2/2006 | Johnson et al. |
| 7,045,347 B2 | 5/2006 | Graham et al. |
| 7,094,398 B1 | 8/2006 | Lieber et al. |
| 7,094,399 B2 | 8/2006 | Otto |
| 7,109,179 B2 | 9/2006 | Roth et al. |
| 7,157,266 B2 | 1/2007 | Freimuth et al. |
| 7,232,899 B2 | 6/2007 | Von Seggern et al. |
| 7,235,233 B2 | 6/2007 | Havenga et al. |
| 7,247,472 B2 | 7/2007 | Wilson et al. |
| 7,252,817 B2 | 8/2007 | Coffey et al. |
| 7,252,989 B1 | 8/2007 | Zhang et al. |
| 7,256,036 B2 | 8/2007 | Legrand et al. |
| 7,291,498 B2 | 11/2007 | Roy et al. |
| 7,297,542 B2 | 11/2007 | Curiel et al. |
| 7,306,793 B2 | 12/2007 | Haddada et al. |
| 7,332,337 B2 | 2/2008 | van Es et al. |
| 7,344,711 B2 | 3/2008 | Bonastre et al. |
| 7,344,872 B2 | 3/2008 | Gao et al. |
| 7,364,727 B2 | 4/2008 | Li et al. |
| 7,410,954 B2 | 8/2008 | Davidson et al. |
| 7,456,008 B2 | 11/2008 | Lindholm et al. |
| 7,473,418 B2 | 1/2009 | Yu et al. |
| 7,482,156 B2 | 1/2009 | Arroyo et al. |
| 7,491,508 B2 | 2/2009 | Roy et al. |
| 7,510,868 B2 | 3/2009 | Harden et al. |
| 7,589,069 B1 | 9/2009 | Wold et al. |
| 7,611,868 B2 | 11/2009 | Monaci et al. |
| 7,741,099 B2 | 6/2010 | Havenga et al. |
| 7,749,493 B2 | 7/2010 | Havenga et al. |
| 7,754,201 B2 | 7/2010 | Wang et al. |
| 7,906,113 B2 | 3/2011 | Bout et al. |
| 7,943,373 B2 | 5/2011 | Fujiwara et al. |
| 7,951,585 B2 | 5/2011 | Ke |
| 7,968,333 B2 | 6/2011 | Yu et al. |
| 8,105,574 B2 | 1/2012 | Wilson et al. |
| 8,168,168 B2 | 5/2012 | Fueyo et al. |
| 8,231,880 B2 | 7/2012 | Roy et al. |
| 8,470,310 B2 | 6/2013 | Roy et al. |
| 8,524,219 B2 | 9/2013 | Roy et al. |
| 8,603,459 B2 | 12/2013 | Wilson et al. |
| 8,685,387 B2 | 4/2014 | Roy et al. |
| 8,715,642 B2 | 5/2014 | Kochanek et al. |
| 8,765,146 B2 | 7/2014 | Bruder et al. |
| 8,765,463 B2 | 7/2014 | Harden et al. |
| 8,808,986 B2 | 8/2014 | Jacobson et al. |
| 8,815,563 B2 | 8/2014 | Davis et al. |
| 8,834,863 B2 | 9/2014 | Roy et al. |
| 8,846,031 B2 | 9/2014 | Roy et al. |
| 8,865,182 B2 | 10/2014 | Mayall et al. |
| 8,920,813 B2 | 12/2014 | Bruder et al. |
| 8,940,290 B2 | 1/2015 | Roy et al. |
| 8,974,777 B2 | 3/2015 | Cascallo et al. |
| 9,017,672 B2 | 4/2015 | Yu et al. |
| 9,018,182 B2 | 4/2015 | Koh et al. |
| 9,056,090 B2 | 6/2015 | Colloca et al. |
| 9,061,055 B2 | 6/2015 | Fueyo et al. |
| 9,133,483 B2 | 9/2015 | Wilson et al. |
| 9,163,261 B2 | 10/2015 | Kollipara et al. |
| 9,187,733 B2 | 11/2015 | Studies |
| 9,200,041 B2 | 12/2015 | Lieber et al. |
| 9,206,238 B2 | 12/2015 | Roy et al. |
| 9,217,159 B2 | 12/2015 | Roy et al. |
| 9,217,160 B2 | 12/2015 | Studies |
| 9,267,153 B2 | 2/2016 | Curiel |
| 9,315,827 B2 | 4/2016 | Wang et al. |
| 9,359,618 B2 | 6/2016 | Roy et al. |
| 9,382,551 B2 | 7/2016 | Roy et al. |
| 9,410,129 B2 | 8/2016 | Ranki et al. |
| 9,476,061 B2 | 10/2016 | Baker et al. |
| 9,493,745 B2 | 11/2016 | Lee et al. |
| 9,555,089 B2 | 1/2017 | Shiratsuchi et al. |
| 9,593,346 B2 | 3/2017 | Roy et al. |
| 9,597,363 B2 | 3/2017 | Roy et al. |
| 9,682,133 B2 | 6/2017 | Crystal et al. |
| 9,688,727 B2 | 6/2017 | Lieber et al. |
| 9,714,435 B2 | 7/2017 | Dicks et al. |
| 9,718,863 B2 | 8/2017 | Colloca et al. |
| 9,790,519 B2 | 10/2017 | Wei et al. |
| 9,885,090 B2 | 2/2018 | Studies |
| 9,913,866 B2 | 3/2018 | Studies |
| 10,016,470 B2 | 7/2018 | Bonastre et al. |
| 10,034,905 B2 | 7/2018 | Seymour et al. |
| 10,046,067 B2 | 8/2018 | Yun et al. |
| 10,066,215 B2 | 9/2018 | Lee et al. |
| 10,071,126 B2 | 9/2018 | Kumon et al. |
| 10,077,430 B2 | 9/2018 | Lee et al. |
| 10,080,774 B2 | 9/2018 | Fueyo et al. |
| 10,113,182 B2 | 10/2018 | Roy et al. |
| 10,149,873 B2 | 12/2018 | Roy et al. |
| 10,150,798 B2 | 12/2018 | Lieber et al. |
| 10,155,930 B2 | 12/2018 | Holm |
| 10,232,053 B2 | 3/2019 | Hicklin et al. |
| 10,272,162 B2 | 4/2019 | McVey et al. |
| 10,294,493 B2 | 5/2019 | Wang et al. |
| 10,316,065 B2 | 6/2019 | Carrió et al. |
| 10,376,549 B2 | 8/2019 | Shayakhmetov et al. |
| 10,391,183 B2 | 8/2019 | Fueyo-Margareto et al. |
| 10,501,757 B2 | 12/2019 | Roy et al. |
| 10,538,744 B2 | 1/2020 | Holm |
| 10,544,192 B2 | 1/2020 | Colloca et al. |
| 10,604,549 B2 | 3/2020 | Alemany Bonastre et al. |
| 10,611,803 B2 | 4/2020 | Lieber et al. |
| 10,617,729 B2 | 4/2020 | Dobbins |
| 10,738,325 B2 | 8/2020 | Studies |
| 2001/0039046 A1 | 11/2001 | Yeh et al. |
| 2002/0037274 A1 | 3/2002 | Williams et al. |
| 2002/0086411 A1 | 7/2002 | Holm et al. |
| 2002/0106382 A1 | 8/2002 | Young et al. |
| 2002/0142989 A1 | 10/2002 | Alemany et al. |
| 2002/0151069 A1 | 10/2002 | Korokhov |
| 2002/0168343 A1 | 11/2002 | Curiel et al. |
| 2002/0187128 A1 | 12/2002 | Imperiale |
| 2002/0193327 A1 | 12/2002 | Nemerow |
| 2002/0193328 A1 | 12/2002 | Ketner |
| 2003/0017138 A1 | 1/2003 | Havenga et al. |
| 2003/0021768 A1 | 1/2003 | Shen |
| 2003/0027338 A1 | 2/2003 | Freimuth |
| 2003/0073072 A1 | 4/2003 | Havenga et al. |
| 2003/0082146 A1 | 5/2003 | van Es |
| 2003/0082150 A1 | 5/2003 | Boon Falleur et al. |
| 2003/0082811 A1 | 5/2003 | Orlando et al. |
| 2003/0092162 A1 | 5/2003 | Shankara et al. |
| 2003/0095989 A1 | 5/2003 | Irving et al. |
| 2003/0099615 A1 | 5/2003 | Tikoo |
| 2003/0099619 A1 | 5/2003 | Wickham et al. |
| 2003/0104625 A1 | 6/2003 | Cheng et al. |
| 2003/0138405 A1 | 7/2003 | Fueyo et al. |
| 2003/0143730 A1 | 7/2003 | Blanche et al. |
| 2003/0166286 A1 | 9/2003 | Wickham et al. |
| 2003/0170899 A1 | 9/2003 | McVey et al. |
| 2003/0175244 A1 | 9/2003 | Curiel et al. |
| 2003/0175245 A1 | 9/2003 | Brough et al. |
| 2003/0215948 A1 | 11/2003 | Kaleko et al. |
| 2003/0219899 A1 | 11/2003 | Korokhov |
| 2003/0220284 A1 | 11/2003 | Yotnda et al. |
| 2004/0002060 A1 | 1/2004 | Kaleko et al. |
| 2004/0038205 A1 | 2/2004 | Van Raaij et al. |
| 2004/0091456 A1 | 5/2004 | Nakai et al. |
| 2004/0102382 A1 | 5/2004 | Schughart et al. |
| 2004/0146489 A1 | 7/2004 | Yu et al. |
| 2004/0175362 A1 | 9/2004 | Curiel et al. |

(56) References Cited

U.S. PATENT DOCUMENTS

| | | |
|---|---|---|
| 2004/0185555 A1 | 9/2004 | Emini et al. |
| 2004/0191222 A1 | 9/2004 | Emini et al. |
| 2004/0191761 A1 | 9/2004 | Routes |
| 2004/0213764 A1 | 10/2004 | Wold et al. |
| 2004/0219516 A1 | 11/2004 | Bennett et al. |
| 2004/0219543 A1 | 11/2004 | Wirtz |
| 2004/0265277 A1 | 12/2004 | Holm |
| 2005/0032045 A1 | 2/2005 | Tikoo et al. |
| 2005/0036989 A1 | 2/2005 | Shen et al. |
| 2005/0079158 A1 | 4/2005 | Zhou et al. |
| 2005/0095231 A1 | 5/2005 | Curiel et al. |
| 2005/0095705 A1 | 5/2005 | Kadan et al. |
| 2005/0169891 A1 | 8/2005 | Vogels et al. |
| 2005/0181507 A1 | 8/2005 | Havenga et al. |
| 2005/0186178 A1 | 8/2005 | Ennist |
| 2005/0201936 A1 | 9/2005 | Wold et al. |
| 2005/0201978 A1 | 9/2005 | Lipton |
| 2005/0232900 A1 | 10/2005 | Vogels et al. |
| 2005/0238622 A1 | 10/2005 | Axelrod et al. |
| 2005/0260162 A1 | 11/2005 | Fueyo et al. |
| 2005/0271622 A1 | 12/2005 | Zhou et al. |
| 2005/0277193 A1 | 12/2005 | Wickham et al. |
| 2005/0287120 A1 | 12/2005 | Fisher et al. |
| 2006/0002893 A1 | 1/2006 | Vigne et al. |
| 2006/0034804 A1 | 2/2006 | Gregory et al. |
| 2006/0099178 A1 | 5/2006 | Holm |
| 2006/0104953 A1 | 5/2006 | Havenga et al. |
| 2006/0140910 A1 | 6/2006 | Gregory et al. |
| 2006/0147420 A1 | 7/2006 | Fueyo et al. |
| 2006/0182718 A1 | 8/2006 | Roth et al. |
| 2006/0211115 A1 | 9/2006 | Roy et al. |
| 2006/0228334 A1 | 10/2006 | Rosa Calatrava et al. |
| 2006/0257370 A1 | 11/2006 | Hermiston et al. |
| 2006/0281090 A1 | 12/2006 | Lieber et al. |
| 2006/0286121 A1 | 12/2006 | Gall et al. |
| 2006/0292122 A1 | 12/2006 | Hermiston et al. |
| 2006/0292682 A1 | 12/2006 | Hawkins et al. |
| 2007/0003923 A1 | 1/2007 | Nemerow |
| 2007/0110719 A1 | 5/2007 | Holm |
| 2007/0122817 A1 | 5/2007 | Church et al. |
| 2007/0202080 A1 | 8/2007 | Yun et al. |
| 2007/0202524 A1 | 8/2007 | Murphy |
| 2007/0253932 A1 | 11/2007 | Gregory et al. |
| 2007/0254357 A1 | 11/2007 | Gregory et al. |
| 2007/0292396 A1 | 12/2007 | Fueyo et al. |
| 2007/0292954 A1 | 12/2007 | Elledge |
| 2008/0069836 A1 | 3/2008 | Nabel et al. |
| 2008/0089864 A1 | 4/2008 | Bonastre et al. |
| 2008/0108129 A1 | 5/2008 | Pitcovski et al. |
| 2008/0112929 A1 | 5/2008 | Kovesdi et al. |
| 2008/0118470 A1 | 5/2008 | Ennist et al. |
| 2008/0124360 A1 | 5/2008 | Seggern |
| 2008/0213220 A1 | 9/2008 | Fisher et al. |
| 2008/0242608 A1 | 10/2008 | Bonni et al. |
| 2008/0247996 A1 | 10/2008 | Yu et al. |
| 2008/0254059 A1 | 10/2008 | Bett et al. |
| 2009/0074810 A1 | 3/2009 | Roy et al. |
| 2009/0111144 A1 | 4/2009 | Bebbington |
| 2009/0202565 A1 | 8/2009 | Labow et al. |
| 2009/0232800 A1 | 9/2009 | Holm |
| 2009/0280089 A1 | 11/2009 | Benihoud et al. |
| 2009/0311219 A1 | 12/2009 | Bonastre et al. |
| 2010/0008977 A1 | 1/2010 | Boulikas et al. |
| 2010/0034774 A1 | 2/2010 | Vogels et al. |
| 2010/0047208 A1 | 2/2010 | Ke |
| 2010/0075951 A1 | 3/2010 | Cardin et al. |
| 2010/0075998 A1 | 3/2010 | Vanotti et al. |
| 2010/0098668 A1 | 4/2010 | Seth |
| 2010/0151576 A1 | 6/2010 | Li et al. |
| 2010/0233125 A1 | 9/2010 | Tagawa |
| 2010/0272753 A1 | 10/2010 | Ketner et al. |
| 2010/0292166 A1 | 11/2010 | Lee et al. |
| 2010/0310554 A1 | 12/2010 | Holm |
| 2010/0311145 A1 | 12/2010 | Holm |
| 2011/0053249 A1 | 3/2011 | Bonastre et al. |
| 2011/0059135 A1 | 3/2011 | Kovesdi et al. |
| 2011/0086063 A1 | 4/2011 | Crystal et al. |
| 2011/0104788 A1 | 5/2011 | Baker et al. |
| 2011/0189234 A1 | 8/2011 | Van Beusechem et al. |
| 2011/0256524 A1 | 10/2011 | Lee et al. |
| 2011/0275093 A1 | 11/2011 | Holm |
| 2011/0286999 A1 | 11/2011 | Holm |
| 2012/0020924 A1 | 1/2012 | Nakai et al. |
| 2012/0039877 A1 | 2/2012 | Holm |
| 2012/0207711 A1 | 8/2012 | Fueyo et al. |
| 2013/0058897 A1 | 3/2013 | Lee et al. |
| 2013/0101557 A1 | 4/2013 | Yun et al. |
| 2013/0130292 A1 | 5/2013 | Szalay et al. |
| 2013/0231267 A1 | 9/2013 | O'Shea et al. |
| 2013/0243729 A1 | 9/2013 | O'Shea et al. |
| 2013/0243731 A1 | 9/2013 | Dias et al. |
| 2013/0323205 A1 | 12/2013 | Diaconu et al. |
| 2013/0345295 A1 | 12/2013 | Wang et al. |
| 2014/0023619 A1 | 1/2014 | Kosai et al. |
| 2014/0199688 A1 | 7/2014 | Mizuguchi et al. |
| 2014/0294890 A1 | 10/2014 | Ketner et al. |
| 2014/0341857 A1 | 11/2014 | Bressy et al. |
| 2014/0348791 A1 | 11/2014 | Barouch et al. |
| 2014/0377294 A1 | 12/2014 | Fueyo-Margareto et al. |
| 2014/0377295 A1 | 12/2014 | Ertl et al. |
| 2015/0005397 A1 | 1/2015 | O'Shea et al. |
| 2015/0017127 A1 | 1/2015 | O'Shea et al. |
| 2015/0071881 A1 | 3/2015 | Bonastre et al. |
| 2015/0086579 A1 | 3/2015 | Mayall et al. |
| 2015/0202324 A1 | 7/2015 | Hemminki et al. |
| 2015/0232880 A1 | 8/2015 | Hemminki et al. |
| 2015/0246949 A1 | 9/2015 | Lieber et al. |
| 2015/0352203 A1 | 12/2015 | Wilson et al. |
| 2015/0374766 A1 | 12/2015 | Studies |
| 2016/0017294 A1 | 1/2016 | Reid et al. |
| 2016/0051603 A1 | 2/2016 | Roy et al. |
| 2016/0053235 A1 | 2/2016 | O'Shea et al. |
| 2016/0082100 A1 | 3/2016 | Ranki et al. |
| 2016/0090574 A1 | 3/2016 | Fisher et al. |
| 2016/0102295 A1 | 4/2016 | Roy et al. |
| 2016/0143967 A1 | 5/2016 | Fueyo-Margareto et al. |
| 2016/0208287 A1 | 7/2016 | Hemminki et al. |
| 2016/0244783 A1 | 8/2016 | Roy et al. |
| 2016/0289645 A1 | 10/2016 | Tufaro et al. |
| 2017/0035818 A1 | 2/2017 | Seymour et al. |
| 2017/0073647 A1 | 3/2017 | Fisher et al. |
| 2017/0080069 A1 | 3/2017 | Cerullo et al. |
| 2017/0096646 A1 | 4/2017 | Roy et al. |
| 2017/0137786 A1 | 5/2017 | Hemminki et al. |
| 2017/0183636 A1 | 6/2017 | Roy et al. |
| 2017/0190752 A1 | 7/2017 | Holm |
| 2017/0202893 A1 | 7/2017 | Studies |
| 2017/0252443 A1 | 9/2017 | Holm |
| 2017/0314044 A1 | 11/2017 | Davydova et al. |
| 2017/0348405 A1 | 12/2017 | Shiratsuchi et al. |
| 2018/0000966 A1 | 1/2018 | Dicks et al. |
| 2018/0051301 A1 | 2/2018 | Rentschler et al. |
| 2018/0072809 A1 | 3/2018 | Hemminki et al. |
| 2018/0100164 A1 | 4/2018 | Wei et al. |
| 2018/0104288 A1 | 4/2018 | Galili et al. |
| 2018/0163190 A1 | 6/2018 | Gerardy-Schahn et al. |
| 2018/0216081 A1 | 8/2018 | Colloca et al. |
| 2018/0221423 A1 | 8/2018 | O'Shea et al. |
| 2018/0318365 A1 | 11/2018 | Yeung et al. |
| 2018/0346929 A1 | 12/2018 | Kosai et al. |
| 2018/0355374 A1 | 12/2018 | Studies |
| 2018/0355379 A1 | 12/2018 | O'Shea et al. |
| 2018/0369417 A1 | 12/2018 | Yun et al. |
| 2019/0055522 A1 | 2/2019 | Holm |
| 2019/0062395 A1 | 2/2019 | Merchant et al. |
| 2019/0070233 A1 | 3/2019 | Yeung et al. |
| 2019/0093085 A1 | 3/2019 | Tufaro et al. |
| 2019/0136204 A1 | 5/2019 | Reid et al. |
| 2019/0142967 A1 | 5/2019 | Hicklin et al. |
| 2019/0175716 A1 | 6/2019 | Gilbert et al. |
| 2019/0183946 A1 | 6/2019 | Bonastre et al. |
| 2019/0201462 A1 | 7/2019 | Tufaro et al. |
| 2019/0201551 A1 | 7/2019 | Curiel |
| 2019/0233845 A1 | 8/2019 | Maloveste et al. |

(56) References Cited

U.S. PATENT DOCUMENTS

| | | |
|---|---|---|
| 2019/0247452 A1 | 8/2019 | Lan et al. |
| 2019/0269794 A1 | 9/2019 | McVey et al. |
| 2019/0275092 A1 | 9/2019 | Tufaro et al. |
| 2019/0275093 A1 | 9/2019 | Aboody et al. |
| 2019/0300905 A1 | 10/2019 | Ammendola et al. |
| 2019/0314523 A1 | 10/2019 | Studies |
| 2019/0314525 A1 | 10/2019 | O'Shea et al. |
| 2019/0345204 A1 | 11/2019 | Carrió et al. |
| 2019/0350992 A1 | 11/2019 | Cascallo Piqueras et al. |
| 2019/0352616 A1 | 11/2019 | Reid et al. |
| 2019/0352669 A1 | 11/2019 | Reid et al. |
| 2019/0374589 A1 | 12/2019 | Suzuki et al. |
| 2019/0388487 A1 | 12/2019 | Shayakhmetov et al. |
| 2020/0014798 A1 | 1/2020 | Hicklin et al. |
| 2020/0032223 A1 | 1/2020 | Reid et al. |
| 2020/0078415 A1 | 3/2020 | Reid et al. |
| 2020/0095560 A1 | 3/2020 | Holm |
| 2020/0102352 A1 | 4/2020 | Colloca et al. |

FOREIGN PATENT DOCUMENTS

| | | | | |
|---|---|---|---|---|
| CN | 102191245 A | 9/2011 | | |
| EP | 0689447 | 4/1999 | | |
| EP | 0931830 | 3/2001 | | |
| EP | 0760675 | 8/2001 | | |
| EP | 1167533 | 1/2002 | | |
| EP | 1284294 | 2/2003 | | |
| EP | 1413586 | 4/2004 | | |
| EP | 1196616 | 12/2004 | | |
| EP | 1185279 | 1/2005 | | |
| EP | 0851769 | 2/2005 | | |
| EP | 0861329 | 3/2005 | | |
| EP | 1181382 | 3/2005 | | |
| EP | 1121137 | 7/2005 | | |
| EP | 0991763 | 9/2005 | | |
| EP | 1294918 | 10/2005 | | |
| EP | 0889969 | 11/2005 | | |
| EP | 1498129 | 11/2005 | | |
| EP | 1593742 | 11/2005 | | |
| EP | 0920524 | 12/2005 | | |
| EP | 1307573 | 1/2006 | | |
| EP | 0978566 | 5/2006 | | |
| EP | 0778889 | 7/2006 | | |
| EP | 1070118 | 10/2006 | | |
| EP | 1214098 | 11/2006 | | |
| EP | 1230378 | 6/2007 | | |
| EP | 1550722 | 6/2007 | | |
| EP | 1187919 | 11/2007 | | |
| EP | 0863987 | 1/2008 | | |
| EP | 0920514 | 1/2008 | | |
| EP | 1159438 | 7/2008 | | |
| EP | 1266022 | 10/2008 | | |
| EP | 1678193 | 12/2008 | | |
| EP | 1054064 | 12/2009 | | |
| EP | 2012822 | 1/2010 | | |
| EP | 1816204 | 10/2010 | | |
| EP | 1749098 | 12/2010 | | |
| EP | 1799836 | 12/2010 | | |
| EP | 1816205 | 8/2011 | | |
| EP | 1818408 | 8/2011 | | |
| EP | 1409748 | 10/2011 | | |
| EP | 1180932 | 1/2012 | | |
| EP | 1466001 | 4/2012 | | |
| EP | 1743041 | 6/2012 | | |
| EP | 1446479 | 8/2012 | | |
| EP | 1649028 | 8/2012 | | |
| EP | 1990418 | 8/2012 | | |
| EP | 2311499 | 8/2012 | | |
| EP | 1636370 | 4/2014 | | |
| EP | 1767642 | 4/2014 | | |
| EP | 1689445 | 2/2015 | | |
| EP | 2350269 | 9/2015 | | |
| EP | 2403951 | 9/2015 | | |
| EP | 2643465 | 5/2016 | | |
| EP | 2428229 | 8/2016 | | |
| EP | 2459716 | 8/2016 | | |
| EP | 2220241 | 9/2016 | | |
| EP | 2325298 | 10/2016 | | |
| EP | 2379586 | 11/2016 | | |
| EP | 2220242 | 12/2016 | | |
| EP | 2774985 | 12/2016 | | |
| EP | 2163260 | 3/2017 | | |
| EP | 2580234 | 3/2017 | | |
| EP | 2798069 | 3/2017 | | |
| EP | 2855685 | 3/2017 | | |
| EP | 2900818 | 6/2017 | | |
| EP | 2301582 | 7/2017 | | |
| EP | 3049520 | 7/2017 | | |
| EP | 1453543 | 8/2017 | | |
| EP | 2463362 | 11/2017 | | |
| EP | 2558481 | 12/2017 | | |
| EP | 2682459 | 12/2017 | | |
| EP | 2714916 | 1/2018 | | |
| EP | 2391638 | 6/2018 | | |
| EP | 2563919 | 6/2018 | | |
| EP | 2971008 | 7/2018 | | |
| EP | 2606137 | 8/2018 | | |
| EP | 2855669 | 10/2018 | | |
| EP | 2986311 | 11/2018 | | |
| EP | 3145537 | 12/2018 | | |
| EP | 2654786 | 2/2019 | | |
| EP | 3280798 | 6/2019 | | |
| EP | 3029144 | 7/2019 | | |
| EP | 3150706 | 7/2019 | | |
| EP | 2809788 | 9/2019 | | |
| EP | 3071697 | 10/2019 | | |
| EP | 3274363 | 10/2019 | | |
| EP | 3460052 | 10/2019 | | |
| JP | 2005-525779 | 9/2005 | | |
| JP | 2007-530004 | 11/2007 | | |
| JP | 2008-517627 | 5/2008 | | |
| JP | 2010-527324 | 8/2010 | | |
| JP | 2011-524904 | 9/2011 | | |
| WO | WO 96/18418 | 6/1996 | | |
| WO | WO 98/54346 | 12/1998 | | |
| WO | WO 98/55641 | 12/1998 | | |
| WO | WO 99/44423 | 9/1999 | | |
| WO | WO 00/03029 | 1/2000 | | |
| WO | WO 00/22137 | 4/2000 | | |
| WO | WO 00/42208 | 7/2000 | | |
| WO | WO 01/02431 | 1/2001 | | |
| WO | WO 01/004282 | 1/2001 | | |
| WO | WO-0104282 A2 * | 1/2001 | ............ | A61K 35/761 |
| WO | WO 01/21217 | 3/2001 | | |
| WO | WO 01/23004 | 4/2001 | | |
| WO | WO 01/90392 | 11/2001 | | |
| WO | WO 01/98513 | 12/2001 | | |
| WO | WO 02/46372 | 6/2002 | | |
| WO | WO 03/064666 | 8/2003 | | |
| WO | WO 03/076605 | 9/2003 | | |
| WO | WO 2003/092579 | 11/2003 | | |
| WO | WO 03/104467 | 12/2003 | | |
| WO | WO 2004/018627 | 3/2004 | | |
| WO | WO 2004/031357 | 4/2004 | | |
| WO | WO 2005/001103 | 1/2005 | | |
| WO | WO 2005/010149 | 2/2005 | | |
| WO | WO 2005/023848 | 3/2005 | | |
| WO | WO 2005/030261 | 4/2005 | | |
| WO | WO 2005/065348 | 7/2005 | | |
| WO | WO 2005/075506 | 8/2005 | | |
| WO | WO 2005/107474 | 11/2005 | | |
| WO | WO 2005/113781 | 12/2005 | | |
| WO | WO 2005/117993 | 12/2005 | | |
| WO | WO 2006/086357 | 8/2006 | | |
| WO | WO 2006/119449 | 11/2006 | | |
| WO | WO 2007/124065 | 11/2007 | | |
| WO | WO 2008/095168 | 8/2008 | | |
| WO | WO 2008/150496 | 12/2008 | | |
| WO | WO 2009/065800 | 5/2009 | | |
| WO | WO 2010/024483 | 3/2010 | | |
| WO | WO 2010/037027 | 4/2010 | | |
| WO | WO 2011/133040 | 10/2011 | | |
| WO | WO 2012/003287 | 1/2012 | | |
| WO | WO 2012/022496 | 2/2012 | | |

(56) References Cited

FOREIGN PATENT DOCUMENTS

| | | | |
|---|---|---|---|
| WO | WO 2012/024350 | 2/2012 | |
| WO | WO 2012/024351 | 2/2012 | |
| WO | WO 2012/038606 | 3/2012 | |
| WO | WO 2012/083297 | 6/2012 | |
| WO | WO 2013/036791 | 3/2013 | |
| WO | WO 2013/135615 | 9/2013 | |
| WO | WO 2013/138505 | 9/2013 | |
| WO | WO 2014/000026 | 1/2014 | |
| WO | WO 2014/153204 | 9/2014 | |
| WO | WO 2014/170389 | 10/2014 | |
| WO | WO 2015/155370 | 10/2015 | |
| WO | WO 2016/049201 | 3/2016 | |
| WO | WO-2016049201 A1 * | 3/2016 | ........... A61K 31/436 |
| WO | WO 2017/062511 | 4/2017 | |
| WO | WO 2017/147265 | 8/2017 | |
| WO | WO 2017/147269 | 8/2017 | |
| WO | WO 2018/078220 | 5/2018 | |
| WO | WO 2018/083257 | 5/2018 | |
| WO | WO 2018/083258 | 5/2018 | |
| WO | WO 2018/083259 | 5/2018 | |
| WO | WO 2018/104919 | 6/2018 | |
| WO | WO 2018/201017 | 11/2018 | |
| WO | WO 2018/204677 | 11/2018 | |
| WO | WO 2018/218083 | 11/2018 | |
| WO | WO 2019/016756 | 1/2019 | |
| WO | WO 2019/057745 | 3/2019 | |
| WO | WO 2019/073059 | 4/2019 | |
| WO | WO 2019/086450 | 5/2019 | |
| WO | WO 2019/086456 | 5/2019 | |
| WO | WO 2019/086461 | 5/2019 | |
| WO | WO 2019/086466 | 5/2019 | |
| WO | WO 2019/158914 | 8/2019 | |
| WO | WO 2019/179977 | 9/2019 | |
| WO | WO 2019/179979 | 9/2019 | |
| WO | WO 2019/191494 | 10/2019 | |
| WO | WO 2019/199859 | 10/2019 | |
| WO | WO 2019/202118 | 10/2019 | |
| WO | WO 2019/239311 | 12/2019 | |
| WO | WO 2020/014539 | 1/2020 | |
| WO | WO 2020/046130 | 3/2020 | |
| WO | WO 2020/076820 | 4/2020 | |

OTHER PUBLICATIONS

Dias et al., "Targeted cancer immunotherapy with oncolytic adenovirus coding for a fully human monoclonal antibody specific for CTLA-4," Gene Therapy, vol. 19:988-998, 2012.
Kurihara et al., "Selectivity of a replication-competent adenovirus for human breast carcinoma cells expressing the MUC1 antigen," J. Clin. Invest., vol. 106:763-771, 2000.
Shimizu et al., "Development of a Novel Adenovirus Vector Exhibiting MicroRNA-mediated Suppression of the Leaky Expression of Adenovirus Genes," Yakugaku Zasshi, vol. 132:1407-1412, 2012 (in Japanese) (English abstract).
Suzuki et al., "miR-122A-Regulated Expression of a Suicide Gene Prevents Hepatotoxicity Without Altering Antitumor Effects in Suicide Gene Therapy," Mol. Ther., vol. 16:1719-1726, 2008.
Ji et al., "Oncolytic Adenoviruses Delivering Herpes Simplex Virus Thymidine Kinase Suicide Gene Reduces the Growth of Human Retinoblastoma in an in vivo Mouse Model," Experimental Eye Res., 89:193-199, 2009.
Kubo et al., "Complete Regression of Human Malignant Mesothelioma Xenografts Following Local Injection of Midkine Promoter-Driven Oncolytic Adenovirus," J. Gene Med., 12:681-692, 2010.
Loskog, "Immunostimulatory Gene Therapy Using Oncolytic Viruses as Vehicles," Viruses, 7:5780-5791, 2015.
Doronin et al., "Tumor-Specific, Replication-Competent Adenovirus Vectors Overexpressing the Adenovirus Death Protein," J. Virol., vol. 74:6147-6155, 2000.
Doronin et al., "Overexpression of the Adp (E3-11.6K) Protein Increases Cell Lysis and Spread of Adenovirus," Virology 305: 378-387, 2003.

International Search Report and Written Opinion for PCT/US2019/026626, dated Jun. 24, 2019 (12 pages).
Volk et al., "Enhanced Adenovirus Infection of Melanoma Cells by Fiber- Modification," Cancer Biol Ther 2(5): 511-515, 2003.
Fueyo et al., "A mutant oncolytic adenovirus targeting the Rb pathway produces anti-glioma effect in vivo," Oncogene 19:2-12, 2000.
Li, "Self-Cleaving Fusion Tags for Recombinant Protein Production," Biotechnol. Lett., vol. 33:869-881, 2011.
Wu et al., "The application of intein in the research of membrane protein," Chemistry of Life 35(2):200-205, 2015.
Alba et al., "Gutless adenovirus: last-generation adenovirus for gene therapy," Gene Ther 12:S18-S27, 2005.
Alba et al., "Identification of coagulation factor (F)X binding sites on the adenovirus serotype 5 hexon: effect of mutagenesis on FX interactions and gene transfer," Blood 114(5): 965-971, 2009.
Alonso et al., "Combination of the oncolytic adenovirus ICOVIR-5 with chemotherapy provides enhanced anti-glioma effect in vivo," Cancer Gene Ther 14:756-761, 2007.
Barton, et al., "Second-Generation Replication-Competent Oncolytic Adenovirus Armed with Improved Suicide Genes and ADP Gene Demonstrates Greater Efficacy without Increased Toxicity", Molecular Therapy, 2006, 13(2):347-356.
Batzer et al., "Enhanced evolutionary PCR using oligonucleotides with inosine at the 3'-terminus", Nucleic Acid Research, 1991, 19(18):5081.
Bauerschmitz et al., "Tissue-Specific Promoters Active in CD44+ CD24-llow Breast Cancer Cells," Cancer Res 68(14):5533-5539, 2008.
Bayle et al., "Rapamycin Analogs with Differential Binding Specificity Permit Orthogonal Control of Protein Activity," Chem Biol 13:99-107, 2006.
Behar et al., "Llama Single-Domain Antibodies Directed against Nonconventional Epitopes of Tumor-Associated Carcinoembryonic Antigen Absent from Nonspecific Cross-Reacting Antigen," FEBS J., vol. 276:3881-3893, 2009.
Belousova et al., "Modulation of Adenovirus Vector Tropism via Incorporation of Polypeptide Ligands into the Fiber Protein," J Virol 76(17):8621-8631, 2002.
Berge et al., "Pharmaceutical Salts", Journal of Pharmaceutical Science, 1977, 66: 1-19.
Bett et al., "DNA sequence of the deletion/insertion in early region 3 of Ad5 dl309," Virus Res 39: 75-82, 1995.
Binkowski et al., "Ligand-Regulated Peptides: A General Approach for Modulating Protein-Peptide Interactions with Small Molecules," Chem. Biol., vol. 12: 847-855, 2005.
Bradshaw et al., "Biodistribution and inflammatory profiles of novel pen ton and hexon double-mutant serotype 5 adenoviruses," J Control Release 164(3): 394-402, 2012.
Bremnes et al., "The Role of Tumor Stroma in Cancer Progression and Prognosis," J. Thorac. Oneal., vol. 6:209-217, 2011.
Card et al., "MicroRNA silencing improves the tumor specificity of adenoviral transgene expression," Cancer Gene Ther 19: 451-459, 2012.
Chen et al., "Identification of an 11-kDa FKBP12-rapamycin-binding domain within the 289-kDa FKBP12-rapamycin-associated protein and characterization of a critical serine residue," Proc Natl Acad Sci USA 92:4947-4951, 1995.
Cheo et al., "Concerted Assembly and Cloning of Multiple DNA Segments Using In Vitro Site-Specific Recombination: Functional Analysis of Multi-Segment Expression Clones," Genome Res 14:2111-2120, 2004.
Chong et al., "A System for Small-Molecule Control of Conditionally Replication- Competent Adenoviral Vectors," Mal Ther 5(2):195-203, 2002.
Chopra, "Recombinant Adenovirus with Enhanced Green Fluorescent Protein," Molecular Imaging and Contrast Agent Database (MICAD), Bethesda, MD: National Center for Biotechnology Information (US) (2004-2013): (Dec. 9, 2007, updated Jan. 2, 2008), 5 pp.
Evans et al., "Relocalization of the Mre11-Rad50-Nbs1 Complex by the Adenovirus E4 ORF3 Protein Is Required for Viral Replication", Journal of Virology, 2005, 79(10):6207-6215.

(56) References Cited

OTHER PUBLICATIONS

Extended European Search Report dated Dec. 11, 2013 for European Application No. 11818698.0, 10 pages.
Extended European Search Report for European Application No. 13760821.2, dated Sep. 30, 2015.
Fang et al., "An Antibody Delivery System for Regulated Expression of Therapeutic Levels of Monoclonal Antibodies In Vivo," Mal. Ther., vol. 15:1153-1159, 2007.
Finke et al., "Tracking Fluorescence-Labeled Rabies Virus: Enhanced Green Fluorescent Protein-Tagged Phosphoprotein P Supports Virus Gene Expression and Formation of Infectious Particles," J. Viral., vol. 78(22): 12333-12343, 2004.
Frese et al., "Selective PDZ protein-dependent stimulation of phosphatidylinositol 3-kinase by the adenovirus E4-ORF1 oncoprotein," Oncogene 22: 710-721, 2003.
Fuerer et al., "Adenoviruses with Tcf binding sites in multiple early promoters show enhanced selectivity for tumour cells with constitutive activation of the wnt signalling pathway," Gene Ther 9:270-281, 2002.
Funston et al., "Expression of heterologous genes in oncol ytic adenoviruses using picornaviral 2A sequences that trigger ribosome skipping," J Gen Viral 89:389-396, 2008.
Gall et al., "Construction and Characterization of Hexon-Chimeric Adenoviruses: Specification of Adenovirus Serotype," J Virol 72(12): 10260-10264, 1998.
Gibson et al., "Enzymatic Assembly of DNA Molecules up to Several Hundred Kilobases," Nature Meth., vol. 6:343-360, 2009.
Glasgow et al., "A Strategy for Adenovirus Vector Targeting with a Secreted Single Chain Antibody," PLoS One, vol. 4:e8355, 2009.
Havenga et al., "Novel Replication-Incompetent Adenoviral B-group Vectors: High Vector Stability and Yield in PER.C6 Cells," J. Gen. Viral., vol. 87:2135-2143, 2006.
Hawkins et al., "Gene delivery from the E3 region of replicating human adenovirus: evaluation of the E3B region," Gene Therapy 8, 1142-1148, 2001.
Heise et al., "An Adenovirus ElA Mutant that Demonstrates Potent and Selective Systemic Anti-Tumoral Efficacy," Nat Med. 6: 1134-1139, 2000.
Helin et al., "Heterodimerization of the Transcription Factors E2F-1 and DP-1 is required for Binding to the Adenovirus E4 (ORF6/7) Protein," J Virol 68: 5027-5035, 1994.
Henikoff et al., "Amino acid substitution matrices from protein blocks", Proc. Natl. Acad. Sci. USA , 1992, 89:10915-10919.
Hernandez-Aya et al. "Targeting the Phosphatidylinositol 3-Kinase Signaling Pathway in Breast Cancer", The Oncologist, 16, pp. 404-414, 2011.
Holm et al., "Multidrug-resistance Cancer Cells Facilitate El-independent Adenovirus Replication: Impact for Cancer Gene Therapy," Cancer Res 64:322-328, 2004.
International Preliminary Report on Patentability and Written Opinion dated Feb. 19, 2013 for International Application No. PCT/US2011/048005, 5 pages.
International Search Report dated Mar. 23, 2012 for International Application No. PCT/US2011/048005, 6 pages.
Javier, "Cell polarity proteins: common targets for tumorigenic human viruses," Oncogene 27:7031-7046, 2008.
Johnson et al., "Selectively replicating adenoviruses targeting deregulated E2F activity are potent, systemic antitumor agents," Cancer Cell 1:325-337, 2012.
Ketzer et al., "Synthetic riboswitches for external regulation of genes transferred by replication-deficient and oncolytic adenoviruses," Nucleic Acids Res 40(21):e167 (10 pages), 2012.
Kim et al., "High Cleavage Efficiency of a 2A Peptide Derived from Porcine Teschovirus-1 in Human Cell Lines, Zebrafish and Mice," PLoS ONE, vol. 64:e18556, 2011.
Kirn, "Clinical research results with d11520 (Onyx-015, a replication-selective adenovirus for the treatment of cancer: what have we learned?", Gene Therapy, 2001, 8(2):89-98.

Kovesdi et al., "Role of an Adenovirus E2 Promoter Binding Factor in ELA Mediated Coordinate Gene Control," Proc Nat Acad Sci USA 84: 2180-2184, 1987.
Leicher et al., "Coexpression of the KCNA3B Gene Product with Kv1 .5 Leads to a Novel A-type Potassium Channel*", The Journal of Biological Chemistry, 1998, 273(52):35095-35101.
Leppard et al., "Adenovirus type 5 E4 Orf3 protein targets promyelocytic leukaemia (PML) protein nuclear domains for disruption via a sequence in PML isoform II that is predicted as protein as a protein interaction site of bioinformatics anaylsis", Journal of General Virology 2009, 90(1):95-104.
Li et al., "Harnessing homologous recombination in vitro to generate recombinant DNA via SLIC," Nat Methods 4(3):251-256, 2007.
Liu et al., "Oncolytic Adenoviral Vector Carrying the Cytosine Deaminase Gene for Melanoma Gene Therapy," Cancer Gene Ther., vol. 13:845-855, 2006.
Lopez et al., "A Tumor-stroma Targeted Oncolytic Adenovirus Replicated in Human Ovary Cancer Samples and Inhibited Growth of Disseminated Solid Tumors in Mice," Mal Ther 20(12):2222-2233, 2012.
McCormick, "Cancer Gene Therapy: Fringe or Cutting Edge?," Nature Rev. Cancer, vol. 1:130-141, 2001.
Minskaia et al., "Protein Coexpression Using FMDV 2A: Effect of "Linker" Residues," BioMed Research International, vol. 2013, 12 pp.
Mohr, "To replicate or not to replicate: achieving selective oncolytic virus replication in cancer cells through translational control," Oncogene, vol. 24:7697-7709, 2005.
Murakami et al., "Chimeric Adenoviral Vectors Incorporating a Fiber of Human Adenovirus 3 Efficiently Mediate Gene Transfer into Prostate Cancer Cells," The Prostate, vol. 70:362-376, 2009.
NCBI Accession No. CVI 10986, Jan. 11, 2011, 3 pages.
Nevels et al., "The Adenovirus E4orf6 can Promote EIA/EIB-induced Focus Formation by Interfering with p53 Tumor Suppressor Function," Proc. Natl. Acad. Sci. USA, vol. 94:1206-1211, 1997.
Office Action and Search Report from China Application No. 201380014047.7, dated Aug. 5, 2015 (English translation).
Ono et al., "Noninvasive Visualization of Adenovirus Replication with a Fluorescent Reporter in the E3 Region," Cancer Res., vol. 65: 10154-10158, 2005.
O'Shea et al., "Adenoviral Proteins Mimic Nutrient/Growth Signals to Activate the mTOR Pathway for Viral Replication," EMBO J., vol. 24:1211-1221, 2005.
O'Shea et al., "Adenovirus Overrides Cellular Checkpoints for Protein Translation," Cell Cycle 4(7):883-888, 2005.
O'Shea et al., "DNA Tumor Viruses—the Spies who Lyse Us," Curr. Opin. Genet. Dev., vol. 15:18-26, 2005.
O'Shea et al., "Viruses—seeking and destroying the tumor program," Oncogene 24: 7640-7655, 2005.
Pearson et al., "Improved tools for biological sequence comparison", Proc. Nat'/. Acad. Sci. USA , 1988, 85:2444-2448.
Pelka et al., "Adenovirus EIA Directly Targets the E2F/DP-1 Complex," J Viral 85(17):8841-8851, 2011.
Rossolini et al., "Use of deoxyinosine-containing primers vs degenerate primers for polymerase chain reaction based on ambiguous sequence information", Mo/. Cell. Probes, 1994, 8:91-98.
Roy et al., "Rescue of chimeric adenoviral vectors to expand the serotype repertoire," J Viral Methods 14:41-21, 2007.
Shapiro et al., "Recombinant Adenoviral Vectors Can Induce Expression of p73 via the E4-orf6/7 Protein," J Viral 80(11):5349-5360, 2006.
Shepard et al., "E4orf13 Is Necessary for Enhanced S-Phase Replication of Cell Cycle-Restricted Subgroup C Adenoviruses," J Virol 77(15):8593-8595, 2003.
Smith et al., "Comparison of Biosequences", Advances in Applied Mathematics, 1981, 2:482-489.
Soria et al., "Heterochromatin silencing of p53 target genes by a small viral protein", Nature, 2010, 466(7310):1076-1083.
Stanton et al. "Re-engineering adenovirus vector systems to enable high-throughput analyses of gene function" Bio Techniques 45: 659-668 (Dec. 2008).

(56) References Cited

OTHER PUBLICATIONS

Szymczak et al., "Correction of Multi-Gene Deficiency in vivo using a Single 'self-cleaving' 2A Peptide-Based Retroviral Vector," Nature Biotech., vol. 22:589-594, 2004.
Tan et al., "Coexpression of double or triple copies of the rabies virus glycoprotein gene using a 'self-cleaving' 2A peptide-based replication-defective human adenovirus serotype 5 vector," Biologicals, vol. 38:586-593, 2010.
Ullman et al., "Adenovirus E4 ORF3 Protein Inhibits the Interferon-Mediated Antiviral Response", Journal of Virology, 2007, 81(9):4744-4752.
Verheije et al., "Retargeting of Viruses to Generate Oncolytic Agents," Adv. Viral., vol. 2012:1-15, 2012.
Waehler et al., "Engineering targeted viral vectors for gene therapy," Nat Rev Genet 8(8):573-587, 2007.
Wang et al., "Identification of Specific Adenovirus E1A-N-Terminal Residues Critical to the Binding of Cellular Proteins and to the Control of Cell Growth," J. Viral., vol. 67:476-488, 1993.
Warram et al., "A Genetic Strategy for Combined Screening and Localized Imaging of Breast Cancer," Mal Imaging Biol 13:452-461, 2011.
Whyte et al., "Association between an Oncogene and an Anti-Oncogene: the Adenovirus E1A Proteins Bind to the Retinoblastoma Gene Product," Nature 334:124-129, 1988.
Yaghoubi et al., "Positron Emission Tomography Reporter Genes and Reporter Probes: Gene and Cell Therapy Applications," Theranostics, vol. 2:374-391, 2012.
Yount et al., "Strategy for Systematic Assembly of Large RNA and DNA Genomes: Transmissible Gastroenteritis Virus Model," J. Viral., vol. 74: 10600-10611, 2000.
Fukazawa et al., "Adenovirus-mediated cancer gene therapy and virotherapy (review)," *Int J Mol Med*, vol. 25:3-10, 2010.
Cho et al., "Efficacy of CD46-targeting chimeric Ad5/35 adenoviral gene therapy for colorectal cancers," *Oncotarget* 7(25):38210-38223, 2016.
Hoffman and Wildner, "Comparison on herpes simplex virus- and conditionally replicative adenovirus-based vectors for glioblastoma treatment," *Cancer Gene Ther* 14:627-639, 2007.
Ishii and Ochiai, "The origin of fibroblast recruited into cancer-induced stromal tissue," *KENBIKYO* 43(2):104-108, 2008 (in Japanese with English abstract).
Raki et al., "Utility of TK/GCV in the context of highly effective oncolysis mediated by a serotype 3 receptor targeted oncolytic adenovirus," *Gene Ther* 14:1380-1388, 2007.

\* cited by examiner

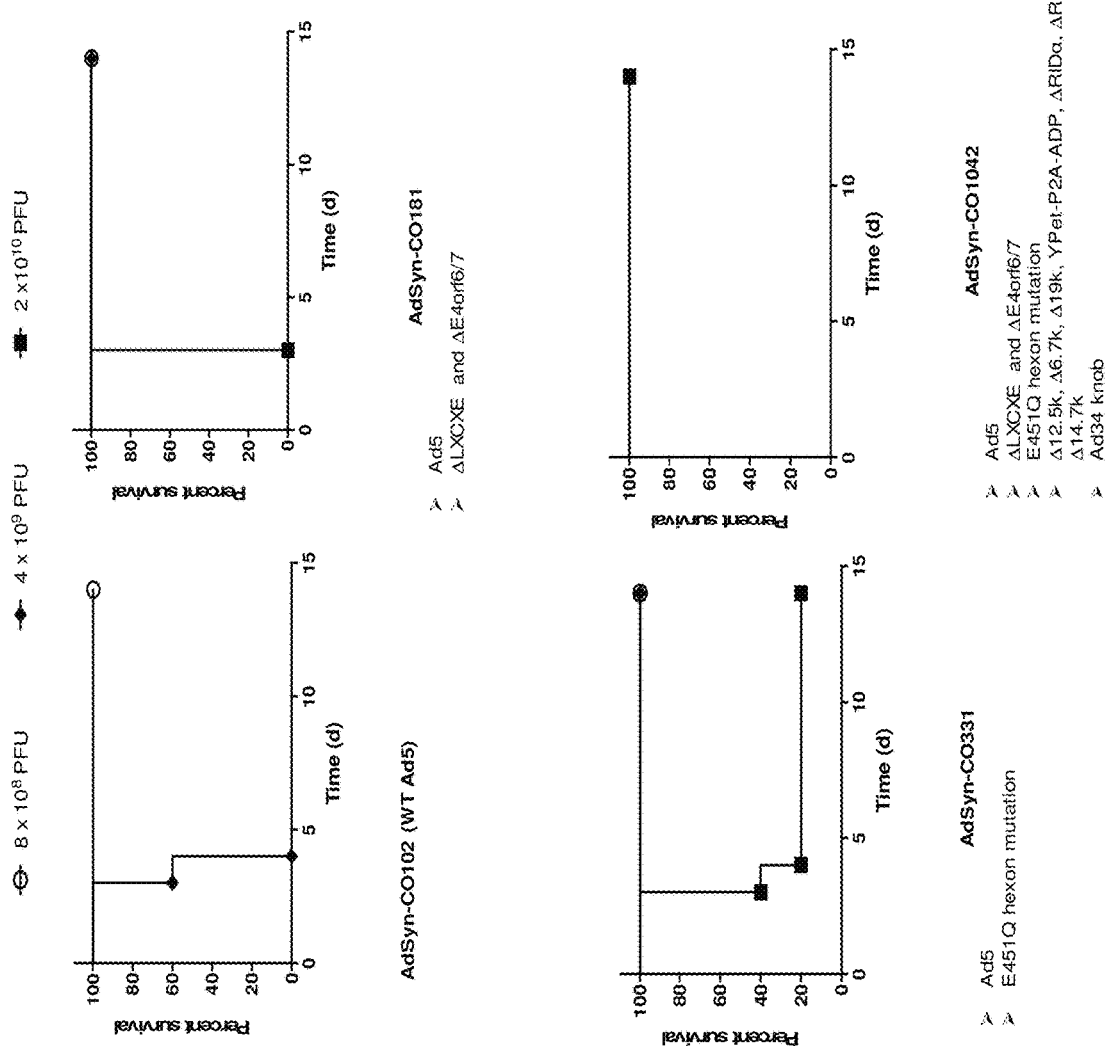

AdSyn-CO102 - WT Ad5
AdSyn-CO1000 - E1A[ΔLXCXE], ΔE3-6.7k/12.5k/19k, YPet-P2A-ADP, ΔRIDα/β/14.7K, ΔE4-ORF6/7
Hexon[E451Q], Total number of mice found dead at each time point

| Virus | Dose (pfu) | Days | | | | | | | | | | | | | | |
|---|---|---|---|---|---|---|---|---|---|---|---|---|---|---|---|---|
| | | 0 | 1 | 2 | 3 | 4 | 5 | 6 | 7 | 8 | 9 | 10 | 11 | 12 | 13 | 14 |
| AdSyn-CO102 | 2.0 x 10⁸ | 0 | 0 | 0 | 0 | 0 | 0 | 0 | 0 | 0 | 0 | 0 | 0 | 0 | 0 | 0/5 |
| AdSyn-CO1000 | 2.5 x 10⁸ | 0 | 0 | 0 | 0 | 0 | 0 | 0 | 0 | 0 | 0 | 0 | 0 | 0 | 0 | 0/5 |
| AdSyn-CO102 | 0.8 x 10⁹ | 0 | 0 | 0 | 0 | 0 | 0 | 0 | 2 | 2 | 2 | 2 | 2 | 2 | 2 | 2/5 |
| AdSyn-CO1000 | 1 x 10⁹ | 0 | 0 | 0 | 0 | 0 | 0 | 0 | 0 | 0 | 0 | 0 | 0 | 0 | 0 | 0/5 |
| AdSyn-CO102 | 3.2 x 10⁹ | 0 | 0 | 0 | 1 | 1 | 1 | 1 | 5 | 5 | 5 | 5 | 5 | 5 | 5 | 5/5 |
| AdSyn-CO1000 | 4 x 10⁹ | 0 | 0 | 0 | 0 | 0 | 0 | 0 | 0 | 0 | 0 | 0 | 0 | 0 | 2/5 | 2/5 |

Virus dose #1

Virus dose #2

Virus dose #3

ONCOLYTIC ADENOVIRUS WITH ENHANCED REPLICATION PROPERTIES COMPRISING MODIFICATIONS IN E1A, E3, AND E4

CROSS REFERENCE TO RELATED APPLICATIONS

This application is a continuation of PCT International Application No. PCT/US2019/026626, filed Apr. 9, 2019, published in English under PCT Article 21(2), which claims the benefit of U.S. Provisional Application No. 62/655,009, filed Apr. 9, 2018. The above-referenced applications are herein incorporated by reference in their entirety.

FIELD

This disclosure concerns tumor-selective recombinant adenoviruses that possess deletions or other modifications in the E3 region that enhance virus replication. This disclosure further concerns use of the recombinant adenoviruses for cancer treatment.

BACKGROUND

Cancer is a complex, debilitating disease that accounts for more than half a million deaths each year. There is a profound need for more effective, selective and safe treatments for cancer. Existing treatments, such as chemotherapy and surgery, rarely eliminate all malignant cells, and often exhibit deleterious side-effects that can outweigh therapeutic benefit.

One approach that has the potential to address many of the shortcomings of current cancer treatments is oncolytic adenoviral therapy (Pesonen et al., *Molecular Pharmaceutics* 8(1):12-28, 2010). Adenovirus (Ad) is a self-replicating biological machine. It consists of a linear double-stranded 36 kb DNA genome sheathed in a protein coat. Adenoviruses invade and hijack the cellular replicative machinery to reproduce, and upon assembly, induce lytic cell death to spread to surrounding cells. These very same cellular controls are targeted by mutations in cancer. This knowledge can be exploited to create synthetic viruses that act like guided missiles, specifically infecting and replicating in tumor cells, and lysing the cells to release thousands of virus progeny that can seek out and destroy distant metastases, while overcoming possible resistance. Thus, the goal of oncolytic virus design is to generate a virus that specifically replicates in cancer cells, but leaves normal cells unharmed. However, there have been significant challenges in designing a virus that can selectively replicate in cancer cells. Thus, there remains a need for viruses that selectively replicate in cancer cells with high efficiency. In addition, many oncolytic viruses have proven safe in human cancer patients in clinical trials, but most have fallen short on efficacy in treating advanced cancer. As such, there still remains a need to develop viruses with enhanced potency as compared to the current state of the art.

SUMMARY

Recombinant adenoviruses that exhibit enhanced replication kinetics in tumor cells are disclosed. Recombinant adenovirus genomes encoding recombinant adenoviruses with enhanced replication in tumor cells are also described.

Provided herein are recombinant adenovirus genomes that include an E1A region encoding a modified E1A protein; an E3 region encoding an adenovirus death protein (ADP) and having a modification in the coding sequences of at least three E3 genes selected from 12.5 k, 6.7 k, 19 k, RIDα, RIDβ and 14.7 k, wherein the modification prevents expression of the encoded protein; and an E4 region comprising a modification (such as a deletion) of the E4orf6/7 coding sequence.

In some embodiments, the recombinant adenovirus genome further encodes a targeting ligand, further encodes a chimeric fiber protein, further includes at least one modification to detarget an adenovirus from the liver, further includes a heterologous open reading frame (ORF), further includes a deletion of E4orf3, or any combination thereof.

Isolated cells that include a recombinant adenovirus genome disclosed herein are further provided. Also provided are compositions that include a recombinant adenovirus genome.

Recombinant adenoviruses encoded by the recombinant adenovirus genomes are further provided, as are compositions that include a recombinant adenovirus disclosed herein.

Further provided are methods of inhibiting tumor cell viability by contacting the tumor cell with a recombinant adenovirus genome, a recombinant adenovirus, or a composition disclosed herein.

Also provided are methods of inhibiting tumor progression or reducing tumor volume in a subject, and methods of treating cancer in a subject, by administering to the subject a therapeutically effective amount of a recombinant adenovirus genome, a recombinant adenovirus, or a composition disclosed herein.

Recombinant adenovirus genomes having a nucleotide sequence that is at least 95% identical to any one of SEQ ID NOs: 1, 2, 3, 4, 5, 6, 7, 8, 9, 10, 11, 12, 13, 14, 44, 45, 46, 47, 48, 49, 50, 51, 52, 53, 54, 55, 56, 57, 58, and 59 are also described. Further described are recombinant adenoviruses encoded by a nucleotide sequence at least 95% identical to any one of SEQ ID NOs: 1, 2, 3, 4, 5, 6, 7, 8, 9, 10, 11, 12, 13, 14, 44, 45, 46, 47, 48, 49, 50, 51, 52, 53, 54, 55, 56, 57, 58, and 59.

The foregoing and other objects and features of the disclosure will become more apparent from the following detailed description, which proceeds with reference to the accompanying figures.

BRIEF DESCRIPTION OF THE DRAWINGS

FIGS. 7A-7B are graphs showing the results of a safety and toxicity study of recombinant adenoviruses in C57BL/6 mice. Four different viruses were administered intravenously into different groups of mice (n=5 mice per group) in a volume of 200 µl on day 0 and again on day 7 at the indicated doses. Mice were then analyzed for survival (FIG. 7A) and elevated liver enzymes (FIG. 7B) to assess liver toxicity. (FIG. 7A) Mice were monitored for survival and gross signs of toxicity until day 14. While WT Ad5 caused lethal toxicity at a dose of $4 \times 10^9$ PFU, both AdSyn-CO181 and AdSyn-CO331 were tolerated at this dose. AdSyn-CO1042 was tolerated at an even higher dose of $2 \times 10^{10}$ PFU. (FIG. 7B) Blood samples were harvested from all mice on day −2 (pre-dose), day 2 (48 hours after dose 1) and day 9 (48 hours after dose 2) and frozen for subsequent analysis. Blood samples were assessed for the presence of various liver enzymes, such as alanine transaminase (ALT) and aspartate transaminase (AST). Results shown are the average AST and ALT levels from day 2 bleeds from the various treatment groups. The average pre-dose levels of AST and ALT from all mice are also shown.

SEQUENCE LISTING

Figure 1:
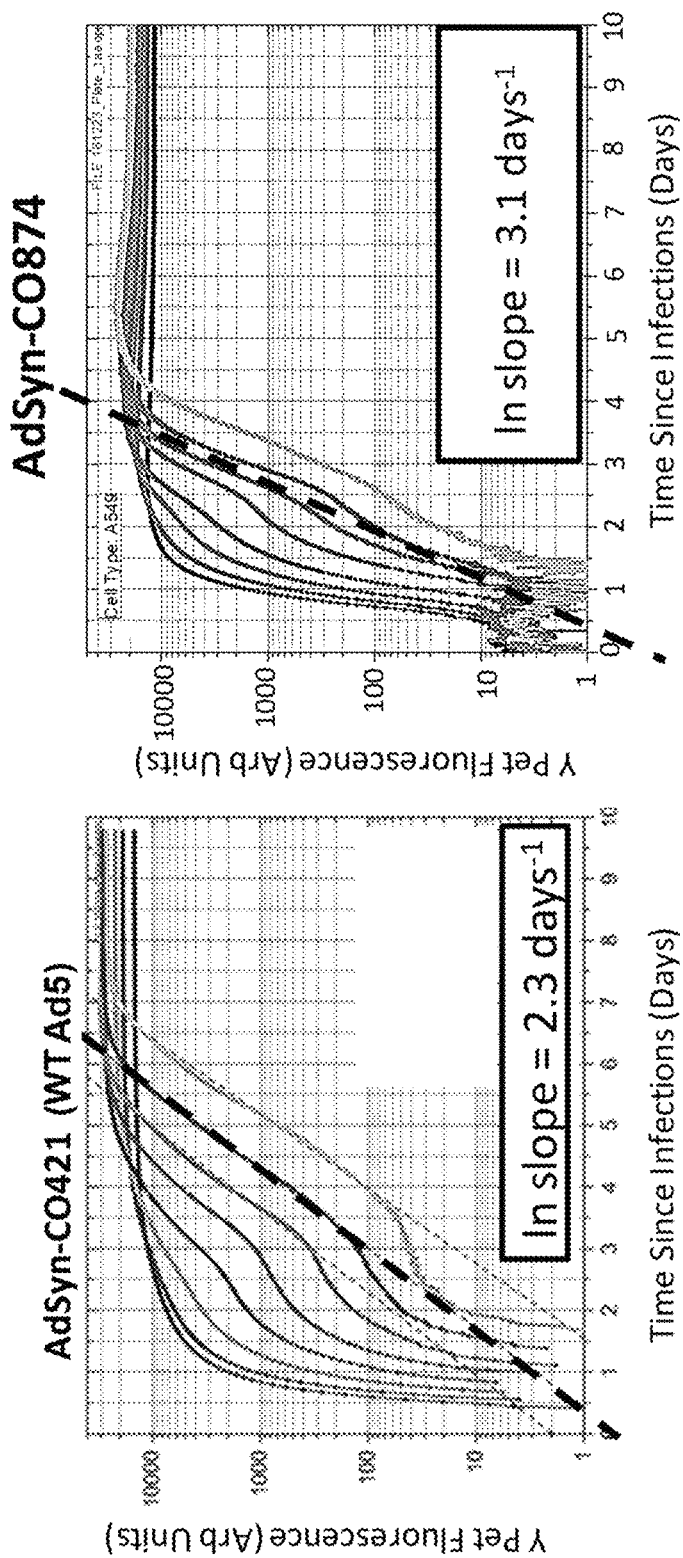
FIG. 1 is a pair of graphs comparing replication of WT Ad5 reporter virus AdSyn-CO421 and E3-deleted AdSyn-CO874 in A549 lung cancer cells. Deletion of six of the seven E3 genes in AdSyn-CO874 resulted in enhanced replication compared to the WT virus.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Oct. 8, 2020, 1.36 MB, which is incorporated by reference herein. In the accompanying sequence listing:

SEQ ID NO: 1 is the nucleotide sequence of synthetic adenovirus AdSyn-CO335.
SEQ ID NO: 2 is the nucleotide sequence of synthetic adenovirus AdSyn-CO821.
SEQ ID NO: 3 is the nucleotide sequence of synthetic adenovirus AdSyn-CO820.
SEQ ID NO: 4 is the nucleotide sequence of synthetic adenovirus AdSyn-CO819.
SEQ ID NO: 5 is the nucleotide sequence of synthetic adenovirus AdSyn-CO1020.
SEQ ID NO: 6 is the nucleotide sequence of synthetic adenovirus AdSyn-CO874.
SEQ ID NO: 7 is the nucleotide sequence of synthetic adenovirus AdSyn-CO1000.
SEQ ID NO: 8 is the nucleotide sequence of synthetic adenovirus AdSyn-CO1067.
SEQ ID NO: 9 is the nucleotide sequence of synthetic adenovirus AdSyn-CO1068.
SEQ ID NO: 10 is the nucleotide sequence of synthetic adenovirus AdSyn-CO1069.
SEQ ID NO: 11 is the nucleotide sequence of synthetic adenovirus AdSyn-CO964.
SEQ ID NO: 12 is the nucleotide sequence of synthetic adenovirus AdSyn-CO1041.
SEQ ID NO: 13 is the nucleotide sequence of synthetic adenovirus AdSyn-CO1042.
SEQ ID NO: 14 is the nucleotide sequence of synthetic adenovirus AdSyn-CO1139.
SEQ ID NO: 15 is the amino acid sequence of P2A.
SEQ ID NO: 16 is the amino acid sequence of F2A.
SEQ ID NO: 17 is the amino acid sequence of E2A.
SEQ ID NO: 18 is the amino acid sequence of T2A.
SEQ ID NO: 19 is the amino acid sequence of a modified P2A comprising GSG at the N-terminus.
SEQ ID NO: 20 is the amino acid sequence of a modified F2A comprising GSG at the N-terminus.
SEQ ID NO: 21 is the amino acid sequence of a modified E2A comprising GSG at the N-terminus.
SEQ ID NO: 22 is the amino acid sequence of a modified T2A comprising GSG at the N-terminus.
SEQ ID NO: 23 is the amino acid sequence of Ad5 E1A.
SEQ ID NO: 24 is the amino acid sequence of Ad5 E1A ΔLXCXE.
SEQ ID NO: 25 is the amino acid sequence of Ad5 E1A C124G.
SEQ ID NO: 26 is the amino acid sequence of Ad5 E1A Δ2-11.
SEQ ID NO: 27 is the amino acid sequence of Ad5 E1A Y47H C124G.
SEQ ID NO: 28 is the amino acid sequence of Ad5 E1A Δ2-11 Y47H C124G.
SEQ ID NO: 29 is the amino acid sequence of Ad5 E4orf6/7.
SEQ ID NO: 30 is the amino acid sequence of Ad5 fiber.
SEQ ID NO: 31 is the amino acid sequence of Ad5 FRB-fiber.
SEQ ID NO: 32 is the amino acid sequence of Ad5 FRB*-fiber.
SEQ ID NO: 33 is the amino acid sequence of EGFRVHH-GS-FKBP.
SEQ ID NO: 34 is the amino acid sequence of Ad5 hexon.
SEQ ID NO: 35 is the amino acid sequence of Ad5 hexon E451Q.
SEQ ID NO: 36 is the amino acid sequence of species A (Ad12) E1A.
SEQ ID NO: 37 is the amino acid sequence of species B (Ad7) E1A SEQ ID NO: 38 is the amino acid sequence of species C (Ad2) E1A.
SEQ ID NO: 39 is the amino acid sequence of species C (Ad5) E1A.
SEQ ID NO: 40 is the amino acid sequence of species D (Ad9) E1A.
SEQ ID NO: 41 is the amino acid sequence of species E (Ad4) E1A.
SEQ ID NO: 42 is the amino acid sequence of species F (Ad40) E1A.
SEQ ID NO: 43 is the amino acid sequence of species G (Ad52) E1A.
SEQ ID NO: 44 is the nucleotide sequence of synthetic adenovirus AdSyn-CO421.
SEQ ID NO: 45 is the nucleotide sequence of synthetic adenovirus AdSyn-CO1056.
SEQ ID NO: 46 is the nucleotide sequence of synthetic adenovirus AdSyn-CO1250.
SEQ ID NO: 47 is the nucleotide sequence of synthetic adenovirus AdSyn-CO1089.
SEQ ID NO: 48 is the nucleotide sequence of synthetic adenovirus AdSyn-CO1320.
SEQ ID NO: 49 is the nucleotide sequence of synthetic adenovirus AdSyn-CO1321.
SEQ ID NO: 50 is the nucleotide sequence of synthetic adenovirus AdSyn-CO1325.
SEQ ID NO: 51 is the nucleotide sequence of synthetic adenovirus AdSyn-CO1342.
SEQ ID NO: 52 is the nucleotide sequence of synthetic adenovirus AdSyn-CO1362.
SEQ ID NO: 53 is the nucleotide sequence of synthetic adenovirus AdSyn-CO1403.
SEQ ID NO: 54 is the nucleotide sequence of synthetic adenovirus AdSyn-CO1404.
SEQ ID NO: 55 is the nucleotide sequence of synthetic adenovirus AdSyn-CO869.
SEQ ID NO: 56 is the nucleotide sequence of synthetic adenovirus AdSyn-CO996.
SEQ ID NO: 57 is the nucleotide sequence of synthetic adenovirus AdSyn-CO999.
SEQ ID NO: 58 is the nucleotide sequence of synthetic adenovirus AdSyn-CO1002.
SEQ ID NO: 59 is the nucleotide sequence of synthetic adenovirus AdSyn-CO1347.
SEQ ID NO: 60 is the amino acid sequence of Ad34 fiber.

DETAILED DESCRIPTION

I. Abbreviations

Ad adenovirus
ADP adenovirus death protein
CAR coxsackie adenovirus receptor
EGFR epidermal growth factor receptor
ERAV equine rhinitis A virus FBVK fluorescence based viral kinetic
FKBP FK 506 binding protein
FMDV foot and mouth disease virus
FRB FKBP-rapamycin binding
IV intravenous
IT intratumoral
miR microRNA
MOI multiplicity of infection
mTOR mammalian target of rapamycin
ORF open reading frame
PSA prostate specific antigen
PTV1 porcine teschovirus-1
Rb retinoblastoma
RGD arginine-glycine-aspartate
TaV Thosea asigna virus
UTR untranslated region
WT wild-type II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

2A peptide: A type of self-cleaving peptide encoded by some RNA viruses, such as picornaviruses. 2A peptides function by making the ribosome skip the synthesis of a peptide bond at the C-terminus of a 2A element, leading to separation between the end of the 2A sequence and the downstream peptide (Kim et al., *PLoS One* 6(4):e18556, 2011). The "cleavage" occurs between the glycine and proline residues found on the C-terminus of the 2A peptide. Exemplary 2A peptides include, but are not limited to, the 2A peptides encoded by Thosea asigna virus (TaV), equine rhinitis A virus (ERAV), porcine teschovirus-1 (PTV1) and foot and mouth disease virus (FMDV), which are set forth herein as SEQ ID NOs: 15-18). In some embodiments, the 2A peptide comprises Gly-Ser-Gly at the N-terminus to improve cleavage efficiency (SEQ ID NOs: 19-22).

Adenovirus: A non-enveloped virus with a liner, double-stranded DNA genome and an icosahedral capsid. There are at least 68 known serotypes of human adenovirus, which are divided into seven species (species A, B, C, D, E, F and G). Different serotypes of adenovirus are associated with different types of disease, with some serotypes causing respiratory disease (primarily species B and C), conjunctivitis (species B and D) and/or gastroenteritis (species F and G).

Adenovirus death protein (ADP): A protein synthesized in the late stages of adenovirus infection that mediates lysis of cells and release of adenovirus to infect other cells. ADP is an integral membrane glycoprotein of 101 amino acids that localizes to the nuclear membrane, endoplasmic reticulum and Golgi. ADP was previously named E3-11.6K.

Administration: To provide or give a subject an agent, such as a therapeutic agent (e.g. a recombinant virus or recombinant virus genome), by any effective route. Exemplary routes of administration include, but are not limited to, injection (such as subcutaneous, intramuscular, intradermal, intraperitoneal, intratumoral, intraosseous, and intravenous), oral, intraductal, sublingual, rectal, transdermal, intranasal, vaginal and inhalation routes.

Antibody: A polypeptide ligand comprising at least a light chain and/or heavy chain immunoglobulin variable region which recognizes and binds (such as specifically recognizes and specifically binds) an epitope of an antigen. Immunoglobulin molecules are composed of a heavy and a light chain, each of which has a variable region, termed the variable heavy ($V_H$) region and the variable light ($V_L$) region, which together are responsible for binding the antigen recognized by the antibody. Antibodies include intact immunoglobulins and the variants and portions (fragments) of antibodies, such as single-domain antibodies (e.g. VH domain antibodies, or camelid VHH antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, IL); Kuby, J., *Immunology*, $3^{rd}$ Ed., W. H. Freeman & Co., New York, 1997.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth, such as psoriasis. In one embodiment, a chemotherapeutic agent is a radioactive compound. In one embodiment, a chemotherapeutic agent is a biologic, such as a therapeutic monoclonal antibody (e.g., specific for PD-1, PDL-1, CTLA-4, EGFR, VEGF, and the like). One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer.

Chimeric: Composed of at least two parts having different origins. In the context of the present disclosure, a "chimeric adenovirus" is an adenovirus having genetic material and/or proteins derived from at least two different serotypes (such as from Ad5 and a second serotype of adenovirus). In this context, a "capsid-swapped" adenovirus refers to a chimeric adenovirus in which the capsid proteins are derived from one serotype of adenovirus and the remaining proteins are derived from another adenovirus serotype. Similarly, a "chimeric fiber" is a fiber protein having amino acid sequence derived from at least two different serotypes of adenovirus. For example, a chimeric fiber can be composed of a fiber shaft from Ad5 and a fiber knob from a second serotype of adenovirus (such as Ad34).

Contacting: Placement in direct physical association; includes both in solid and liquid form.

Deletion: An adenovirus genome comprising a "deletion" of an adenovirus protein coding sequence (such as an E4orf6/7 coding sequence) refers to an adenovirus having a complete deletion of the protein coding sequence, or a partial deletion that results in the absence of expression of the protein.

Detargeted: In the context of the present disclosure, a "detargeted" adenovirus is a recombinant or synthetic adenovirus comprising one or more modifications that alter tropism of the virus such that is no longer infects, or no longer substantially infects, a particular cell or tissue type. In some embodiments, the recombinant or synthetic adenovirus comprises a capsid mutation, such as a mutation in the hexon protein (for example, E451Q) that detargets the virus from the liver. In some embodiments, the recombinant or synthetic adenovirus comprises a native capsid from an adenovirus that naturally does not infect, or does not substantially infect, a particular cell or tissue type. In some embodiments herein, the recombinant or synthetic adenovirus is liver detargeted and/or spleen detargeted.

E1A: The adenovirus early region 1A (E1A) gene and polypeptides expressed from the gene. The E1A protein plays a role in viral genome replication by driving cells into the cell cycle. As used herein, the term "E1A protein" refers to the proteins expressed from the E1A gene and the term includes E1A proteins produced by any adenovirus serotype. By way of example, the amino acid sequence of wild-type Ad5 E1A protein is set forth herein as SEQ ID NO: 23, and modified Ad5 E1A sequences are provided herein as SEQ ID NOs: 24-28. In addition, wild-type E1A protein sequences from a variety of different adenovirus serotypes are set forth herein as SEQ ID NOs: 36-43. In some embodiments, a modified E1A protein includes a protein having at least 80%, at least 85%, at least 90%, at least 95%, at least 96%, at least 97%, at least 98%, or at least 99% sequence identity to any one of SEQ ID NOs: 24, 25, 26, 27, 28, 36, 37, 38, 39, 40, 41, 42, or 43. The modified E1A proteins contemplated herein are those that contribute to the replication defects of a recombinant adenovirus in normal cells compared to tumor cells. The modified E1A proteins disclosed herein are Ad5 E1A proteins. However, corresponding modifications can be made in any desired serotype, and thus are encompassed by the present disclosure. For example, all species of human adenovirus contain the LXCXE motif, which in Ad5 corresponds to LTCHE (residues 122-126 of SEQ ID NO: 23). Similarly, the deletion of residues 2-11 and the Y47H and C124G substitutions are numbered with reference to Ad5 (e.g., SEQ ID NO: 5), but can be introduced into any other serotype.

E3: The adenovirus early region 3 (E3) gene and polypeptides expressed from the gene. In human adenoviruses, there are seven E3 proteins (encoded from 5' to 3'): 12.5 k (also known as gp12.5 kDa), 6.7 k (also known as CR1a), 19 k (also known as gp19 k), ADP (also known as CR1β or 11.6 k), RIDα (10.4 k), RIDβ (14.9 k), and 14.7K. The RIDα, RIDβ, and 14.7 k proteins make up the receptor internalization and degradation complex (RID), which localizes to the nuclear membrane and causes the endocytosis and degradation of a variety of receptors including CD95 (FasL receptor), and TNFR1 and 2 (TNF/TRAIL receptors) to protect infected cells from host antiviral responses. The 6.7 k protein is involved in apoptosis modulation of infection cells and the 19 k protein is known to inhibit insertion of class I MHC proteins in the infected host-cell membrane. ADP mediates lysis of infected cells. The function of the 12.5 k protein is unknown. As used herein, the E3A genes include the 12.5 k, 6.7 k and 19 k genes, and the E3B genes include the RIDα, RIDβ and 14.7 k genes. In some embodiments herein, the recombinant adenovirus genomes include a deletion of the E3A genes, a deletion of the E3B genes, or both. In other embodiments, the recombinant adenovirus genomes include a mutation in the coding sequences of the E3A genes or the E3B genes, or both, such that the mutation prevents expression of the encoded protein.

E4: The adenovirus early region 3 (E4) gene and polypeptides expressed from the gene. In human adenoviruses, the E4 region encodes at least six proteins, including E4orf1, E4orf2, E4orf3, E4orf4, E4orf6 and E4orf6/7. In some embodiments herein, the recombinant adenovirus genome includes a deletion of E4orf6/7. In some examples, the recombinant adenovirus genome further includes a deletion of E4orf3.

E4orf6/7: A protein encoded by the adenovirus E4 gene. The term "E4orf6/7 protein" includes E4orf6/7 proteins produced by the E4 gene from any adenovirus serotype. By way of example, the amino acid sequence of the wild-type Ad5 E4orf6/7 protein is set forth herein as SEQ ID NO: 29. In some embodiments, an E4orf6/7 protein includes a protein having at least 80%, at least 85%, at least 90%, at least 95%, at least 96%, at least 97%, at least 98%, or at least 99% sequence identity to any one of SEQ ID NO: 29. The modified E4orf6/7 proteins contemplated herein are those that contribute to the replication defects of a recombinant adenovirus in normal cells compared to tumor cells. In some embodiments, the modified E4orf6/7 protein comprises a mutation (such as a deletion) that abolishes or impairs its E2F binding site and/or impairs E2F interactions. In other embodiments, the modified E4orf6/7 protein comprises a modification that deletes or impairs the nuclear localization signal, which is required for efficient translocation of E2F4. Exemplary modifications of E4orf6/7 are discussed further in the sections below.

Epidermal growth factor receptor (EGFR): The cell-surface receptor for members of the EGF family of extracellular protein ligands. EGFR is also known as ErbB-1 and HER1. Many types of cancer contain mutations that lead to overexpression of EGFR.

Fiber: The adenovirus fiber protein is a trimeric protein that mediates binding to cell surface receptors. The fiber protein is comprised of a long N-terminal shaft and globular C-terminal knob.

FK506 binding protein (FKBP): A family of proteins expressed in eukaryotes that function as protein folding chaperones. FKBP is known for its capacity to bind rapamycin. An exemplary FKBP sequence is set forth herein as residues 132-238 of SEQ ID NO: 33.

FKBP-rapamycin binding (FRB): A domain of mammalian target of rapamycin (mTOR) that binds rapamycin. An exemplary sequence for FRB is set forth herein as residues 547-636 of SEQ ID NO: 31. A mutant form of FRB (referred to herein as "FRB*") that is capable of binding both rapamycin and rapalog (also known as AP21967) is set forth herein as residues 547-636 of SEQ ID NO: 32. FRB* contains a threonine to leucine substitution (T2098L) at position 2098 of human mTOR, which corresponds to residue 620 of SEQ ID NO: 32.

Fluorescent protein: A protein that emits light of a certain wavelength when exposed to a particular wavelength of light. Fluorescent proteins include, but are not limited to, green fluorescent proteins (such as GFP, EGFP, AcGFP1, Emerald, Superfolder GFP, Azami Green, mWasabi, TagGFP, TurboGFP, YPet and ZsGreen), blue fluorescent proteins (such as EBFP, EBFP2, Sapphire, T-Sapphire, Azurite and mTagBFP), cyan fluorescent proteins (such as ECFP, mECFP, Cerulean, CyPet, AmCyan1, Midori-Ishi Cyan, mTurquoise and mTFP1), yellow fluorescent proteins (EYFP, Topaz, Venus, mCitrine, YPet, TagYFP, PhiYFP, ZsYellow1 and mBanana), orange fluorescent proteins (Kusabira Orange, Kusabira Orange2, mOrange, mOrange2 and mTangerine), red fluorescent proteins (mRuby, mApple, mStrawberry, AsRed2, mRFP1, JRed, mCherry, HcRed1, mRaspberry, dKeima-Tandem, HcRed-Tandem, mPlum, AQ143, tdTomato and E2-Crimson), far-red fluorescent proteins (such as Katushka2S), orange/red fluorescence proteins (dTomato, dTomato-Tandem, TagRFP, TagRFP-T, DsRed, DsRed2, DsRed-Express (T1) and DsRed-Monomer) and modified versions thereof.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or polypeptide refers to a protein or polypeptide derived from a different source or species. Similarly, a heterologous ORF is an ORF derived from a different source or species.

Hexon: A major adenovirus capsid protein. An exemplary hexon sequence from Ad5 is set forth herein as SEQ ID NO: 34. A mutant hexon sequence comprising an E451Q substitution is set forth herein as SEQ ID NO: 35.

Immunomodulatory protein: A protein that alters (e.g. activates, enhances or suppresses) the immune system. Immunomodulators include, but are not limited to, cytokines (such as interleukin 2 (IL-2), IL-7, IL-12, GM-CSF, FLT3 ligand, or interferons), chemokines (such as CCL3, CCL26, CXCL7, CXCL9, and CXCL10), T cell activating ligands (such as anti-CD3 Abs or alloantigens), co-stimulatory molecules (such as B7.1/B7.2, OX40L, 4-1-BBL or CD40L), checkpoint blockade inhibitors (such as anti-PD-1 or anti-CTLA4 Abs), and small molecule immunomodulators.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). MicroRNAs modulate gene expression by promoting cleavage of target mRNAs or by blocking translation of the cellular transcript. In the context of the present disclosure, a "liver-specific microRNA" is a microRNA that is preferentially expressed in the liver, such as a microRNA that is expressed only in the liver, or a microRNA that is expressed significantly more in the liver as compared to other organs or tissue types.

Modification: A change in the sequence of a nucleic acid or protein sequence. For example, amino acid sequence modifications include, for example, substitutions, insertions and deletions, or combinations thereof. Insertions include amino and/or carboxyl terminal fusions as well as intrasequence insertions of single or multiple amino acid residues. Deletions are characterized by the removal of one or more amino acid residues from the protein sequence. In some embodiments herein, the modification (such as a substitution, insertion or deletion) results in a change in function, such as a reduction or enhancement of a particular activity of a protein. As used herein, "Δ" or "delta" refer to a deletion. For example, E1AΔLXCXE refers to an E1A polypeptide having a deletion of the LXCXE motif. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final mutant sequence. These modifications can be prepared by modification of nucleotides in the DNA encoding the protein, thereby producing DNA encoding the modification. Techniques for making insertion, deletion and substitution mutations at predetermined sites in DNA having a known sequence are well known in the art. A "modified" protein, nucleic acid or virus is one that has one or more modifications as outlined above.

Neoplasia, malignancy, cancer and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In some cases, lymphomas are considered solid tumors.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, human papilloma virus (HPV)-infected neoplasias, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

Oncolytic virus: A virus that selectively kills cells of a proliferative disorder, e.g., cancer/tumor cells. Killing of the cancer cells can be detected by any method established in the art, such as determining viable cell count, or detecting cytopathic effect, apoptosis, or synthesis of viral proteins in the cancer cells (e.g., by metabolic labeling, immunoblot, or RT-PCR of viral genes necessary for replication), or reduction in size of a tumor.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, PA, 15th Edition (1975), describes compositions and formulations suitable for pharmaceutical delivery of one or more therapeutic compounds, molecules or agents (e.g. a recombinant virus or recombinant virus genome disclosed herein). In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms "polypeptide," "peptide" and "protein" are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Rapamycin: A small molecule with known immunosuppressive and anti-proliferative properties. Rapamycin, also known as sirolimus, is a macrolide that was first discovered as a product of the bacterium *Streptomyces hygroscopicus*. Rapamycin binds and inhibits the activity of mTOR. Rapalog (also known as AP21967) is an analog of rapamycin.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus.

Replication defects: An adenovirus that exhibits "replication defects" in a non-tumor cell (compared to a tumor cell) refers to an adenovirus that exhibits reduced viral replication in normal cells compared to tumor cells. Replication defects are evidenced by, for example, a lack of viral late protein expression, a reduction in viral DNA synthesis, a reduced ability to induce E2F target genes (e.g. cyclin A and B), a reduced ability to elicit S phase entry and/or a reduced ability to induce cell killing in normal cells compared to tumor cells.

RGD peptide: A peptide with the tri-amino acid motif arginine-glycine-aspartate. The RGD motif is found in many matrix proteins, such as fibronectin, fibrinogen, vitronectin and osteopontin and plays a role in cell adhesion to the extracellular matrix.

Self-cleaving peptides: Peptides that induce the ribosome to skip the synthesis of a peptide bond at the C-terminus, leading to separation of the peptide sequence and a downstream polypeptide. Virally encoded 2A peptides are a type of self-cleaving peptide. Virally encoded 2A peptides include, for example, 2A peptides from porcine teschovirus-1 (PTV1), foot and mouth disease virus (FMDV), equine rhinitis A virus (ERAV) and Thosea asigna virus (TaV).

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are known. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Subject: Living multi-cellular vertebrate organisms, a category that includes human and non-human mammals, such as veterinary subjects (for example, mice, rats, rabbits, cats, dogs, pigs, and non-human primates).

Synthetic: Produced by artificial means in a laboratory, for example a synthetic nucleic acid or protein can be chemically synthesized in a laboratory.

Targeting ligand: In the context of the present disclosure, a "targeting ligand" is a protein that directs a recombinant adenovirus to a specific cell type that expresses a receptor or binding protein specific for the targeting ligand. In some embodiments, the targeting ligand is an antibody specific for a cell surface protein overexpressed in tumors (e.g. EGFR).

Therapeutic agent: A chemical compound, small molecule, recombinant virus or other composition, such as an antisense compound, antibody (such as a monoclonal antibody (mAb), for example an antagonistic mAb), peptide or nucleic acid molecule capable of inducing a desired therapeutic or prophylactic effect when properly administered to a subject. For example, therapeutic agents for cancer include agents that prevent or inhibit development or metastasis of the cancer.

Therapeutically effective amount: A quantity of a specified pharmaceutical or therapeutic agent (e.g. a recombinant virus) sufficient to achieve a desired effect in a subject, or in a cell, being treated with the agent. The effective amount of the agent can be dependent on several factors, including, but not limited to the subject or cells being treated, and the manner of administration of the therapeutic composition.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control.

In addition, the materials, methods, and examples are illustrative only and not intended to be limiting.

III. Overview of Several Embodiments

Tumor-selective recombinant adenoviruses that possess modifications (such as deletions, substitutions, and/or insertions) in the E3 region are described. In particular, the present disclosure describes the finding that modification (e.g., deletion) of at least three E3 genes (such as the E3A genes, or the E3B genes) such that E3 protein expression is abrogated, or modification (e.g., deletion) of six (12.5 k, 6.7 k, 19 k, RIDα, RIDβ and 14.7 k) of the seven E3 genes leads to enhanced virus replication (such as an increase of at least 20%, at least 50%, at least 75%, at least 90%, at least 95%, at least 100%, at least 200%, or at least 500%) relative to adenoviruses with a WT E3 region. The recombinant adenoviruses can further include additional modifications to allow selective replication in tumor cells and to detarget viruses from the liver. Use of the recombinant adenoviruses for cancer treatment is described. Also described are reporter virus versions of the oncolytic viruses, which can be used as diagnostic reagents, such as to determine whether a patient's tumor cells are likely to be responsive to the oncolytic virus.

The specific modifications disclosed herein are described with reference to the adenovirus 5 (Ad5) genome sequence. However, the same modifications and deletions could be made in any human adenovirus serotype. Adenovirus modifications for tumor-selectivity, liver detargeting, inducible retargeting, retargeting via chimeric fiber proteins, and other modifications are described in detail in PCT Publication No. WO 2016/049201, which is herein incorporated by reference in its entirety.

Provided herein are recombinant adenovirus genomes that include an E1A region encoding a modified E1a protein; an E3 region encoding an adenovirus death protein (ADP) and comprising a modification (such as a mutation, for example an amino acid substitution, or deletion of a gene or portion thereof) in the coding sequences of at least three E3 genes selected from 12.5 k, 6.7 k, 19 k, RIDα, RIDβ and 14.7 k, wherein the modification e.g., deletion) prevents expression of the encoded protein; and an E4 region having a modification (e.g., deletion) of the E4orf6/7 coding sequence.

In some embodiments, the modified E1A protein includes a deletion of the LXCXE motif; a deletion of residues 2-11; a C124G substitution; a Y47H substitution; a Y47H substitution and a C124G substitution; or a Y47H substitution, a C124G substitution and a deletion of residues 2-11 (for example wherein numbering is relative to SEQ ID NO: 23).

In some embodiments of the recombinant adenovirus genome, the at least three E3 genes comprise 12.5 k, 6.7 k and 19 k (the E3A genes). In some examples, the 12.5 k, 6.7 k and 19 k genes are deleted. In other examples, the 12.5 k, 6.7 k and 19 k genes comprise a mutated start codon, a mutation that introduces a premature stop codon, or both. In specific examples, the 12.5 k gene, the 6.7 k gene and/or the 19 k gene encodes a M1S amino acid substitution.

In other embodiments of the recombinant adenovirus genome, the at least three E3 genes comprise RIDα, RID and 14.7 k (the E3B genes). In some examples, the RIDα, RID and 14.7 k genes are deleted. In other examples, the RIDα, RIDβ and 14.7 k genes comprise a mutated start codon, a mutation that introduces a premature stop codon, or both. In specific examples, the RIDα gene encodes a M1K substitution; the RIDβ gene encodes M1K, C30G and M60stop substitutions; and/or the 14.7 k gene encodes a M1K, M9stop, M31stop and M39stop substitutions.

In yet other embodiments, the at least three E3 genes comprise 12.5 k, 6.7 k, 19 k, RIDα, RIDβ and 14.7 k (all E3 genes except ADP). In some examples, the 12.5 k, 6.7 k, 19 k, RIDα, RIDβ and 14.7 k genes are deleted. In other examples, the 12.5 k, 6.7 k, 19 k, RIDα, RIDβ and 14.7 k genes comprise a mutated a start codon, a mutation that introduces a premature stop codon, or both. In specific examples, the RIDα gene encodes a M1K substitution; the RIDβ gene encodes M1K, C30G and M60stop substitutions; and/or the 14.7 k gene encodes a M1K, M9stop, M31stop and M39stop substitutions.

In some embodiments, the recombinant adenovirus genome further comprises a deletion of E4orf3.

In some embodiments, the genome further encodes a targeting ligand fused to an FK506 binding protein (FKBP), and an adenovirus fiber protein fused to a wild-type FKBP-rapamycin binding (FRB) protein or a mutant FRB protein capable of binding rapalog. In some examples, the targeting ligand is a single domain antibody, such as a single domain antibody specific for EGFR.

In some embodiments, the genome further includes at least one modification to detarget an adenovirus from the liver. In some examples, the modification is a mutation in the hexon protein, such as a E451Q mutation (for example wherein numbering is relative to SEQ ID NO: 34). In some examples, the modification is one or more binding sites for a liver-specific microRNA. In particular examples, the one or more binding sites for the liver-specific microRNA are located in the 3'-UTR of E1A. The liver-specific microRNA can be, for example, miR-122, miR-30 or miR-192.

The some embodiments, the genome encodes a chimeric fiber protein. In some examples, the chimeric fiber protein comprises a fiber shaft from a first adenovirus serotype and a fiber knob from a second adenovirus serotype. In specific examples, the first adenovirus serotype is Ad5 and the second adenovirus serotype is Ad3, Ad9, Ad11, Ad12, Ad34 or Ad37. In one non-limiting example, the first adenovirus serotype is Ad5 and the second adenovirus serotype is Ad34. In one example, the Ad34 fiber knob comprises a modification, such as F242S, that prevents or inhibits binding to CD46 (wild-type Ad34 fiber sequence is set forth herein as SEQ ID NO: 60).

In some embodiments, the genome encodes a fiber protein modified to include an RGD peptide.

In some embodiments, the genome further includes a heterologous ORF. In some examples, the heterologous ORF is operably linked to and in the same reading frame as a self-cleaving peptide coding sequence and the ADP coding sequence. In some examples, the self-cleaving peptide is a 2A peptide. In specific examples, the 2A peptide comprises a porcine teschovirus-1 (PTV1) 2A (P2A) peptide, a foot and mouth disease virus (FMDV) 2A (F2A) peptide, an equine rhinitis A virus (ERAV) 2A (E2A) peptide or a Thosea asigna virus (TaV) 2A (T2A) peptide.

In some examples, the heterologous ORF is a reporter gene. In some examples, the reporter gene encodes a fluorescent protein, such as a green fluorescent protein, a yellow fluorescent protein or a red (or far-red) fluorescent protein. In specific examples, the fluorescent protein is YPet, mCherry or Katsushka2S. In other examples, the reporter gene encodes a soluble factor that can be detected in serum as a biomarker for virus replication. In specific non-limiting examples, the soluble factor is PSA. In yet other examples, the reporter gene encodes an imaging probe, such as a luciferase, a metalloprotein, a sodium iodide symporter or a thymidine kinase, such as herpes simplex virus thymidine kinase (HSV-tk).

In other examples, the heterologous ORF is a therapeutic gene encoding, for example, an RNAi sequence, a protein, an antibody or binding fragment thereof, a chemokine, a cytokine, an immunomodulator or an enzyme. In some examples, the therapeutic gene encodes an immunomodulatory protein.

In specific non-limiting examples, the immunomodulatory protein is a cytokine (such as, but not limited to, IL-1α, IL-1β, IL-6, IL-9, IL-12, IL-13, IL-17, IL-18, IL-22, IL-23, IL-24, IL-25, IL-26, IL-27, IL-33, IL-2, IL-4, IL-5, IL-7, IL-10, IL-15, IL-1RA, IFNα, IFNβ, IFNγ, TNFα, TGFβ, lymphotoxin A (LTA), GM-CSF, HMGB1, and FLT3 ligand).

In other specific examples, the immunomodulatory protein is a chemokine (such as, but not limited to, IL-8, CCL5, CCL17, CCL20, CCL22, CXCL9, CXCL10, CXCL11, CXCL13, CXCL12, CCL19, CCL21, CXCR2, CCR2, CCR4, CCR5, CCR6, CCR7, CCR8, CXCR3, CXCR4, CXCR5, and CRTH2).

In other specific examples, the immunomodulatory protein is a T cell stimulatory ligand (such as, but not limited to, cell surface anti-CD3, a bi-specific T cell engager (BiTe), a T cell stimulatory MHC/HLA molecule (allogeneic), or a tumor antigen) or a co-stimulatory molecule (such as B7.1, B7.2, OX40L, CD40L, CD70, LIGHT, ICOS, or 4-1BBL).

In yet other examples, the therapeutic gene encodes an antibody (such as a mAb, for example an antagonistic mAb), an antigen-binding fragment of an antibody, or a soluble antagonist. Specific non-limiting examples of such molecules include anti-VEGF, anti-TGF-β, soluble TGF-β receptor, anti-PD-1, PD-IL, and LAg3.

In some embodiments, the nucleotide sequence of the genome is at least 90%, at least 95%, at least 96%, at least 97%, at least 98%, at least 99% or at least 99.5% identical to SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 13, SEQ ID NO: 14, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 57 or SEQ ID NO: 59. In some examples, the nucleotide sequence of the genome comprises or consists of SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 13, SEQ ID NO: 14, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 57 or SEQ ID NO: 59.

Also provided here are isolated cells (such as mammalian cells, such as a mammalian tumor cell) that include a recombinant adenovirus genome disclosed herein.

Further provided are compositions that include a recombinant adenovirus genome disclosed herein and a pharmaceutically acceptable carrier, such as water or saline.

Also provided are isolated adenoviruses that include a recombinant adenovirus genome disclosed herein. Compositions that include an isolated adenovirus and a pharmaceutically acceptable carrier (such as water or saline) are further provided.

Further provided is a method of inhibiting tumor cell viability by contacting the tumor cell with a recombinant adenovirus genome, an adenovirus, or a composition described herein. In some embodiments, the method is an in vitro method. In other embodiments, the method is an in vivo method and contacting the tumor cell includes administering a therapeutically effective amount of the recombinant adenovirus genome, the adenovirus, or the composition, to a subject with a tumor.

Also provided is a method of inhibiting tumor progression or reducing tumor volume in a subject. The method includes administering to the subject a therapeutically effective amount of a recombinant adenovirus genome, an adenovirus, or a composition described herein.

Further provided is a method of treating cancer in a subject. The method includes administering to the subject a therapeutically effective amount of a recombinant adenovirus genome, a recombinant adenovirus, or a composition disclosed herein.

Also provided herein is a recombinant adenovirus genome, wherein the nucleotide sequence of the genome is at least 90%, at least 95%, at least 96%, at least 97%, at least 98%, at least 99% or at least 99.5% identical to SEQ ID NO: 2, SEQ ID NO: 6, SEQ ID NO: 11, SEQ ID NO: 12, SEQ ID NO: 45, SEQ ID NO: 46, SEQ ID NO: 55, SEQ ID NO: 56 or SEQ ID NO: 58. In some embodiments, the nucleotide sequence of the genome comprises or consists of SEQ ID NO: 2, SEQ ID NO: 6, SEQ ID NO: 11, SEQ ID NO: 12, SEQ ID NO: 45, SEQ ID NO: 46, SEQ ID NO: 55, SEQ ID NO: 56 or SEQ ID NO: 58. Isolated adenoviruses comprising a recombinant adenovirus genome are further provided.

IV. Wild-Type and Mutant Virus Sequences

Disclosed are recombinant adenovirus genomes comprising a nucleotide sequence at least 90%, at least 95%, at least 96%, at least 97%, at least 98% or at least 99% identical to any one of SEQ ID NOs: 1, 2, 3, 4, 5, 6, 7, 8, 9, 10, 11, 12, 13, 14, 44, 45, 46, 47, 48, 49, 50, 51, 52, 53, 54, 55, 56, 57, 58, or -59. In specific examples, the recombinant nucleic acid comprises or consists of the nucleotide sequence of any one of SEQ ID NOs: 1, 2, 3, 4, 5, 6, 7, 8, 9, 10, 11, 12, 13, 14, 44, 45, 46, 47, 48, 49, 50, 51, 52, 53, 54, 55, 56, 57, 58, or-59.

Also provided are vectors (such as a plasmid or viral vector) comprising the recombinant adenovirus genomes. In some embodiments, provided is a vector comprising a nucleic acid molecule at least 90%, at least 95%, at least 96%, at least 97%, at least 98% or at least 99% identical to any one of SEQ ID NOs: 1, 2, 3, 4, 5, 6, 7, 8, 9, 10, 11, 12, 13, 14, 44, 45, 46, 47, 48, 49, 50, 51, 52, 53, 54, 55, 56, 57, 58, or-59. In some examples, provided is a vector comprising a nucleic acid molecule comprising or consisting of the nucleotide sequence of any one of SEQ ID NOs: 1, 2, 3, 4, 5, 6, 7, 8, 9, 10, 11, 12, 13, 14, 44, 45, 46, 47, 48, 49, 50, 51, 52, 53, 54, 55, 56, 57, 58, or-59.

Provided below are exemplary wild-type and mutant adenovirus protein sequences expressed by the recombinant adenoviruses disclosed herein.

E1A and E4orf6/7 Mutants

In the E1A sequences below, the LXCXE motif is indicated by underline. This motif is present at amino acids 122-126 of Ad5 E1A (SEQ ID NO: 23). The Y47H and C124G substitutions are shown in bold. Modifications (including deletions) of E1A and E4orf6/7 contribute to tumor-selective replication of the recombinant adenoviruses disclosed herein.

```
Ad5 E1A (wild-type)
                                       (SEQ ID NO: 23)
MRHIICHGGVITEEMAASLLDQLIEEVLADNLPPPSHFEPPTLHELYDLD

VTAPEDPNEEAVSQIFPDSVMLAVQEGIDLLTFPPAPGSPEPPHLSRQPE

QPEQRALGPVSMPNLVPEVIDLTCHEAGFPPSDDEDEEGEEFVLDYVEHP
```

GHGCRSCHYHRRNTGDPDIMCSLCYMRTCGMFVYSPVSEPEPEPEPEPEP
ARPTRRPKMAPAILRRPTSPVSRECNSSTDSCDSGPSNTPPEIHPVVPLC
PIKPVAVRVGGRRQAVECIEDLLNEPGQPLDLSCKRPRP

Ad5 E1A ΔLXCXE
(SEQ ID NO: 24)
MRHIICHGGVITEEMAASLLDQLIEEVLADNLPPPSHFEPPTLHELYDLD
VTAPEDPNEEAVSQIFPDSVMLAVQEGIDLLTFPPAPGSPEPPHLSRQPE
QPEQRALGPVSMPNLVPEVIDAGFPPSDDEDEEGEEFVLDYVEHPGHGCR
SCHYHRRNTGDPDIMCSLCYMRTCGMFVYSPVSEPEPEPEPEPEPARPTR
RPKMAPAILRRPTSPVSRECNSSTDSCDSGPSNTPPEIHPVVPLCPIKPV
AVRVGGRRQAVECIEDLLNEPGQPLDLSCKRPRP

Ad5 E1A C124G
(SEQ ID NO: 25)
MRHIICHGGVITEEMAASLLDQLIEEVLADNLPPPSHFEPPTLHELYDLD
VTAPEDPNEEAVSQIFPDSVMLAVQEGIDLLTFPPAPGSPEPPHLSRQPE
QPEQRALGPVSMPNLVPEVIDLTGHEAGFPPSDDEDEEGEEFVLDYVEHP
GHGCRSCHYHRRNTGDPDIMCSLCYMRTCGMFVYSPVSEPEPEPEPEPEP
ARPTRRPKMAPAILRRPTSPVSRECNSSTDSCDSGPSNTPPEIHPVVPLC
PIKPVAVRVGGRRQAVECIEDLLNEPGQPLDLSCKRPRP

Ad5 E1A Δ2-11
(SEQ ID NO: 26)
MEEMAASLLDQLIEEVLADNLPPPSHFEPPTLHELYDLDVTAPEDPNEEA
VSQIFPDSVMLAVQEGIDLLTFPPAPGSPEPPHLSRQPEQPEQRALGPVS
MPNLVPEVIDLTCHEAGFPPSDDEDEEGEEFVLDYVEHPGHGCRSCHYHR
RNTGDPDIMCSLCYMRTCGMFVYSPVSEPEPEPEPEPEPARPTRRPKMAP
AILRRPTSPVSRECNSSTDSCDSGPSNTPPEIHPVVPLCPIKPVAVRVGG
RRQAVECIEDLLNEPGQPLDLSCKRPRP

Ad5 E1A Y47H C124G
(SEQ ID NO: 27)
MRHIICHGGVITEEMAASLLDQLIEEVLADNLPPPSHFEPPTLHELHDLD
VTAPEDPNEEAVSQIFPDSVMLAVQEGIDLLTFPPAPGSPEPPHLSRQPE
QPEQRALGPVSMPNLVPEVIDLTGHEAGFPPSDDEDEEGEEFVLDYVEHP
GHGCRSCHYHRRNTGDPDIMCSLCYMRTCGMFVYSPVSEPEPEPEPEPEP
ARPTRRPKMAPAILRRPTSPVSRECNSSTDSCDSGPSNTPPEIHPVVPLC
PIKPVAVRVGGRRQAVECIEDLLNEPGQPLDLSCKRPRP

Ad5 E1A Δ2-11 Y47H C124G
(SEQ ID NO: 28)
MEEMAASLLDQLIEEVLADNLPPPSHFEPPTLHELHDLDVTAPEDPNEEA
VSQIFPDSVMLAVQEGIDLLTFPPAPGSPEPPHLSRQPEQPEQRALGPVS
MPNLVPEVIDLTGHEAGFPPSDDEDEEGEEFVLDYVEHPGHGCRSCHYHR
RNTGDPDIMCSLCYMRTCGMFVYSPVSEPEPEPEPEPEPARPTRRPKMAP
AILRRPTSPVSRECNSSTDSCDSGPSNTPPEIHPVVPLCPIKPVAVRVGG
RRQAVECIEDLLNEPGQPLDLSCKRPRP

Species_A_Ad12_E1A
(SEQ ID NO: 36)
MRTEMTPLVLSYQEADDILEHLVDNFFNEVPSDDDLYVPSLYELYDLDVE
SAGEDNNEQAVNEFFPESLILAASEGLFLPEPPVLSPVCEPIGGECMPQL
HPEDMDLLCYEMGFPCSDSEDEQDENGMAHVSASAAAAAADREREEFQLD
HPELPGHNCKSCEHHRNSTGNTDLMCSLCYLRAYNMFIYSPVSDNEPEPN
STLDGDERPSPPKLGSAVPEGVIKPVPQRVTGRRRCAVESILDLIQEEER
EQTVPVDLSVKRPRCN Species_B_Ad7_E1A
(SEQ ID NO: 37)
MRHLRFLPQEIISSETGIEILEFVVNTLMGDDPEPPVQPFDPPTLHDLYD
LEVDGPEDPNEGAVNGFFTDSMLLAADEGLDINPPPETLVTPGVVVESGR
GGKKLPDLGAAEMDLRCYEEGFPPSDDEDGETEQSIHTAVNEGVKAASDV
FKLDCPELPGHGCKSCEFHRNNTGMKELLCSLCYMRMHCHFIYSPVSDDE
SPSPDSTTSPPEIQAPAPANVCKPIPVKPKPGKRPAVDKLEDLLEG
GDGPLDLSTRKLPRQ Species_C_Ad2_E1A
(SEQ ID NO: 38)
MRHIICHGGVITEEMAASLLDQLIEEVLADNLPPPSHFEPPTLHELYDLD
VTAPEDPNEEAVSQIFPDSVMLAVQEGIDLLTFPPAPGSPEPPHLSRQPE
QPEQRALGPVSMPNLVPEVIDLTCHEAGFPPSDDEDEEGEEFVLDYVEHP
GHGCRSCHYHRRNTGDPDIMCSLCYMRTCGMFVYSPVSEPEPEPEPEPEP
ARPTRRPKLVPAILRRPTSPVSRECNSSTDSCDSGPSNTPPEIHPVVPLC
PIKPVAVRVGGRRQAVECIEDLLNESGQPLDLSCKRPRP Species_C_Ad5_E1A
(SEQ ID NO: 39)
MRHIICHGGVITEEMAASLLDQLIEEVLADNLPPPSHFEPPTLHELYDLD
VTAPEDPNEEAVSQIFPDSVMLAVQEGIDLLTFPPAPGSPEPPHLSRQPE
QPEQRALGPVSMPNLVPEVIDLTCHEAGFPPSDDEDEEGEEFVLDYVEHP
GHGCRSCHYHRRNTGDPDIMCSLCYMRTCGMFVYSPVSEPEPEPEPEPEP
ARPTRRPKMAPAILRRPTSPVSRECNSSTDSCDSGPSNTPPEIHPVVPLC
PIKPVAVRVGGRRQAVECIEDLLNEPGQPLDLSCKRPRP Species_D_Ad9_E1A
(SEQ ID NO: 40)
MRHLRLLPSTVPGELAVLMLEDFVDTVLEDELHPSPFELGPTLQDLYDLE
VDAHDDDPNEEAVNLIFPESMILQADIANESTPLHTPTLSPIPELEEEDE
LDLRCYEEGFPPSDSEDERGEQTMALISDYACVIVEEQDVIEKSTEPVQG
CRNCQYHRDKSGDVNASCALCYMKQTFSFIYSPVSEDELSPSEEDHPSPP
ELSGETPLQVFRPTPVRPSGERRAAVDKIEDLLQDMGGDEPLDLSLKRPR
N Species_E_Ad4_E1A
(SEQ ID NO: 41)
MRHLRDLPDEEIIIASGSEILELVVNAMMGDDHPEPPTPFETPSLHDLYD
LEVDVPEDDPNEKAVNDLFSDAALLAAEEASSPSSDSDSSLHTPRHDRGE
KEIPGLKWEKMDLRCYEECLPPSDDEDEQAIQNAASHGVQAVSESFALDC
PPLPGHGCKSCEFHRINTGDKAVLCALCYMRAYNHCVYSPVSDADDETPT -continued
TESTLSPPEIGTSPSDNIVRPVPVRATGRRAAVECLDDLLQGGDEPLDLC

TRKRPRH

Species_F_Ad40_E1A
(SEQ ID NO: 42)
MRMLPDFFTGNWDDMFQGLLETEYVFDFPEPSEASEEMSLHDLFDVEVDG

FEEDANQEAVDGMFPERLLSEAESAAESGSGDSGVGEELLPVDLDLKCYE

DGLPPSDPETDEATEAEEEAAMPTYVNENENELVLDCPENPGRGCRACDF

HRGTSGNPEAMCALCYMRLTGHCIYSPISDAEGESESGSPEDTDFPHPLT

ATPPHGIVRTIPCRVSCRRRPAVECIEDLLEEDPTDEPLNLSLKRPKCS

Species_G_Ad52_E1A
(SEQ ID NO: 43)
MRLVPEMYGVFCSETVRNSDELLNTDLLDVPNSPVTSPPSLHDLFDVEVD

PPQDPNEDAVNSMFPECLFEAAEEGSHSSEESKRGEELDLKCYEECLPSS

DSETEQTGGDGCTEPVVKNEPVLDRPDQPGHGCRACAFHRNASGNPETLC

ALCYLRLTSDFVYSDVSDAEGDGDRSGSANSPCTLGAVVPVGIIKPVAVR

VSGRRCAVEKLEDLLQEEQTEPLDLSMKRPKLT

Ad5 E4orf6/7
(SEQ ID NO: 29)
MTTSGVPFGMTLRPTRSRLSRRTPYSRDRLPPFETETRATILEDHPLLPE

CNTLTMHNAWTSPSPPVKQPQVGQQPVAQQLDSDMNLSELPGEFINITDE

RLARQETVWNITPKNMSVTHDMMLFKASRGERTVYSVCWEGGGRLNTRVL

Recombinant adenoviruses having a genome encoding a modified E4orf6/7 protein that eliminates or impairs binding to E2F, or deletes or impairs the nuclear localization signal are contemplated herein. In some examples, the modified E4orf6/7 protein comprises a deletion of about 60, about 50, about 40, about 30, about 20 or about 10 amino acids at the C-terminus to delete/impair the E2F binding site. In other examples, the E4orf6/7 protein comprises a deletion, a frameshift or an insertion in the C-terminal 10 amino acids, or a deletion of 33 amino acids from the C-terminal third of the protein that abolish or impair E2F binding. In some embodiments, the mutations comprise amino acids 81-91 that impair the E2F interactions.

In other examples, the modified E4orf6/7 protein comprises an N-terminal deletion of 58 amino acids to abolish the nuclear localization sequence, which is required for efficient translocation of E2F4. There are eight arginine residues located between amino acids 13 and 38 of Ad2 and Ad5 E4orf6/7, which equates with greater than 25% arginine content for this region. The overall clustering of arginine residues in the N-terminus of E4orf6 is maintained in other adenovirus serotypes. Mutations that substitute arginine residues 16, 18, 21, 22, 27 and/or 29 for alanine (or other appropriate residues to abolish nuclear localization through this region) are contemplated.

In other examples, the modified E4orf6/7 protein comprises one or more modifications to eliminate or inhibit the ability of E4orf6/7 to induce E2F double site occupancy. Specific, non-limiting examples include a mutation of F125 to proline, alanine, lysine, aspartic acid or glutamic acid; or a mutation of D121 to P, A, K, R, G, F (wherein the amino acid position is relative to SEQ ID NO: 29).

Other E4orf6/7 mutations include: T133A, R101A, Q105P or any mutations that prevent E2F single site occupancy; M84N or P, G, K, L, H and/or E93A, or K, P, G, R, L, M that disrupt an alpha helix and prevent E2F binding (wherein the amino acid position is relative to SEQ ID NO: 29). Other contemplated mutations include T133Q or A, K, G, P, L, H; G141L, P, K H, F, A; or V149N, K, P, H, G, E, D (wherein the amino acid position is relative to SEQ ID NO: 29).

Also contemplated are recombinant adenoviruses and recombinant adenovirus genomes having a partial or complete deletion of E4orf6/7.

Fiber Sequences

In the recombinant Ad5 fiber sequences below, the FRB sequence is underlined. The mutation present in FRB* is shown in bold.

Ad5 fiber
(SEQ ID NO: 30)
MKRARPSEDTFNPVYPYDTETGPPTVPFLTPPFVSPNGFQESPPGVLSLR

LSEPLVTSNGMLALKMGNGLSLDEAGNLTSQNVTTVSPPLKKTKSNINLE

ISAPLTVTSEALTVAAAAPLMVAGNTLTMQSQAPLTVHDSKLSIATQGPL

TVSEGKLALQTSGPLTTTDSSTLTITASPPLTTATGSLGIDLKEPIYTQN

GKLGLKYGAPLHVTDDLNTLTVATGPGVTINNTSLQTKVTGALGFDSQGN

MQLNVAGGLRIDSQNRRLILDVSYPFDAQNQLNLRLGQGPLFINSAHNLD

INYNKGLYLFTASNNSKKLEVNLSTAKGLMFDATAIAINAGDGLEFGSPN

APNTNPLKTKIGHGLEFDSNKAMVPKLGTGLSFDSTGAITVGNKNNDKLT

LWTTPAPSPNCRLNAEKDAKLTLVLTKCGSQILATVSVLAVKGSLAPISG

TVQSAHLIIRFDENGVLLNNSFLDPEYWNFRNGDLTEGTAYTNAVGFMPN

LSAYPKSHGKTAKSNIVSQVYLNGDKTKPVTLTITLNGTQETGDTTPSAY

SMSFSWDWSGHNYINEIFATSSYTFSYIAQE

Ad5 FRB-fiber
(SEQ ID NO: 31)
MKRARPSEDTFNPVYPYDTETGPPTVPFLTPPFVSPNGFQESPPGVLSLR

LSEPLVTSNGMLALKMGNGLSLDEAGNLTSQNVTTVSPPLKKTKSNINLE

ISAPLTVTSEALTVAAAAPLMVAGNTLTMQSQAPLTVHDSKLSIATQGPL

TVSEGKLALQTSGPLTTTDSSTLTITASPPLTTATGSLGIDLKEPIYTQN

GKLGLKYGAPLHVTDDLNTLTVATGPGVTINNTSLQTKVTGALGFDSQGN

MQLNVAGGLRIDSQNRRLILDVSYPFDAQNQLNLRLGQGPLFINSAHNLD

INYNKGLYLFTASNNSKKLEVNLSTAKGLMFDATAIAINAGDGLEFGSPN

APNTNPLKTKIGHGLEFDSNKAMVPKLGTGLSFDSTGAITVGNKNNDKLT

LWTTPAPSPNCRLNAEKDAKLTLVLTKCGSQILATVSVLAVKGSLAPISG

TVQSAHLIIRFDENGVLLNNSFLDPEYWNFRNGDLTEGTAYTNAVGFMPN

LSAYPKSHGKTAKSNIVSQVYLNGDKTKPVTLTITLNGTQETGDT<u>EMWH

EGLEEASRLYFGERNVKGMFEVLEPLHAMMERGPQTLKETSFNQAYGRDL

MEAQEWCRKYMKSGNVKDLTQAWDLYYHVFRRISKQPSAYSMSFSWDWSG

HNYINEIFATSSYTFSYIAQE</u>

Ad5 FRB*-fiber
(SEQ ID NO: 32)
MKRARPSEDTFNPVYPYDTETGPPTVPFLTPPFVSPNGFQESPPGVLSLR

LSEPLVTSNGMLALKMGNGLSLDEAGNLTSQNVTTVSPPLKKTKSNINLE

ISAPLTVTSEALTVAAAAPLMVAGNTLTMQSQAPLTVHDSKLSIATQGPL

TVSEGKLALQTSGPLTTTDSSTLTITASPPLTTATGSLGIDLKEPIYTQN

```
GKLGLKYGAPLHVTDDLNTLTVATGPGVTINNTSLQTKVTGALGFDSQGN

MQLNVAGGLRIDSQNRRLILDVSYPFDAQNQLNLRLGQGPLFINSAHNLD

INYNKGLYLFTASNNSKKLEVNLSTAKGLMFDATAIAINAGDGLEFGSPN

APNTNPLKTKIGHGLEFDSNKAMVPKLGTGLSFDSTGAITVGNKNNDKLT

LWTTPAPSPNCRLNAEKDAKLTLVLTKCGSQILATVSVLAVKGSLAPISG

TVQSAHLIIRFDENGVLLNNSFLDPEYWNFRNGDLTEGTAYTNAVGFMPN

LSAYPKSHGKTAKSNIVSQVYLNGDKTKPVTLTITLNGTQETGDTT<u>EMWH</u>

<u>EGLEEASRLYFGERNVKGMFEVLEPLHAMMERGPQTLKETSFNQAYGRDL</u>

<u>MEAQEWCRKYMKSGNVKDLLQAWDLYYHVFRRISKQPSAYSMSFSWDWSG</u>

HNYINEIFATSSYTFSYIAQE

Ad34 Fiber
MTKRVRLSDSFNPVYPYEDESTSQHPFINPGFISPNGFTQSPDGVLTLKC

LTPLTTTGGSLQLKVGGGLTVDDTDGTLQENIRATAPITKNNHSVELSIG

NGLETQNNKLCAKLGNGLKFNNGDICIKDSINTLWTGINPPPNCQIVENT

NTNDGKLTLVLVKNGGLVNGYVSLVGVSDTVNQMFTQKTANIQLRLYFDS

SGNLLTDESDLKIPLKNKSSTATSETVASSKAFMPSTTAYP<u>F</u>NTTTRDSE

NYIHGICYYMTSYDRSLFPLNISIMLNSRMISSNVAYAIQFEWNLNASES

PESNIATLTTSPFFFSYITEDDN (SEQ ID NO: 60; the Fat
position 242 is shown in bold underline)

Targeting ligand sequence
EGFRVHH-GS-FKBP
MAVQLVESGGGSVQAGGSLRLTCAASGRTSRSYGMGWFRQAPGKEREFVS

GISWRGDSTGYADSVKGRFTISRDNAKNTVDLQMNSLRPEDTAIYYCAAA

AGSTWYGTLYEYDYWGQGTQVTVSSGSGSGS<u>TGVQVETISPGDGRTFPKR</u>

<u>GQTCVVHYTGMLEDGKKFDSSRDRNKPFKFMLGKQEVIRGWEEGVAQMSV</u>

<u>GQRAKLTISPDYAYGATGHPGIIPPHATLVFDVELLKL</u>
(SEQ ID NO: 33; FKBP12 sequence is underlined)

Hexon sequences
Ad5 hexon
                                       (SEQ ID NO: 34)
MATPSMMPQWSYMHISGQDASEYLSPGLVQFARATETYFSLNNKFRNPTV

APTHDVTTDRSQRLTLRFIPVDREDTAYSYKARFTLAVGDNRVLDMASTY

FDIRGVLDRGPTFKPYSGTAYNALAPKGAPNPCEWDEAATALEINLEEED

DDNEDEVDEQAEQQKTHVFGQAPYSGINITKEGIQIGVEGQTPKYADKTF

QPEPQIGESQWYETEINHAAGRVLKKTTPMKPCYGSYAKPTNENGGQGIL

VKQQNGKLESQVEMQFFSTTEATAGNGDNLTPKVVLYSEDVDIETPDTHI

SYMPTIKEGNSRELMGQQSMPNRPNYIAFRDNFIGLMYYNSTGNMGVLAG

QASQLNAVVDLQDRNTELSYQLLLDSIGDRTRYFSMWNQAVDSYDPDVRI

IENHGTEDELPNYCFPLGGVINTETLTKVKPKTGQENGWEKDATEFSDKN

EIRVGNNFAMEINLNANLWRNFLYSNIALYLPDKLKYSPSNVKISDNPNT

YDYMNKRVVAPGLVDCYINLGARWSLDYMDNVNPFNHHRNAGLRYRSMLL

GNGRYVPFHIQVPQKFFAIKNLLLLPGSYTYEWNFRKDVNMVLQSSLGND

LRVDGASIKFDSICLYATFFPMAHNTASTLEAMLRNDTNDQSFNDYLSAA

NMLYPIPANATNVPISIPSRNWAAFRGWAFTRLKTKETPSLGSGYDPYYT

YSGSIPYLDGTFYLNHTFKKVAITFDSSVSWPGNDRLLTPNEFEIKRSVD

GEGYNVAQCNMTKDWFLVQMLANYNIGYQGFYIPESYKDRMYSFFRNFQP

MSRQVVDDTKYKDYQQVGILHQHNNSGFVGYLAPTMREGQAYPANFPYPL

IGKTAVDSITQKKFLCDRTLWRIPFSSNFMSMGALTDLGQNLLYANSAHA

LDMTFEVDPMDEPTLLYVLFEVFDVVRVHRPHRGVIETVYLRTPFSAGNA

TT

Ad5 hexon E451Q
MATPSMMPQWSYMHISGQDASEYLSPGLVQFARATETYFSLNNKFRNPTV

APTHDVTTDRSQRLTLRFIPVDREDTAYSYKARFTLAVGDNRVLDMASTY

FDIRGVLDRGPTFKPYSGTAYNALAPKGAPNPCEWDEAATALEINLEEED

DDNEDEVDEQAEQQKTHVFGQAPYSGINITKEGIQIGVEGQTPKYADKTF

QPEPQIGESQWYETEINHAAGRVLKKTTPMKPCYGSYAKPTNENGGQGIL

VKQQNGKLESQVEMQFFSTTEATAGNGDNLTPKVVLYSEDVDIETPDTHI

SYMPTIKEGNSRELMGQQSMPNRPNYIAFRDNFIGLMYYNSTGNMGVLAG

QASQLNAVVDLQDRNTELSYQLLLDSIGDRTRYFSMWNQAVDSYDPDVRI

IENHGTEDELPNYCFPLGGVINTETLTKVKPKTGQENGWEKDATEFSDKN

<u>Q</u>IRVGNNFAMEINLNANLWRNFLYSNIALYLPDKLKYSPSNVKISDNPNT

YDYMNKRVVAPGLVDCYINLGARWSLDYMDNVNPFNHHRNAGLRYRSMLL

GNGRYVPFHIQVPQKFFAIKNLLLLPGSYTYEWNFRKDVNMVLQSSLGND

LRVDGASIKFDSICLYATFFPMAHNTASTLEAMLRNDTNDQSFNDYLSAA

NMLYPIPANATNVPISIPSRNWAAFRGWAFTRLKTKETPSLGSGYDPYYT

YSGSIPYLDGTFYLNHTFKKVAITFDSSVSWPGNDRLLTPNEFEIKRSVD

GEGYNVAQCNMTKDWFLVQMLANYNIGYQGFYIPESYKDRMYSFFRNFQP

MSRQVVDDTKYKDYQQVGILHQHNNSGFVGYLAPTMREGQAYPANFPYPL

IGKTAVDSITQKKFLCDRTLWRIPFSSNFMSMGALTDLGQNLLYANSAHA

LDMTFEVDPMDEPTLLYVLFEVFDVVRVHRPHRGVIETVYLRTPFSAGNA

TT (SEQ ID NO: 35; the E451Q substitution is
shown in bold underline)
```

V. Self-Cleaving Peptide Sequences

Self-cleaving peptides are peptides that induce the ribosome to skip the synthesis of a peptide bond at the C-terminus, leading to separation of the peptide sequence and a downstream polypeptide. The use of self-cleaving peptides allows for expression of multiple proteins flanking the self-cleaving peptide from a single ORF. Virally encoded 2A peptides are one type of self-cleaving peptide.

As with other self-cleaving peptides, 2A peptides function by making the ribosome skip the synthesis of a peptide bond at the C-terminus of a 2A element, leading to separation between the end of the 2A sequence and the downstream peptide (Kim et al., *PLoS One* 6(4):e18556, 2011). The "cleavage" occurs between the glycine and proline residues found on the C-terminus of the 2A peptide. Exemplary 2A peptides include, but are not limited to, the 2A peptides encoded by TaV, ERAV, PTV1 and FMDV, or modified versions thereof.

In particular examples herein, the 2A peptide comprises PTV1 2A (P2A), FMDV 2A (F2A), ERAV 2A (E2A) or TaV 2A (T2A), the sequences of which are show below and are set forth herein as SEQ ID NOs: 15-18.

```
P2A:
                                               (SEQ ID NO: 15)
ATNFSLLKQAGDVEENPGP

F2A:
                                               (SEQ ID NO: 16)
VKQTLNFDLLKLAGDVESNPGP

E2A:
                                               (SEQ ID NO: 17)
QCTNYALLKLAGDVESNPGP

T2A:
                                               (SEQ ID NO: 18)
EGRGSLLTCGDVEENPGP
```

In some examples, the 2A peptide is modified to include Gly-Ser-Gly at the N-terminus to improve cleavage efficiency. The sequences of modified P2A, F2A, E2A and T2A are shown below and are set forth herein as SEQ ID NOs: 19-22.

```
Modified P2A:
                                               (SEQ ID NO: 19)
GSGATNFSLLKQAGDVEENPGP Modified F2A:
                                               (SEQ ID NO: 20)
GSGVKQTLNFDLLKLAGDVESNPGP Modified E2A:
                                               (SEQ ID NO: 21)
GSGQCTNYALLKLAGDVESNPGP Modified T2A:
                                               (SEQ ID NO: 22)
GSGEGRGSLLTCGDVEENPGP
```

In some embodiments, the 2A polypeptide is a variant of a 2A polypeptide disclosed herein. Variants can include polypeptide sequences having at least 80%, at least 85%, at least 90%, at least 95%, at least 96%, at least 97%, at least 98%, at least 99%, or more, sequence identity to a wild-type or modified 2A polypeptide disclosed herein. Variants can include, for example, a deletion of at least one N-terminal amino acid from the 2A polypeptide of any one of SEQ ID NOs: 15, 16, 17, 18, 19, 20, 21, or 22, for example a deletion of 1, 2, 3, 4 or 5 amino acids. Variants can include a deletion of at least one C-terminal amino acid from the 2A polypeptide of any one of SEQ ID NOs: 15, 16, 17, 18, 19, 20, 21, or 22, for example a deletion of 1, 2, 3, 4 or 5 amino acids. Variants can also include, for example, at least 1, 2, 3, 4 or 5 amino acid substitutions, such as conservative amino acid substitutions.

IV. Pharmaceutical Compositions

Provided herein are compositions comprising a recombinant adenovirus or recombinant adenovirus genome disclosed herein. The compositions are, optionally, suitable for formulation and administration in vitro or in vivo. Optionally, the compositions comprise one or more of the provided agents and a pharmaceutically acceptable carrier. Suitable carriers and their formulations are described in *Remington: The Science and Practice of Pharmacy*, 22$^{nd}$ *Edition*, Loyd V. Allen et al., editors, Pharmaceutical Press (2012). Pharmaceutically acceptable carriers include materials that are not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The recombinant viruses or recombinant adenovirus genomes are administered in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, intratumoral, or inhalation routes. The administration may be local or systemic. The compositions can be administered via any of several routes of administration, including topically, orally, parenterally, intravenously, intra-articularly, intraperitoneally, intramuscularly, subcutaneously, intracavity, transdermally, intrahepatically, intracranially, intratumorally, intraosseously, nebulization/inhalation, or by installation via bronchoscopy. Thus, the compositions are administered in a number of ways depending on whether local or systemic treatment is desired, and on the area to be treated.

In some embodiments, the compositions for administration will include a recombinant adenovirus (or recombinant genome) as described herein dissolved in a pharmaceutically acceptable carrier, such as an aqueous carrier. A variety of aqueous carriers can be used, e.g., buffered saline and the like. These solutions are sterile and generally free of undesirable matter. These compositions may be sterilized. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Pharmaceutical formulations, particularly, of the recombinant viruses or recombinant adenovirus genomes can be prepared by mixing the recombinant adenovirus (or recombinant adenovirus genome) having the desired degree of purity with optional pharmaceutically acceptable carriers, excipients or stabilizers. Such formulations can be lyophilized formulations or aqueous solutions.

Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives, low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The recombinant adenovirus (or one or more nucleic acids encoding the recombinant adenovirus) can be formulated at any appropriate concentration of infectious units.

Formulations suitable for oral administration can consist of (a) liquid solutions, such as an effective amount of the recombinant adenovirus suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The recombinant adenovirus or recombinant adenovirus genome, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the provided methods, compositions can be administered, for example, by intravenous infusion, orally, topically, intraperitoneally, intravesically intratumorally, or intrathecally. Parenteral administration, intratumoral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced or infected by adenovirus or transfected with nucleic acids for ex vivo therapy can also be administered intravenously or parenterally as described above.

The pharmaceutical preparation can be in unit dosage form. In such form the preparation is subdivided into unit doses containing appropriate quantities of the active component. Thus, the pharmaceutical compositions can be administered in a variety of unit dosage forms depending upon the method of administration. For example, unit dosage forms suitable for oral administration include, but are not limited to, powder, tablets, pills, capsules and lozenges.

In some embodiments, the compositions include at least two different recombinant adenoviruses or recombinant adenovirus genomes, such as recombinant adenoviruses that bind different cellular receptors. For example, at least one of the recombinant adenoviruses in the composition could express a chimeric fiber protein. Alternatively, the recombinant adenoviruses could target different cellular receptors by encoding targeting ligand-FKBP fusion proteins in which the targeting ligand different between the viruses in the composition. In some examples, the composition includes two, three, four, five or six different recombinant adenoviruses or recombinant adenovirus genomes.

VII. Methods of Treatment

The recombinant adenovirus and recombinant adenovirus genome compositions disclosed herein can be administered for therapeutic or prophylactic treatment. In particular, provided are methods of inhibiting tumor cell viability in a subject, inhibiting tumor progression in a subject, reducing tumor volume in a subject, reduce the number of metastases in a subject, and/or treating cancer in a subject. Thus, in some examples, the methods reduce tumor cell viability, reduce tumor progression, reduce tumor volume, reduce tumor size, reduce the number of metastases, or combinations thereof, by at least 20%, at least 50%, at least 75%, at least 80%, at least 90%, at least 95%, at least 96%, at least 97%, at least 98%, at least 99%, or at least 99.5%, for example relative to no treatment (for example, before treatment with the recombinant adenovirus and recombinant adenovirus genome compositions disclosed herein).

The methods include administering a therapeutically effective amount of a recombinant adenovirus or recombinant adenovirus genome (or composition thereof) to the subject. As described throughout, the adenovirus or pharmaceutical composition is administered in any number of ways including, but not limited to, intravenously, intravascularly, intrathecally, intramuscularly, subcutaneously, intratumorally, intraperitoneally, or orally. Optionally, the method further comprising administering to the subject one or more additional therapeutic agents. In some embodiments, the therapeutic agent is a chemotherapeutic agent. In other embodiments, the therapeutic agent is an immune modulator. In yet other embodiments, the therapeutic agent is a CDK inhibitor, such as a CDK4 inhibitor.

In some embodiments, the cancer or tumor is a lung, prostate, colorectal, breast, thyroid, renal, or liver cancer or tumor, or is a type of leukemia. In some cases, the cancer is metastatic. In some examples, the tumor is a tumor of the mammary, pituitary, thyroid, or prostate gland; a tumor of the brain, liver, meninges, bone, ovary, uterus, or cervix; monocytic or myelogenous leukemia; adenocarcinoma, adenoma, astrocytoma, bladder tumor, brain tumor, Burkitt's lymphoma, breast carcinoma, cervical carcinoma, colon carcinoma, kidney carcinoma, liver carcinoma, lung carcinoma, ovarian carcinoma, pancreatic carcinoma, prostate carcinoma, rectal carcinoma, skin carcinoma, stomach carcinoma, testis carcinoma, thyroid carcinoma, chondrosarcoma, choriocarcinoma, fibroma, fibrosarcoma, glioblastoma, glioma, hepatoma, histiocytoma, leiomyoblastoma, leiomyosarcoma, lymphoma, liposarcoma cell, mammary tumor, medulloblastoma, myeloma, plasmacytoma, neuroblastoma, neuroglioma, osteogenic sarcoma, pancreatic tumor, pituitary tumor, retinoblastoma, rhabdomyosarcoma, sarcoma, testicular tumor, thymoma, or Wilms tumor. Tumors include both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects, solid tumors may be treated that arise from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, treatments may be useful in the prevention of metastases from the tumors described herein.

In therapeutic applications, recombinant adenoviruses or recombinant adenovirus genomes, or compositions thereof, are administered to a subject in a therapeutically effective amount or dose. Amounts effective for this use will depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus, the methods are applicable to both human therapy and veterinary applications.

An effective amount of an adenovirus having a modified sequence is determined on an individual basis and is based, at least in part, on the particular recombinant adenovirus used; the individual's size, age, gender; and the size and other characteristics of the proliferating cells. For example, for treatment of a human, at least $10^3$ plaque forming units (PFU) of a recombinant virus is used, such as at least $10^4$, at least $10^5$, at least $10^6$, at least $10^7$, at least $10^8$, at least $10^9$, at least $10^{10}$, at least $10^{11}$, or at least $10^{12}$ PFU, for example approximately $10^3$ to $10^{12}$ PFU of a recombinant virus is used, depending on the type, size and number of proliferating cells or neoplasms present. The effective amount can be from about 1.0 pfu/kg body weight to about $10^{15}$ pfu/kg body weight (e.g., from about $10^2$ pfu/kg body weight to about $10^{13}$ pfu/kg body weight).

A recombinant adenovirus or recombinant adenovirus genome is administered in a single dose or in multiple doses (e.g., two, three, four, six, or more doses). Multiple doses can be administered concurrently or consecutively (e.g., over a period of days or weeks).

In some embodiments, the provided methods include administering to the subject one or more additional therapeutic agents, such as an anti-cancer agent or other therapeutic treatment (such as surgical resection of the tumor). Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens), anti-angiogenesis agents and CDK inhibitors. Other anti-cancer treatments include radiation therapy and antibodies that specifically target cancer cells (such as therapeutic monoclonal antibodies).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

In some examples, the additional therapeutic agent administered is a biologic, such as a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, Zalutumumab, or combinations thereof. In some examples, the therapeutic antibody is specific for PD-1 or PDL-1 (such as an antagonistic mAb, for example Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, or MSB-0010718C).

In some examples, the additional therapeutic is a CTLA-4, LAG-3, or B7-H3 antagonist, such as Tremelimumab, BMS-986016, and MGA271, respectively.

In some examples, the additional therapeutic is an antagonist of PD-1 or PDL-1.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

CDK (Cyclin-dependent kinase) inhibitors are agents that inhibit the function of CDKs. Non-limiting examples of CDK inhibitors for use in the provided methods include AG-024322, AT7519, AZD5438, flavopiridol, indisulam, P1446A-05, PD-0332991, and P276-00 (see e.g., Lapenna et al., Nature Reviews, 8:547-566, 2009). Other CDK inhibitors include LY2835219, Palbociclib, LEE011 (Novartis), pan-CDK inhibitor AT7519, seliciclib, CYC065, butyrolactone I, hymenialdisine, SU9516, CINK4, PD0183812 or fascaplysin.

In some examples, the CDK inhibitor is a broad-range inhibitor (such as flavopiridol, olomoucine, roscovitine, kenpaullone, SNS-032, AT7519, AG-024322, (S)-Roscovitine or R547). In other examples, the CDK inhibitor is a specific inhibitor (such as fascaplysin, ryuvidine, purvalanol A, NU2058, BML-259, SU 9516, PD0332991 or P-276-00).

The choice of agent and dosage can be determined by one of skill in the art based on the given disease being treated. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

According to the methods disclosed herein, the subject is administered an effective amount of one or more of the agents provided herein. The effective amount is any amount necessary to produce a desired physiologic response (e.g., killing of a cancer cell). Therapeutic agents are typically administered at the initial dosage of about 0.001 mg/kg to about 1000 mg/kg daily. A dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the subject, the severity of the condition being treated, and the compound being employed. For example, dosages can be empirically determined considering the type and stage of cancer diagnosed in a particular subject. The dose administered to a subject, in the context of the provided methods should be sufficient to affect a beneficial therapeutic response in the patient over time. Determination of the proper dosage for a particular situation is within the skill of the practitioner. Thus, effective amounts and schedules for administering the agent may be determined empirically by one skilled in the art. The dosage should not be so large as to cause substantial adverse side effects, such as unwanted cross-reactions, anaphylactic reactions, and the like. The dosage can be adjusted by the individual physician in the event of any contraindications. Guidance can be found in the literature for appropriate dosages for given classes of pharmaceutical products.

Provided herein is a method of inhibiting tumor cell viability by contacting the tumor cell with a recombinant adenovirus or recombinant adenovirus genome, or composition thereof, as disclosed herein. In some embodiments, the method is an in vitro method. In other embodiments, the method is an in vivo method and contacting the tumor cell comprises administering the recombinant adenovirus or recombinant adenovirus genome or composition to a subject with a tumor.

Further provided is a method of inhibiting tumor progression or reducing tumor volume in a subject, by administering to the subject a therapeutically effective amount of a recombinant adenovirus or recombinant adenovirus genome (or composition thereof) disclosed herein.

Also provided is a method of treating cancer in a subject, by administering to the subject a therapeutically effective amount of a recombinant adenovirus or recombinant adenovirus genome (or composition thereof) disclosed herein.

The following examples are provided to illustrate certain particular features and/or embodiments. These examples should not be construed to limit the disclosure to the particular features or embodiments described.

EXAMPLES

Example 1: Synthetic Adenoviruses with Enhanced Replication Kinetics

This example describes synthetic adenoviruses having various modifications. Some viruses include one or more modifications in at least three E3 genes, such as deletion of three or six E3 genes, or modifications to prevent expression of three or six E3 genes, which allowed for enhanced viral replication. In some instances, the recombinant viruses include other modifications, such as liver detargeting mutations, tumor-selectivity mutations, targeting ligands, chimeric fiber proteins and/or reporter genes.

TABLE 1

Synthetic Adenovirus Descriptions

| Virus Name | SEQ ID NO: | Description | Mutations Relative to WT Ad5 |
|---|---|---|---|
| AdSyn-CO335 | 1 | Tumor-selective, liver detargeting, EGFR-targeting virus | E1A ΔLXCXE, hexon [E451Q], ΔRIDα/β/14.7K + EGFRVHH-GS-FKBP, FRB-TtoL-Fiber, ΔE4orf6/7 |
| AdSyn-CO821 | 2 | Reporter (YPet) version of ADP, AdSyn-CO335 | E1A ΔLXCXE, hexon [E451Q], YPet-P2A-ΔRIDα/β/14.7K + EGFRVHH-GS-FKBP, FRB-TtoL-Fiber, ΔE4orf6/7 |
| AdSyn-CO820 | 3 | Differs from AdSyn-CO335 by lacking three additional E3 genes | E1A ΔLXCXE, hexon [E451Q], Δ12.5k, Δ6.7k, Δ19k, ΔRIDα/β/14.7K + EGFRVHH-GS-FKBP, FRB-TtoL-Fiber, ΔE4orf6/7 |

TABLE 1-continued

Synthetic Adenovirus Descriptions

| Virus Name | SEQ ID NO: | Description | Mutations Relative to WT Ad5 |
|---|---|---|---|
| AdSyn-CO819 | 4 | Reporter (YPet) version of AdSyn-CO820 | E1A ΔLXCXE, hexon [E451Q], Δ12.5k, Δ6.7k, Δ19k, YPet-P2A-ADP, ΔRIDα/β/14.7K + EGFRVHH-GS-FKBP, FRB-TtoL-Fiber, ΔE4orf6/7 |
| AdSyn-CO1020 | 5 | Differs from AdSyn-CO820 by expression of EGFRVHH-FKBP from ADP instead of E3B | E1A[ΔLXCXE], hexon[E451Q], D12.5k, D6.7k, D19k, EGFRVHH-GS-FKBP-P2A-ADP, ΔRIDα, ΔRIDβ, D14.7k, FRB-Fiber, ΔE4-ORF6/7 |
| AdSyn-CO874 | 6 | Differs from WT Ad5 by deletion of six E3 gene and reporter YPet-P2A-ADP | Δ12.5k, Δ6.7k, Δ19k, YPet-P2A-ADP, ΔRIDα, ΔRIDβ, Δ14.7k |
| AdSyn-CO1000 | 7 | Differs from AdSyn-CO874 by containing additional tumor selective and liver detargeting mutations | E1A ΔLXCXE, hexon [E451Q], Δ6.7k, Δ12.5k, Δ19k, YPet-P2A-ADP, ΔE3-RIDα, ΔE3-RIDβ, ΔE3-14.7k, ΔE4-ORF6/7 |
| AdSyn-CO1067 | 8 | Differs from AdSyn-CO1000 by lacking the YPet reporter | E1A ΔLXCXE, hexon [E451Q], Δ6.7k, Δ12.5k, Δ19k, ΔE3-RIDα, ΔE3-RIDβ, ΔE3-14.7k, ΔE4-ORF6/7 |
| AdSyn-CO1068 | 9 | Differs from AdSyn-CO1067 by possessing a RGD-containing peptide in fiber HI loop to expand tropism | E1A ΔLXCXE, hexon [E451Q], Δ6.7k, Δ12.5k, Δ19k, ΔE3-RIDα, ΔE3-RIDβ, ΔE3-14.7k, Fiber-RGD4C, ΔE4-ORF6/7 |
| AdSyn-CO1069 | 10 | Reporter (YPet) version of AdSyn-CO1068 | E1A ΔLXCXE, hexon [E451Q], Δ6.7k, Δ12.5k, Δ19k, YPet-P2A-ADP ΔE3-RIDα, ΔE3-RIDβ, ΔE3-14.7k, Fiber-RGD4C, ΔE4-ORF6/7 |
| AdSyn-CO964 | 11 | Differs from WT Ad5 by having an Ad34 knob; also contains 14.7k-P2A-YPet reporter | Ad5: 14.7k-P2A-YPet, Fiber = Ad5 tail + Ad5 Shaft + Ad34 Knob |
| AdSyn-CO1041 | 12 | Differs from AdSyn-CO964 by possessing deletion of all six E3 genes and a different reporter (YPet-P2A-ADP) | Δ12.5k, Δ6.7k, Δ19k, YPet-P2A-ADP, ΔRIDα, ΔRIDβ, Δ14.7k, Fiber = Ad5 tail + Ad5 shaft + Ad34 knob |
| AdSyn-CO1042 | 13 | Differs from AdSyn-CO1041 by containing additional tumor selective and liver detargeting mutations | E1A ΔLXCXE, hexon[E451Q], Δ12.5k, Δ6.7k, Δ19k, YPet-P2A-ADP, ΔRID α, ΔRID β, Δ14.7k, Fiber = Ad5 tail + Ad5 shaft + Ad34 knob, ΔE4-ORF6/7 |
| AdSyn-CO1139 | 14 | Differs from AdSyn-CO1042 by lacking a reporter | E1A ΔLXCXE, hexon[E451Q], Δ12.5k, Δ6.7k, Δ19k, ΔRIDα, ΔRIDβ, Δ14.7k, Fiber = Ad5 tail + Ad5 shaft + Ad34 knob, ΔE4-ORF6/7 |
| AdSyn-CO421 | 44 | Ad5 expressing a reporter | YPet-P2A-ADP |
| AdSyn-CO1056 | 45 | A liver detargeted, tumor-selective version of AdSyn-CO964 | E1A ΔLXCXE, hexon[E451Q], YPet-P2A-ADP, Fiber = Ad5 tail + Ad5 shaft + Ad34 knob, ΔE4-ORF6/7 |
| AdSyn-CO1250 | 46 | Differs from AdSyn-CO1056 by lacking a reporter | E1A ΔLXCXE, hexon[E451Q], Fiber = Ad5 tail + Ad5 shaft + Ad34 knob, ΔE4-ORF6/7 |
| AdSyn-CO1089 | 47 | Differs from AdSyn-CO1042 by possessing a RGD-containing peptide in the putatitve Ad34 fiber knob DG loop, inserted after fiber aa512/knob aa112 | E1A ΔLXCXE, hexon[E451Q], Δ12.5k, Δ6.7k, Δ19k, YPet-P2A-ADP, ΔRIDα, ΔRIDβ, Δ14.7k, Fiber = Ad5 tail + Ad5 shaft + Ad34 knob, Fiber RGD-4C in HI loop, ΔE4-ORF6/7 |
| AdSyn-CO1320 | 48 | Differs from AdSyn-CO1000 by possessing a Katushka2S fluorophore in place of Ypet | E1A ΔLXCXE, hexon [E451Q], Δ6.7k, Δ12.5k, Δ19k, Katushka2S-P2A-ADP, ΔRIDα, ΔRIDβ, Δ14.7k, ΔE4-ORF6/7 |
| AdSyn-CO1321 | 49 | Differs from AdSyn-CO1042 by possessing a Katushka2S fluorophore in place of Ypet | E1A ΔLXCXE, hexon[E451Q], Δ12.5k, Δ6.7k, Δ19k, Katushka2S-P2A-ADP, ΔRIDα, ΔRIDβ, Δ14.7k, Fiber = Ad5 tail + Ad5 shaft + Ad34 knob, ΔE4-ORF6/7 |
| AdSyn-CO1325 | 50 | Differs from AdSyn-CO1042 by possessing human prostate specific antigen (PSA) in place of Ypet | E1A ΔLXCXE, hexon[E451Q], Δ12.5k, Δ6.7k, Δ19k, PSA-P2A-ADP, ΔRIDα, ΔRIDβ, Δ14.7k, Fiber = Ad5 tail + Ad5 shaft + Ad34 knob, ΔE4-ORF6/7 |
| AdSyn-CO1342 | 51 | Differs from AdSyn-CO1042 by possessing a firefly luciferase 2:YPet fusion protein in place of Ypet | E1A ΔLXCXE, hexon[E451Q], Δ12.5k, Δ6.7k, Δ19k, Luc2:YPet-P2A-ADP, ΔRIDα, ΔRIDβ, Δ14.7k, Fiber = Ad5 tail + Ad5 shaft + Ad34 knob, ΔE4-ORF6/7 |
| AdSyn-CO1362 | 52 | Differs from AdSyn-CO1042 by possessing a F242S point mutation in the Ad34 knob | E1A ΔLXCXE, hexon[E451Q], Δ12.5k, Δ6.7k, Δ19k, YPet-P2A-ADP, ΔRIDα, ΔRIDβ, Δ14.7k, Fiber = Ad5 tail + Ad5 shaft + Ad34 Knob [F242S], ΔE4-ORF6/7 |

TABLE 1-continued

Synthetic Adenovirus Descriptions

| Virus Name | SEQ ID NO: | Description | Mutations Relative to WT Ad5 |
|---|---|---|---|
| AdSyn-CO1403 | 53 | Differs from AdSyn-CO1042 by possessing a RGD-containing peptide in the putatitve Ad34 fiber knob HI loop, inserted after fiber aa547/knob aa147 | E1A [ΔLXCXE], Hexon E451Q; Δ12.5k, Δ6.7k, Δ19k, Ypet-P2A-ADP, ΔRIDα, ΔRIDβ, Δ14.7k; Fiber = Ad5 tail + Ad5 shaft + Ad34 knob, RGD4C-HI; ΔE4orf6/7 |
| AdSyn-CO1404 | 54 | Differs from AdSyn-001042 by possessing a RGD-containing peptide in the putatitve Ad34 fiber knob LI loop, inserted after fiber aa569/knob aa169 | E1A [ΔLXCXE], Hexon E451Q; Δ12.5k, Δ6.7k, Δ19k, Ypet-P2A-ADP, ΔRIDα, ΔRIDβ, Δ14.7k; Fiber = Ad5 tail + Ad5 shaft + Ad34 knob RGD4C-IJ; ΔE4orf6/7 |
| AdSyn-CO869 | 55 | Differs from WT Ad5 by possessing a reporter and deletion of the E3B genes | YPet-P2A-ADP, ΔRIDα, ΔRIDβ, Δ14.7k |
| AdSyn-CO996 | 56 | Similar to AdSyn-CO869 except expression of the E3B genes is abrogated by mutation of the start codons and insertion of one or more premature stop codons | YPet-P2A-ADP, RIDα[M1K], RIDβ[M1K, C30G, M60stop], 14.7k[M1K, M9stop, M31stop, M39stop] |
| AdSyn-CO999 | 57 | Tumor-selective, liver detargeted, reporter virus comprising a deletion of the E3A genes | E1A ΔLXCXE, hexon [E451Q], Δ12.5k, Δ6.7k, Δ19k, YPet-P2A-ADP, ΔE4orf6/7 |
| AdSyn-CO1002 | 58 | Differs from WT Ad5 by possessing a reporter and deletion of the E3A genes | Δ12.5k, Δ6.7k, Δ19k, YPet-P2A-ADP |
| AdSyn-CO1347 | 59 | Identical to AdSyn-CO1042 except this virus also contains a deletion of E4orf3 | E1A ΔLXCXE, hexon [E451Q], Δ12.5k, Δ6.7k, Δ19k, YPet-P2A-ADP, ΔRIDα, ΔRIDβ, Δ14.7k, Fiber = Ad5 tail + Ad5 shaft + Ad34 knob, ΔE4orf3, ΔE4orf6/7 |

Virus Descriptions:

AdSyn-CO335 (SEQ ID NO: 1) is a tumor-selective virus having the oncolytic mutations of E1A ΔLXCXE, ΔE4orf6/7, AE3-RIDα/β, AE3-14.7 k and the liver detargeting hexon mutation E451Q. This virus also expresses the rapamycin- or AP21967-dependent EGFR-targeting genes EGFRVHH-FKBP and FRB*-fiber. The generation and characterization of AdSyn-CO335 is described in WO 2016/049201, which is herein incorporated by reference in its entirety.

AdSyn-CO821 (SEQ ID NO: 2) is a modified version of AdSyn-CO335 that encodes a fluorescent reporter protein (YPet). YPet is expressed as a fusion protein with the P2A self-cleaving peptide sequence and ADP (YPet-P2A-ADP). Since this virus expresses a reporter, it can be used to determine which patients are most likely to respond to AdSyn-CO335 therapy. For example, a tumor biopsy from a cancer patient could be used to determine whether the virus can replicate in the tumor cells from the biopsy. AdSyn-CO821 could also be used to screen panels of human cancer cell lines to identify genetic mutations or gene expression profiles of tumor cells that support replication of AdSyn-CO335. These data could be used to identify a "signature" of tumors that would be likely to respond to AdSyn-CO335 therapy.

AdSyn-CO820 (SEQ ID NO: 3) is an oncolytic virus that differs from AdSyn-CO335 by deletion of three additional E3 genes (12.5 k, 6.7 k and 19 k). Thus, this virus lacks 12.5 k, 6.7 k, 19 k, RIDα, RIDβ and 14.7K.

AdSyn-CO819 (SEQ ID NO: 4) is a modified version of AdSyn-CO820 that encodes a fluorescent reporter protein (YPet). The YPet reporter is encoded as a YPet-P2A-ADP fusion protein. Like AdSyn-CO820, this virus lacks six E3 genes (12.5 k, 6.7 k, 19 k, RIDα, RIDβ, and 14.7K). AdSyn-CO819 exhibits enhanced potency and replicates faster than AdSyn-CO821 in tumor cell lines. This virus can be used to infect various cancer cell lines as well as patient derived tumor samples to define which cancer types and which patients are most likely to respond to AdSyn-CO820. Thus, AdSyn-CO819 can be used to identify which patients are likely to respond to AdSyn-CO820 therapy prior to initiation of treatment.

AdSyn-CO1020 (SEQ ID NO: 5) is a modified version of AdSyn-CO820 that expresses the EGFRVHH-FKBP fusion protein (for re-targeting to EGFR tumor cells) from the ADP ORF as an EGFRVHH-FKBP-P2A-ADP fusion.

AdSyn-CO874 (SEQ ID NO: 6) is an E3-deleted version of wild type Ad5 in which six of the E3 genes (12.5 k, 6.7 k, 19 k, RIDα, RIDβ, and 14.7K) have been deleted. AdSyn-CO874 expresses the YPet fluorescent reporter from the adenovirus ADP ORF as a YPet-P2A-ADP fusion protein. This virus exhibits enhanced potency and replicates faster than wild type Ad5 in tumor cell lines.

AdSyn-CO1000 (SEQ ID NO: 7) is a modified version of AdSyn-CO874 that also contains the hexon E451Q mutation that detargets the virus from the liver (to allow intravenous delivery), and has the E1A LXCXE and E4orf6/7 deletions that confer tumor selective replication. This virus also encodes the YPet reporter as a YPet-P2A-ADP fusion protein. AdSyn-CO1000 exhibits a very high rate of replication.

AdSyn-CO1067 (SEQ ID NO: 8) is a version of AdSyn-CO1000 that does not contain the YPet reporter. This virus is a therapeutic candidate.

AdSyn-CO1068 (SEQ ID NO: 9) differs from AdSyn-CO1067 by having an RGD-containing peptide in the fiber HI loop. This modification expands tropism by allowing the virus to utilize RGD-integrin interactions as an alternative infection pathway.

AdSyn-CO1069 (SEQ ID NO: 10) is identical to AdSyn-CO1068 except that it encodes the YPet reporter as a YPet-P2A-ADP fusion protein.

AdSyn-CO964 (SEQ ID NO: 11) is a modified Ad5 virus in which the Ad5 fiber knob has been replaced with the Ad34 fiber knob. This virus also expresses the YPet reporter as a YPet-P2A-ADP fusion protein. AdSyn-CO964 exhibits enhanced replication relative to WT Ad5 and AdSyn-CO335 in multiple cell lines tested, particularly those with low or no coxsackie adenovirus receptor (CAR). This may be due to the fact that the Ad34 knob binds to CD46, which is expressed on all nucleated cells, and therefore allows the virus to enter cells that do not express CAR.

AdSyn-CO1041 (SEQ ID NO: 12) also encodes a chimeric Ad5/Ad34 fiber, but differs from AdSyn-CO964 by deletion of six E3 genes (12.5 k, 6.7 k, 19 k, RIDα, RIDβ and 14.7K). AdSyn-CO1041 also includes the YPet reporter expressed as a YPet-P2A-ADP fusion protein.

AdSyn-CO1042 (SEQ ID NO: 13) is a liver detargeted, tumor-selective version of AdSyn-CO1041. Specifically, AdSyn-CO1042 includes the oncolytic mutations of E1A ΔLXCXE and ΔE4orf6/7, and the liver detargeting hexon mutation E451Q. AdSyn-CO1042 also includes the YPet reporter expressed as a YPet-P2A-ADP fusion protein. This virus exhibits potent replication in a variety of cell lines that do not express CAR and is much more potent than WT Ad5. The combination of the Ad34 knob and the deletion of specific E3 genes results in a virus with enhanced potency across a broad spectrum of cancer cell lines.

AdSyn-CO1139 (SEQ ID NO: 14) is identical to AdSyn-CO1142 except that it does not contain a reporter gene. Thus, AdSyn-CO1139 is a therapeutic version of AdSyn-CO1142.

AdSyn-CO421 (SEQ ID NO: 44) is a WT Ad5 that expresses the YPet reporter as a YPet-P2A-ADP fusion protein. This virus is used a control in the studies described herein.

AdSyn-CO1056 (SEQ ID NO: 45) is a liver detargeted, tumor-selective version of AdSyn-CO964. Specifically, AdSyn-CO1056 includes the oncolytic mutations of E1A ΔLXCXE and ΔE4orf6/7, and the liver detargeting hexon mutation E451Q. AdSyn-CO1056 is a modified Ad5 virus in which the Ad5 fiber knob has been replaced with the Ad34 fiber knob. It also includes the YPet reporter expressed as a YPet-P2A-ADP fusion protein.

AdSyn-CO1250 (SEQ ID NO: 46) is a non-reporter version of AdSyn-CO1056. This virus is a therapeutic candidate.

AdSyn-CO1089 (SEQ ID NO: 47) differs from AdSyn-CO1042 by having an RGD-containing peptide (RGD4C) in the putative Ad34 fiber DG loop. RGD4C is inserted following fiber amino acid 512 (corresponding to knob amino acid 112). This modification expands tropism by allowing the virus to utilize RGD-integrin interactions as an alternative infection pathway.

AdSyn-CO1320 (SEQ ID NO: 48) is identical to AdSyn-CO1000 except that the YPet fluorophore in AdSyn-CO1000 is replaced with a Katushka2S fluorophore.

AdSyn-CO1321 (SEQ ID NO: 49) is identical to AdSyn-CO1042 except that the YPet fluorophore in AdSyn-CO1042 is replaced with a Katushka2S fluorophore.

AdSyn-CO1325 (SEQ ID NO: 50) is a liver detargeted (hexon E451Q), tumor-selective adenovirus comprising a chimeric Ad5/Ad34 fiber, a deletion of six E3 genes (12.5 k, 6.7 k, 19 k, RIDα, RIDβ and 14.7K), the oncolytic mutations of E1A ΔLXCXE and ΔE4orf6/7. AdSyn-CO1325 also expresses human prostate specific antigen (PSA) as a PSA-P2A-ADP fusion protein. This virus is identical to AdSyn-CO1042 except that the YPet fluorophore in AdSyn-CO1042 is replaced with PSA.

AdSyn-CO1342 (SEQ ID NO: 51) is a liver detargeted, tumor-selective adenovirus encoding a chimeric Ad5/Ad34 fiber and comprising a deletion of six E3 genes (12.5 k, 6.7 k, 19 k, RIDα, RIDβ and 14.7K). AdSyn-CO1342 also encodes the oncolytic mutations of E1A ΔLXCXE and ΔE4orf6/7, the liver detargeting hexon mutation E451Q and a Luc2:YPet reporter expressed as a Luc2:YPet-P2A-ADP fusion protein. This virus is identical to AdSyn-CO1042 except that the YPet fluorophore in AdSyn-CO1042 is replaced with a firefly luciferase 2:YPet fusion protein.

AdSyn-CO1362 (SEQ ID NO: 52) is a liver detargeted, tumor-selective adenovirus encoding a chimeric Ad5/Ad34 fiber protein with a F242F mutation, and comprising a deletion of six E3 genes (12.5 k, 6.7 k, 19 k, RIDα, RIDβ and 14.7K). AdSyn-CO1362 includes the oncolytic mutations of E1A ΔLXCXE and ΔE4orf6/7, and the liver detargeting hexon mutation E451Q. This virus also includes the YPet reporter expressed as a YPet-P2A-ADP fusion protein. AdSyn-CO1362 is nearly identical to AdSyn-CO1042 but differs by having a point mutation (F242S) in the Ad34 knob domain that abrogates binding to CD46.

AdSyn-CO1403 (SEQ ID NO: 53) differs from AdSyn-CO1042 by having an RGD-containing peptide (RGD4C) in the putative Ad34 fiber HI loop. RGD4C is inserted following fiber amino acid 547 (corresponding to knob amino acid 147). This modification expands tropism by allowing the virus to utilize RGD-integrin interactions as an alternative infection pathway.

AdSyn-CO1404 (SEQ ID NO: 54) differs from AdSyn-CO1042 by having an RGD-containing peptide (RGD4C) in the putative Ad34 fiber IJ loop. RGD4C is inserted following fiber amino acid 569 (corresponding to knob amino acid 169). This modification expands tropism by allowing the virus to utilize RGD-integrin interactions as an alternative infection pathway.

AdSyn-CO869 (SEQ ID NO: 55) differs from WT Ad5 by possessing a YPet-P2A-ADP reporter and deletion of the E3B genes (ΔRIDα, ΔRIDβ, Δ14.7 k).

AdSyn-CO996 (SEQ ID NO: 56) differs from WT Ad5 by possessing a YPet-P2A-ADP reporter and abrogation of expression of the E3B genes. Expression of RIDα, RIDβ and 14.7 k is abrogated by mutation of the start codons for each gene and insertion of one or more premature stop codons.

AdSyn-CO999 (SEQ ID NO: 57) differs from WT Ad5 by possessing tumor-selectivity mutations (E1A ΔLXCXE and ΔE4orf6/7), a liver detargeting mutation (hexon[E451Q]) and deletion of the E3A genes (Δ12.5 k, Δ6.7 k, Δ19 k). This virus also possesses a YPet-P2A-ADP reporter.

AdSyn-CO1002 (SEQ ID NO: 58) differs from WT Ad5 by possession a reporter (YPet-P2A-ADP) and deletion of the E3A genes (Δ12.5 k, Δ6.7 k, Δ19 k).

AdSyn-CO1347 (SEQ ID NO: 59) is a liver-detargeted, tumor-selective virus having a chimeric Ad5/Ad34 fiber, a deletion of E3 genes 12.5 k, 6.7 k, 19 k, RIDα, RIDβ and 14.7K, a deletion of E4orf3, and a YPet reporter expressed as a YPet-P2A-ADP fusion protein. This virus is identical to AdSyn-CO1042 except that this virus further includes the E4orf3 deletion. Studies described herein indicate that deletion of E4orf3 does not negatively impact virus replication in tumor cells.

Example 2: Replication Kinetics of E3-Deleted Adenoviruses

Replication kinetics of the recombinant adenoviruses described in Example 1 were determined using a fluorescence-based viral kinetic (FBVK) assay, as disclosed in PCT Publication No. WO 2017/147265 (incorporated herein by reference in its entirety). Briefly, the FBVK assay can be used to determine the kinetics of adenoviruses that encode a fluorescent reporter (typically YPet), which is expressed upon infection. A measurement of fluorescence intensity provides a reading proportional to the number of infected cells over a period of several virus lifecycles. A semi-log plot of the exponential growth in infected cells versus time yields a straight line proportional to the exponential growth rate or replication rate. The replication rate of each virus in a particular cell line is reported as "ln slope." A higher ln slope indicates a faster rate of replication.

Replication of AdSyn-CO421, AdSyn-CO819, AdSyn-CO821, AdSyn-CO874, AdSyn-CO1000, AdSyn-CO1041 and AdSyn-CO1042 was tested using the FBVK assay in multiple different types of cancer cell lines and in normal small airway epithelial cells (SAEC). The rate of replication was determined for each virus (units=1/days). The results demonstrated that viruses lacking six E3 genes replicated faster than counterpart viruses that do not lack these genes.

FIGS. 1-4 show direct comparisons of replication kinetics of particular synthetic adenoviruses, as discussed below.

To test the replication effect of deleting six E3 genes (all E3 genes except ADP), replication of AdSyn-CO421 (WT Ad5) was compared with AdSyn-CO874 in A549 cells. As shown in FIG. 1, the ln slope of AdSyn-CO874 was greater than the ln slope of AdSyn-CO421, indicating that deletion of the E3 gene enhances replication. Similar results were found in multiple different cancer cells lines.

Figure 2:
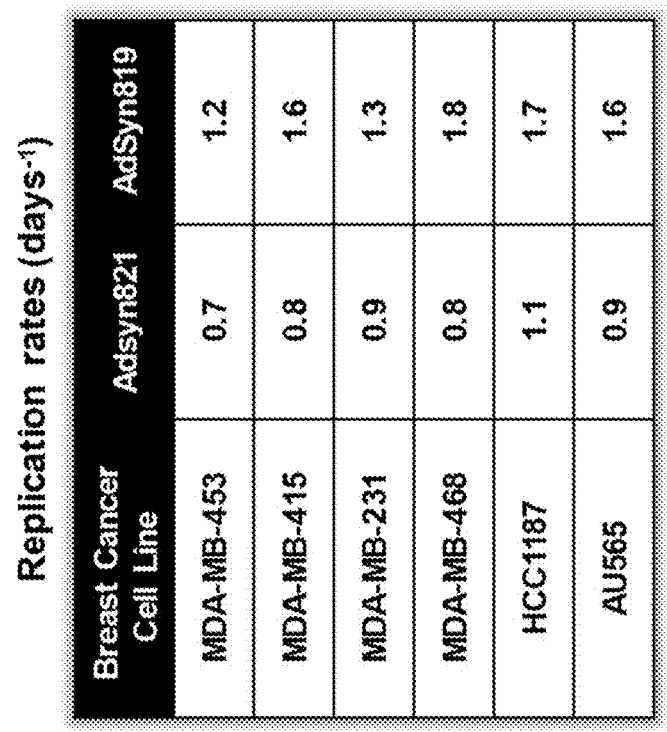
FIG. 2 is a pair of graphs and a table comparing replication kinetics of oncolytic virus AdSyn-CO821 (lacking E3 genes RIDα, RIDβ and 14.7 k) with corresponding virus AdSyn-CO819 lacking six E3 genes (RIDα, RIDβ, 4.7 k, 12.5 k, 6.7 k and 19.k). AdSyn-CO819 exhibited superior replication in all cancer cell lines tested.
Figure 2:
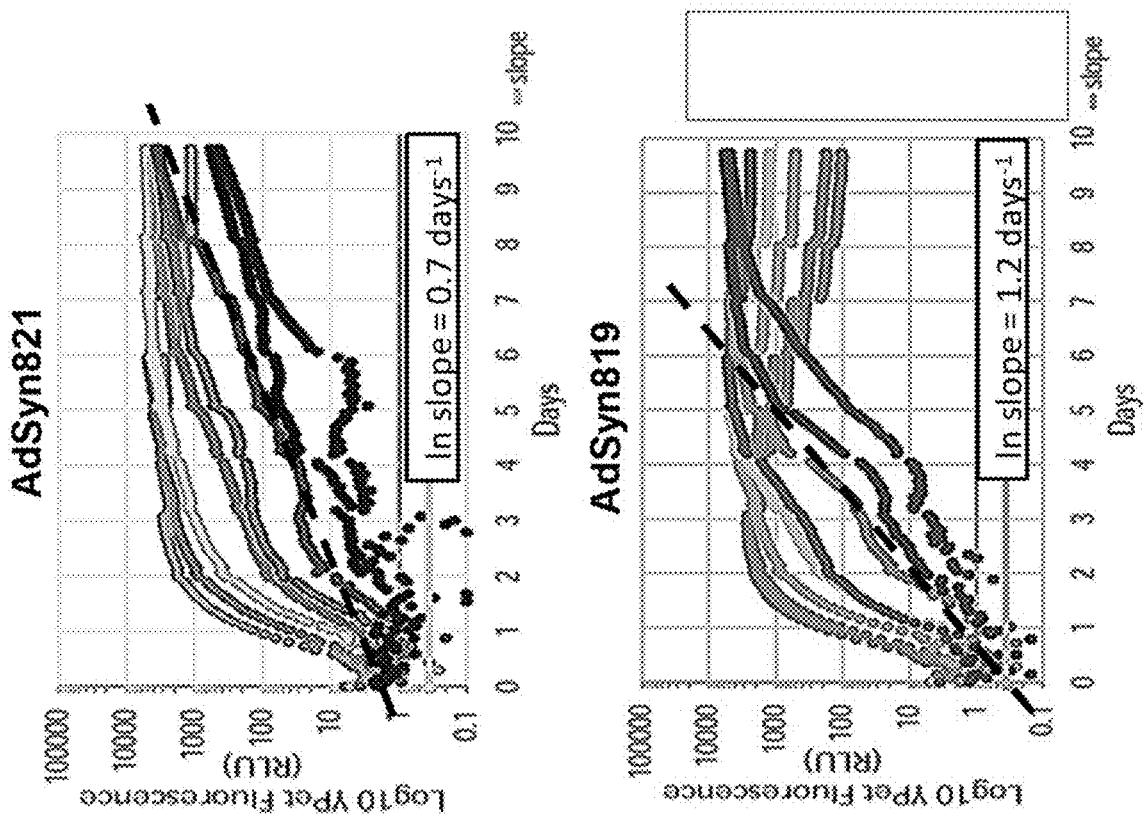

In another study, replication of AdSyn-CO821 was compared with AdSyn-CO819 in MDA-MB-453 breast cancer cells. AdSyn-CO821 is a liver-detargeted oncolytic virus lacking three E3 genes (RIDα, RIDβ and 14.7K). AdSyn-CO819 contains the same mutations as AdSyn-CO821 but has a deletion of six E3 genes (12.5 k, 6.7 k, 19 k, RIDα, RIDβ, and 14.7K). As shown in FIG. 2, deletion of the additional three E3 genes led to enhanced replication. Similar results were found in multiple other cancer cells lines.

Figure 3:
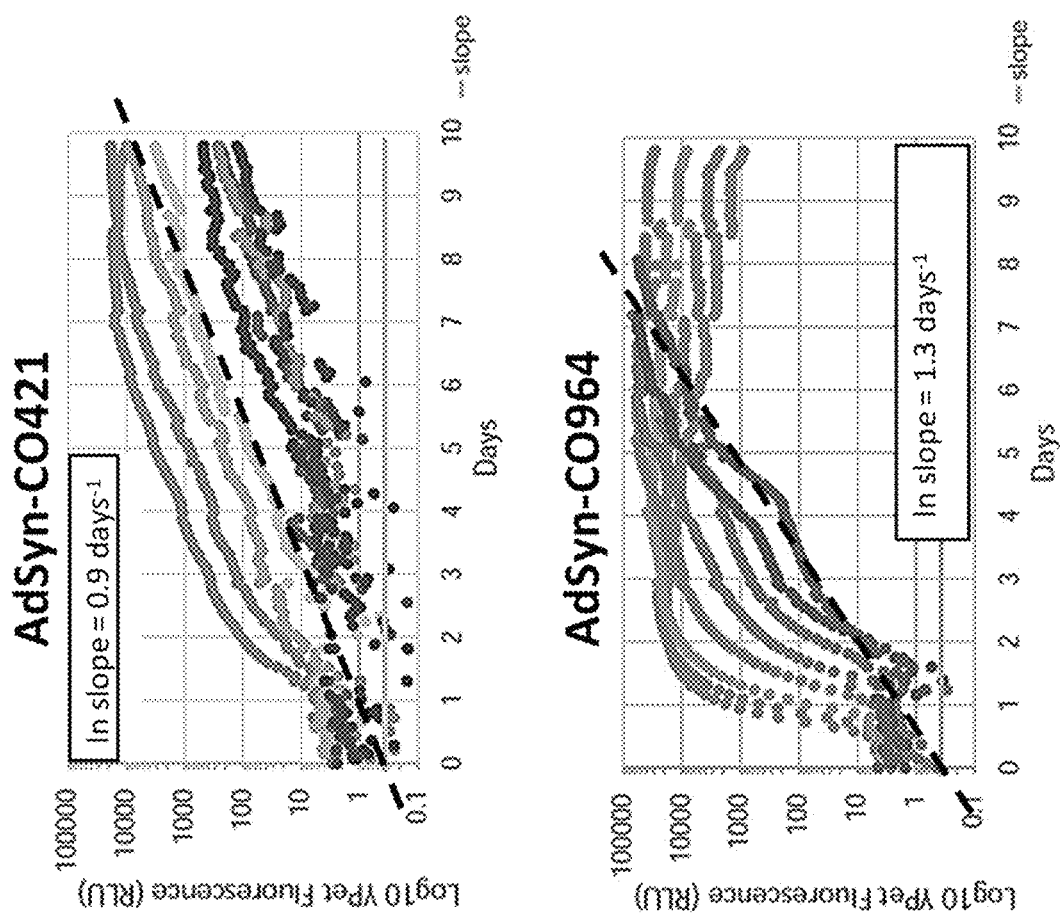
FIG. 3 is a pair of graphs showing replication kinetics of WT Ad5 reporter virus AdSyn-CO421 with AdSyn-CO964 in coxsackie adenovirus receptor (CAR)-negative cells. AdSyn-CO964 is a synthetic Ad5 virus that expresses a chimeric fiber protein comprised of an Ad5 shaft and an Ad34 knob. Expression of the Ad34 knob domain led to enhanced virus replication in CAR-negative cells.

AdSyn-CO964 is an Ad5 reporter expressing virus expressing a chimeric fiber protein (Ad5 fiber shaft and Ad34 fiber knob). Replication of this virus was tested in a CAR-negative cell line (HS578T). AdSyn-CO421 was used as a control. As shown in FIG. 3, AdSyn-CO964 exhibits enhanced replication in CAR-negative cells compared to a control virus having an Ad5 knob domain.

Figure 4:
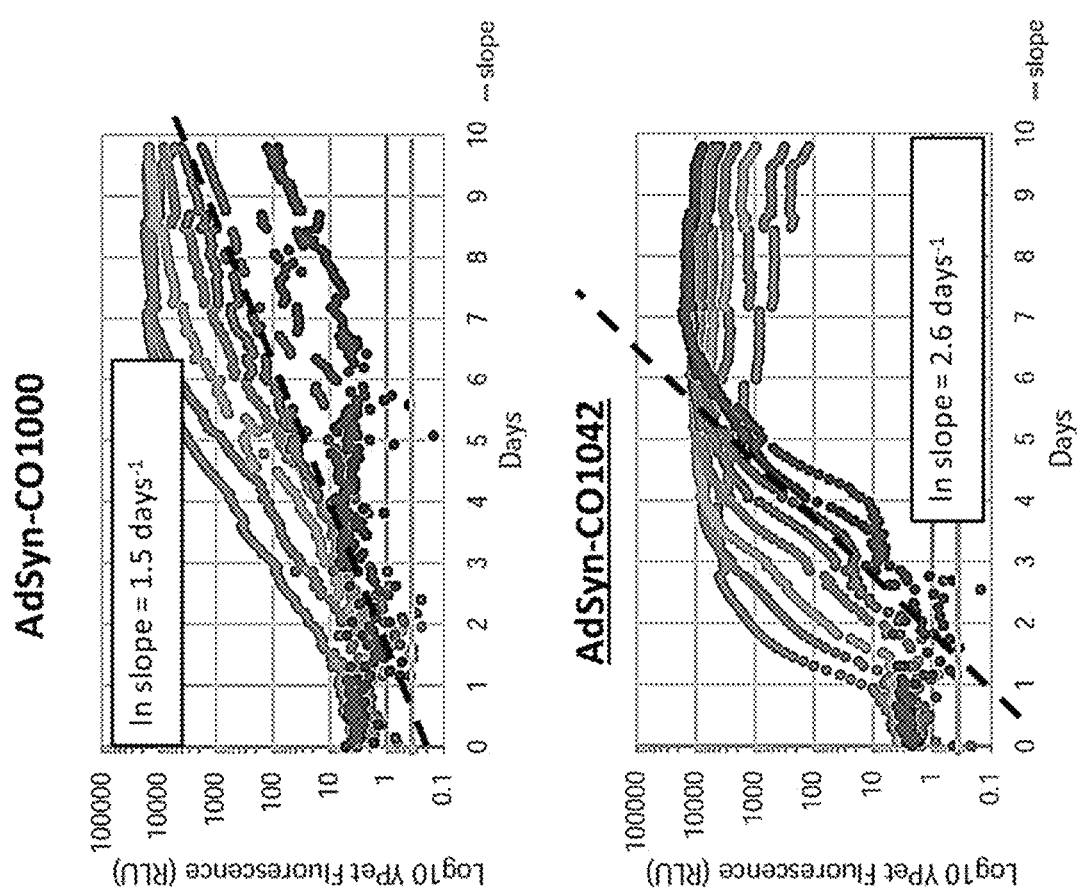
FIG. 4 is a pair of graphs comparing replication of an E3-deleted oncolytic Ad5 (AdSyn-CO1000) with a corresponding E3-deleted oncolytic virus expressing the Ad34 knob domain (AdSyn-CO1042) in CAR-negative cells. AdSyn-CO1042 exhibited enhanced replication kinetics compared with the Ad5 knob expressing virus in multiple cell lines.

Next, replication of a liver-detargeted, tumor-selective reporter virus lacking six E3 genes (AdSyn-CO1000) was compared with a virus (AdSyn-CO1042) having the same mutations, but additionally expressing a chimeric fiber protein (Ad5 shaft and Ad34 knob). Replication of these viruses was tested in CAR-negative cell line HS578T. The results demonstrate that replication in CAR-negative cells is enhanced when the virus expresses a fiber protein with an Ad34 knob domain (FIG. 4).

Example 3: Replication Rate of Recombinant Oncolytic Adenoviruses in a Panel of Tumor Cell Lines Recombinant adenoviruses AdSyn-CO421, AdSyn-CO819, AdSyn-CO821, AdSyn-CO874, AdSyn-CO964, AdSyn-CO1000, AdSyn-CO1041, AdSyn-CO1042, AdSyn-CO1056, AdSyn-CO1069, AdSyn-CO1089, AdSyn-CO1362, AdSyn-CO1320, AdSyn-CO1321 and AdSyn-CO1342 were assessed for their rate of replication using the fluorescence-based viral kinetics (FBVK) assay in a variety of brain, breast, colon, head and neck, lung, prostate and skin cancer cell lines. The data are shown in Tables 2A and 2B.

TABLE 2A

Rate of replication of eight recombinant adenoviruses (1/days)

| Cell Line | Tumor tissue | AdSyn-CO421 | AdSyn-CO819 | AdSyn-CO821 | AdSyn-CO874 | AdSyn-CO964 | AdSyn-CO1000 | AdSyn-CO1041 | AdSyn-CO1042 |
|---|---|---|---|---|---|---|---|---|---|
| H4 | brain | 1.55 | 2.49 | 1.59 | 3.24 | 1.46 | 2.95 | 4.76 | 4.26 |
| U118-MG | brain | 0.97 | 0.85 | 0.39 | 1.28 | 0.76 | 0.95 | 2.05 | 2.16 |
| U87-MG | brain | 1.41 | 1.09 | 0.73 | 1.85 | 1.26 | 1.68 | 2.52 | 2.42 |
| AU565 | breast | 1.21 | 1.67 | 0.92 | 2.22 | 1.42 | 2.46 | 2.61 | 2.22 |
| BT-20 | breast | 0.76 | 0.78 | 0.48 | 1.12 | 1.10 | 1.27 | 2.47 | 2.38 |
| BT474 | breast | 2.07 | 1.47 | 1.45 | 2.11 | 1.58 | 1.79 | 1.58 | 1.47 |
| BT549 | breast | 0.87 | 1.33 | 0.00 | 1.49 | ND | 1.96 | 2.27 | 2.38 |
| CAMA-1 | breast | 1.66 | 1.61 | 1.26 | 2.09 | 1.20 | 1.83 | 2.42 | 1.99 |
| HCC1187 | breast | 0.84 | 2.11 | 1.41 | 2.62 | 1.21 | 2.84 | 2.93 | 2.45 |
| HCC1428 | breast | 0.55 | 0.78 | 0.42 | 0.97 | 1.27 | 0.96 | 1.88 | 1.81 |
| HCC1500 | breast | 1.62 | 1.41 | 1.13 | 2.22 | 1.75 | 1.62 | 2.94 | 2.40 |
| HCC1569 | breast | 0.61 | 0.80 | 1.10 | 0.77 | 1.24 | 0.80 | 1.11 | 1.36 |
| HCC1806 | breast | 0.11 | 0.84 | 0.00 | 1.35 | ND | 1.03 | 1.95 | 1.66 |
| HCC1954 | breast | 1.28 | 1.50 | 1.04 | 2.23 | 1.52 | 2.00 | ND | ND |
| HCC202 | breast | 1.47 | 1.29 | 1.02 | ND | ND | 1.56 | 2.38 | 1.89 |
| HCC2935 | breast | 1.19 | 0.99 | 0.85 | 1.64 | 1.70 | 1.47 | 1.96 | 2.01 |
| HCC38 | breast | 2.17 | 1.90 | 1.71 | 2.49 | 1.39 | 2.36 | 2.55 | 2.22 |
| HCC70 | breast | 1.07 | 1.47 | 1.01 | 2.06 | 1.85 | 1.76 | 2.68 | 2.59 |
| HS578T | breast | 0.85 | 1.25 | 0.74 | 1.55 | 1.38 | 1.44 | 2.92 | 2.45 |
| MCF-7 | breast | 1.27 | 1.19 | 0.69 | 1.62 | 1.18 | 1.52 | 2.43 | 1.97 |
| MDA-MB-157 | breast | 0.00 | 0.80 | 0.00 | 0.42 | 1.18 | 1.00 | 1.26 | 1.58 |
| MDA-MB-175VII | breast | 1.17 | 0.48 | 0.60 | 1.35 | 1.05 | 0.84 | 1.96 | 1.33 |
| MDA-MB-231 | breast | 1.08 | 1.35 | 0.80 | 1.71 | 1.27 | 1.51 | 2.25 | 2.01 |

TABLE 2A-continued

Rate of replication of eight recombinant adenoviruses (1/days)

| Cell Line | Tumor tissue | AdSyn-CO421 | AdSyn-CO819 | AdSyn-CO821 | AdSyn-CO874 | AdSyn-CO964 | AdSyn-CO1000 | AdSyn-CO1041 | AdSyn-CO1042 |
|---|---|---|---|---|---|---|---|---|---|
| MDA-MB-361 | breast | 1.71 | 1.42 | 1.28 | 2.22 | 1.37 | 2.11 | 2.22 | 2.02 |
| MDA-MB-415 | breast | 1.42 | 1.75 | 0.87 | 2.91 | 1.61 | 2.24 | 4.00 | 3.29 |
| MDA-MB-453 | breast | 1.24 | 1.47 | 1.00 | 1.88 | 1.36 | 1.74 | 2.41 | 1.82 |
| MDA-MB-468 | breast | 0.83 | 1.88 | 0.38 | 2.50 | 0.94 | 3.24 | 2.70 | 2.62 |
| T47D | breast | 1.08 | 1.65 | 0.00 | 1.62 | 0.68 | 1.64 | 1.38 | 1.90 |
| UACC812 | breast | 0.94 | 0.76 | 0.53 | 1.17 | 1.15 | 0.78 | 2.16 | 1.43 |
| ZR-75-30 | breast | 1.75 | 1.45 | 1.20 | ND | ND | 1.70 | 2.04 | 1.90 |
| Colo205 | colon | 0.99 | 1.22 | 0.00 | 1.68 | ND | 1.34 | 3.15 | 2.61 |
| Detroit562 | head and neck | 0.72 | 1.30 | 0.41 | 1.77 | 1.11 | 1.75 | 2.18 | 2.13 |
| FaDu | head and neck | 0.80 | 0.58 | 0.31 | 1.01 | 0.87 | 0.87 | 3.51 | 2.51 |
| SCC47 | head and neck | 0.77 | 1.09 | 0.50 | 1.70 | 1.12 | 1.32 | 2.67 | 2.23 |
| UMSCC17B | head and neck | 0.00 | 0.25 | 0.00 | 0.78 | 1.02 | 0.40 | 1.10 | 0.80 |
| UMSCC47 | head and neck | 0.64 | 0.95 | 0.35 | 1.47 | 0.46 | 1.24 | 1.96 | 1.73 |
| Cal27 | head and neck | 0.60 | 1.20 | 0.46 | 1.79 | 0.90 | 1.77 | 2.76 | 3.66 |
| Cal33 | head and neck | 1.18 | 1.66 | 1.18 | 2.31 | 1.40 | 2.40 | 3.59 | 3.41 |
| A549 | lung | 1.98 | 2.43 | 1.77 | 2.66 | 1.44 | 2.69 | 3.08 | 2.96 |
| H69AR | lung | 0.92 | 1.71 | 0.64 | ND | ND | 2.45 | 2.89 | 2.63 |
| NCI H1299 | lung | 1.50 | 1.99 | 1.25 | 2.06 | 1.12 | 1.88 | 1.96 | 1.98 |
| NCI H1395 | lung | 1.67 | 1.28 | 1.09 | 1.71 | 1.56 | 1.59 | 1.98 | 2.00 |
| NCI H1417 | lung | 1.21 | 1.13 | 0.69 | 1.16 | 1.36 | 1.64 | ND | ND |
| NCI H1437 | lung | 0.35 | 0.94 | 0.67 | ND | ND | 1.04 | 2.62 | 2.24 |
| NCI H146 | lung | 1.39 | ND | ND | 1.62 | ND | 1.82 | 1.80 | 1.99 |
| NCI H1563 | lung | 1.28 | 1.04 | 0.82 | 1.38 | 1.26 | 1.66 | 1.85 | 1.58 |
| NCI H1573 | lung | 1.16 | 1.23 | 1.03 | 2.01 | 1.40 | 1.66 | 2.50 | 1.93 |
| NCI H1688 | lung | 0.86 | 1.00 | 0.75 | 1.04 | 2.06 | 0.96 | 3.13 | 2.70 |
| NCI H1975 | lung | 0.64 | 1.80 | 0.77 | 1.83 | 1.35 | 2.19 | 3.01 | 2.42 |
| NCI H446 | lung | 0.89 | 1.39 | 0.81 | ND | ND | 1.65 | 1.94 | 1.61 |
| NCI H526 | lung | 0.89 | ND | ND | 1.55 | ND | 1.28 | 1.51 | 1.45 |
| NCI H596 | lung | 0.26 | 0.75 | 0.13 | 1.03 | 1.09 | 1.01 | 1.83 | 1.77 |
| NCI H661 | lung | 2.78 | 2.25 | 2.57 | ND | ND | 2.44 | 2.84 | 2.45 |
| NCI H82 | lung | 0.91 | 1.53 | 0.59 | ND | ND | 1.54 | 1.70 | 1.74 |
| SW1271 | lung | 1.77 | 1.80 | 1.57 | ND | ND | 1.84 | 2.19 | 2.06 |
| PC-3 | prostate | 0.00 | 0.86 | 0.86 | 0.76 | 0.64 | 0.85 | 2.13 | 2.36 |
| A431 | skin | 0.40 | 0.93 | 0.39 | 1.26 | ND | 1.01 | 2.08 | 1.96 |

ND = not done

TABLE 2B

Rate of replication of seven recombinant adenoviruses (1/days)

| Cell Line | Tumor tissue | AdSyn-CO1056 | AdSyn-CO1069 | AdSyn-CO1089 | AdSyn-CO1362 | AdSyn-CO1320 | AdSyn-CO1321 | AdSyn-CO1342 |
|---|---|---|---|---|---|---|---|---|
| H4 | brain | ND | ND | ND | ND | ND | ND | ND |
| U118-MG | brain | 1.12 | 1.91 | 2.43 | ND | ND | ND | ND |
| U87-MG | brain | 0.87 | 2.62 | 2.74 | ND | ND | ND | ND |
| AU565 | breast | ND | ND | ND | ND | ND | ND | ND |
| BT-20 | breast | ND | ND | 2.64 | ND | ND | ND | ND |
| BT474 | breast | 1.28 | 1.81 | 1.78 | ND | ND | ND | ND |
| BT549 | breast | 0.86 | 2.12 | 2.61 | ND | ND | ND | ND |
| CAMA-1 | breast | ND | ND | ND | ND | ND | ND | ND |
| HCC1187 | breast | ND | ND | ND | ND | ND | ND | ND |
| HCC1428 | breast | ND | ND | ND | 1.66 | ND | ND | ND |
| HCC1500 | breast | 0.91 | 1.66 | 1.73 | ND | ND | ND | ND |
| HCC1569 | breast | ND | ND | ND | ND | ND | ND | ND |
| HCC1806 | breast | 0.51 | 1.19 | 1.59 | ND | ND | ND | ND |
| HCC1954 | breast | ND | ND | ND | ND | ND | ND | ND |
| HCC202 | breast | ND | ND | 1.75 | ND | ND | ND | ND |
| HCC2935 | breast | ND | ND | ND | ND | ND | ND | ND |
| HCC38 | breast | ND | ND | ND | ND | ND | ND | ND |
| HCC70 | breast | ND | ND | ND | ND | ND | ND | ND |

TABLE 2B-continued

| Cell Line | Tumor tissue | AdSyn-CO1056 | AdSyn-CO1069 | AdSyn-CO1089 | AdSyn-CO1362 | AdSyn-CO1320 | AdSyn-CO1321 | AdSyn-CO1342 |
|---|---|---|---|---|---|---|---|---|
| HS578T | breast | 1.08 | 2.38 | 2.38 | ND | ND | ND | 2.57 |
| MCF-7 | breast | 1.27 | 1.54 | 2.23 | ND | ND | ND | ND |
| MDA-MB-157 | breast | ND | ND | ND | ND | ND | ND | ND |
| MDA-MB-175VII | breast | ND | ND | ND | ND | ND | ND | ND |
| MDA-MB-231 | breast | 1.00 | 1.57 | 2.03 | ND | ND | ND | ND |
| MDA-MB-361 | breast | ND | ND | ND | ND | ND | ND | ND |
| MDA-MB-415 | breast | ND | ND | ND | ND | ND | ND | ND |
| MDA-MB-453 | breast | ND | ND | ND | ND | ND | ND | ND |
| MDA-MB-468 | breast | 0.83 | 2.84 | 2.98 | ND | ND | ND | ND |
| T47D | breast | 1.79 | 1.72 | 1.53 | 1.57 | ND | ND | ND |
| UACC812 | breast | ND | ND | ND | 1.47 | ND | ND | ND |
| ZR-75-30 | breast | ND | ND | 1.57 | ND | ND | ND | ND |
| Colo205 | colon | 1.05 | 1.75 | 2.61 | ND | ND | ND | ND |
| Detroit562 | head and neck | ND | ND | ND | ND | ND | ND | ND |
| FaDu | head and neck | ND | ND | ND | ND | ND | ND | ND |
| SCC47 | head and neck | ND | ND | ND | ND | ND | ND | ND |
| UMSCC17B | head and neck | ND | ND | ND | ND | ND | ND | ND |
| UMSCC47 | head and neck | ND | ND | ND | ND | ND | ND | ND |
| Cal27 | head and neck | ND | ND | ND | ND | ND | ND | ND |
| Cal33 | head and neck | ND | ND | ND | ND | ND | ND | ND |
| A549 | lung | 1.28 | 2.74 | 2.79 | 2.76 | 3.00 | 3.11 | 2.63 |
| H69AR | lung | ND | ND | 2.40 | ND | ND | ND | ND |
| NCI H1299 | lung | ND | ND | ND | ND | ND | ND | ND |
| NCI H1395 | lung | ND | ND | ND | ND | ND | ND | ND |
| NCI H1417 | lung | ND | ND | ND | ND | ND | ND | ND |
| NCI H1437 | lung | ND | ND | 2.19 | ND | ND | ND | ND |
| NCI H146 | lung | ND | 2.04 | ND | 1.87 | ND | ND | ND |
| NCI H1563 | lung | ND | ND | 1.63 | ND | ND | ND | ND |
| NCI H1573 | lung | ND | ND | ND | ND | ND | ND | ND |
| NCI H1688 | lung | ND | ND | ND | ND | ND | ND | ND |
| NCI H1975 | lung | 1.03 | 2.16 | 2.95 | ND | ND | ND | ND |
| NCI H446 | lung | ND | ND | 1.65 | 1.57 | ND | ND | ND |
| NCI H526 | lung | ND | 1.39 | ND | ND | ND | ND | ND |
| NCI H596 | lung | ND | ND | 1.78 | 1.03 | ND | ND | ND |
| NCI H661 | lung | ND | ND | 2.57 | ND | ND | ND | ND |
| NCI H82 | lung | ND | ND | 1.38 | ND | ND | ND | ND |
| SW1271 | lung | ND | ND | 2.07 | ND | ND | ND | ND |
| PC-3 | prostate | ND | ND | ND | ND | ND | ND | ND |
| A431 | skin | 0.92 | 1.32 | 1.71 | ND | ND | ND | ND |

ND = not done

Example 4: In Vivo Characterization of AdSyn-CO1042 and AdSyn-CO1000

Additional studies were performed to further characterize recombinant adenoviruses that exhibited enhanced virus replication.

Figure 5A:
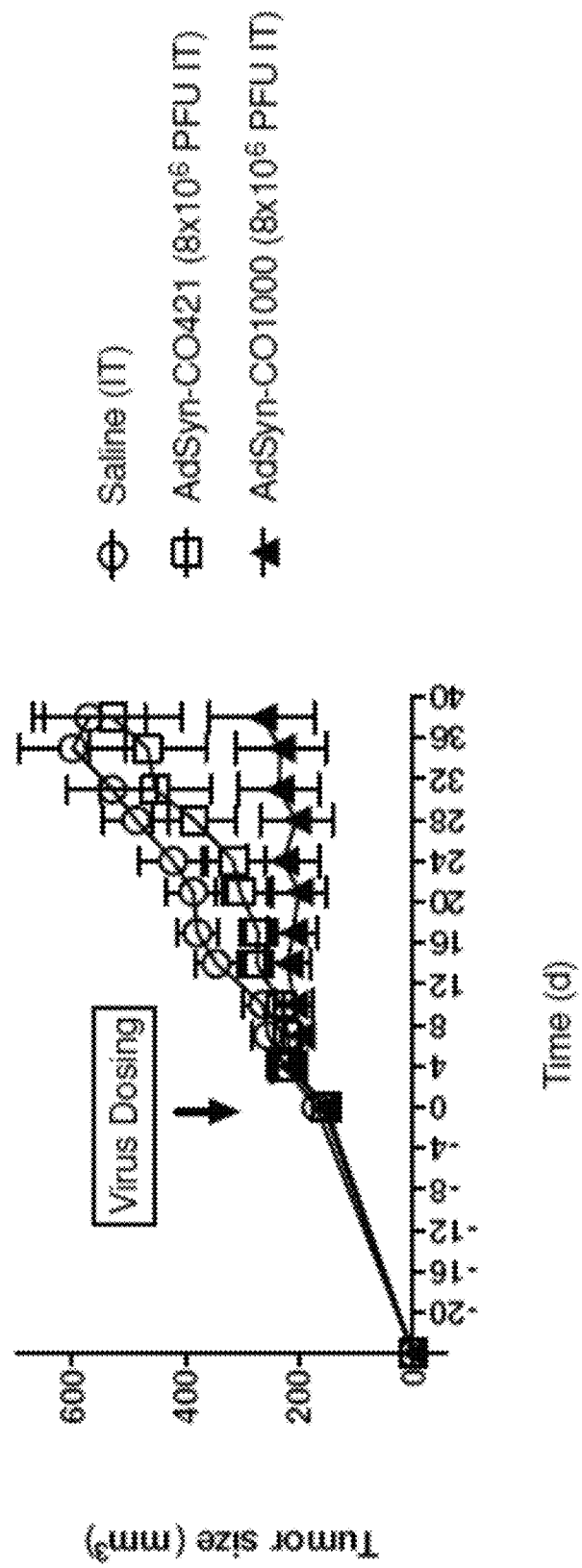
FIGS. 5A-5B are a pair of graphs showing in vivo efficacy of AdSyn-CO1000 and AdSyn-CO1042 in an A549 lung tumor xenograft model. Human A549 tumor cells were inoculated into nude mice by injecting $5 \times 10^6$ cells into the mammary fat pad. When tumors reached an average volume of ~164 mm$^3$ (day 0), mice were randomized into different treatment groups (n=8 mice per group). Mice were given a single intratumoral (IT) injection of PBS (saline) or a single injection of $8 \times 10^6$ PFU of the indicated viruses. AdSyn-CO421 encodes the YPet fluorophore as a YPet-P2A-ADP fusion, but is otherwise wild-type Ad5. AdSyn-CO1000 (FIG. 5A) and AdSyn-CO1042 (FIG. 5B) both exhibited enhanced anti-tumor activity as compared to the "wild type" AdSyn-CO421.
Figure 5B:
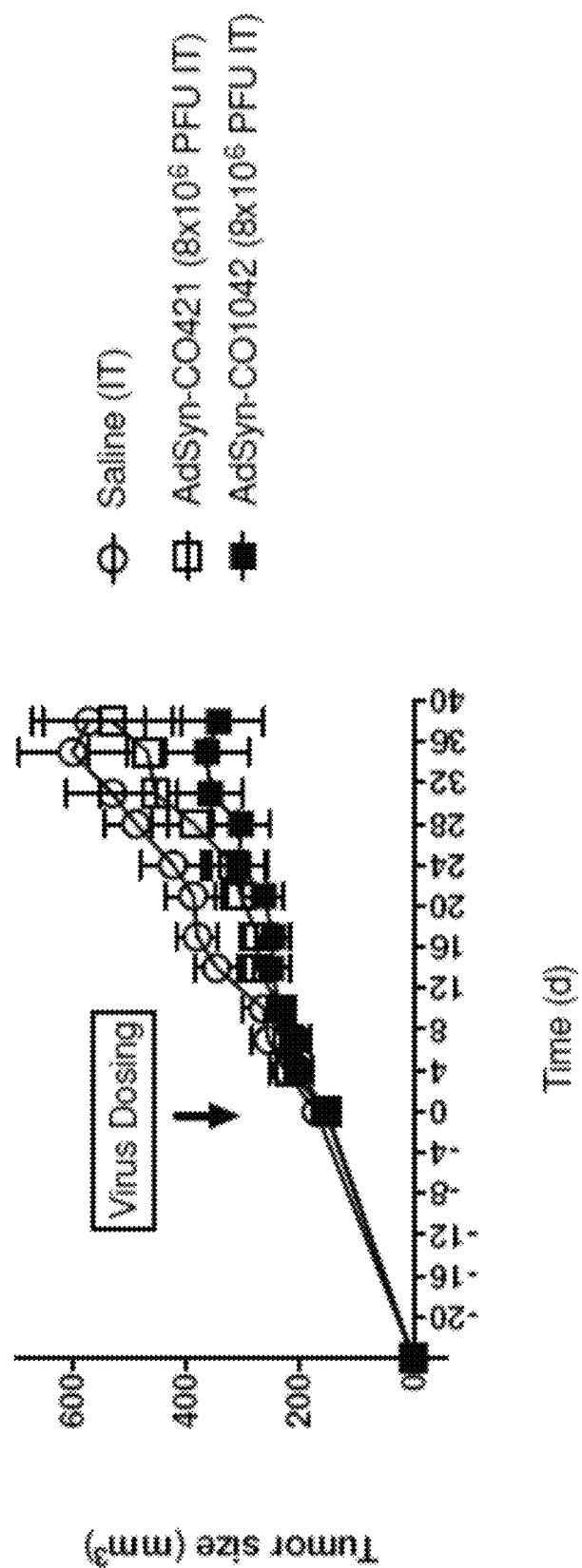

Both AdSyn-CO1000 and AdSyn-CO1042 are E3-deleted viruses that possess enhanced potency/replication in tumor cells as compared to WT Ad5, as demonstrated by the in vitro FBVK assay (see Tables 2A and 2B above). The in vivo efficacy of AdSyn-CO1000 and AdSyn-CO1042 was then tested in an A549 lung tumor xenograft model. Human A549 tumor cells were inoculated into nude mice by injecting $5 \times 10^6$ cells into the mammary fat pad. When tumors reached an average volume of ~164 mm³ (day 0), mice were randomized into different treatment groups (n=8 mice per group). Mice were given a single intratumoral (IT) injection of PBS or a single injection of $8 \times 10^6$ PFU of AdSyn-CO421, AdSyn-CO1000 or AdSyn-CO1042. AdSyn-CO421 encodes the YPet fluorophore as a YPet-P2A-ADP fusion, but is otherwise wild-type Ad5. AdSyn-CO1000 (FIG. 5A) and AdSyn-CO1042 (FIG. 5B) both exhibited enhanced anti-tumor activity as compared to the "wild type" AdSyn-CO421.

AdSyn-CO1042 was also tested in an HS578T orthotopic triple negative breast cancer tumor model. Human HS578T tumor cells were inoculated into 7 week old NSG mice by injecting $5 \times 10^6$ cells in 100 μl of HBSS into the right mammary fat pad. When tumors reached an average volume of ~168 mm³ (day 0), mice were randomized into different treatment groups (n=8 mice per group). Mice were given 3 doses of either PBS or AdSyn-CO1042 ($2 \times 10^8$ PFU) in a total volume of 50 µl on days 0, 7 and 14.

Figure 6:
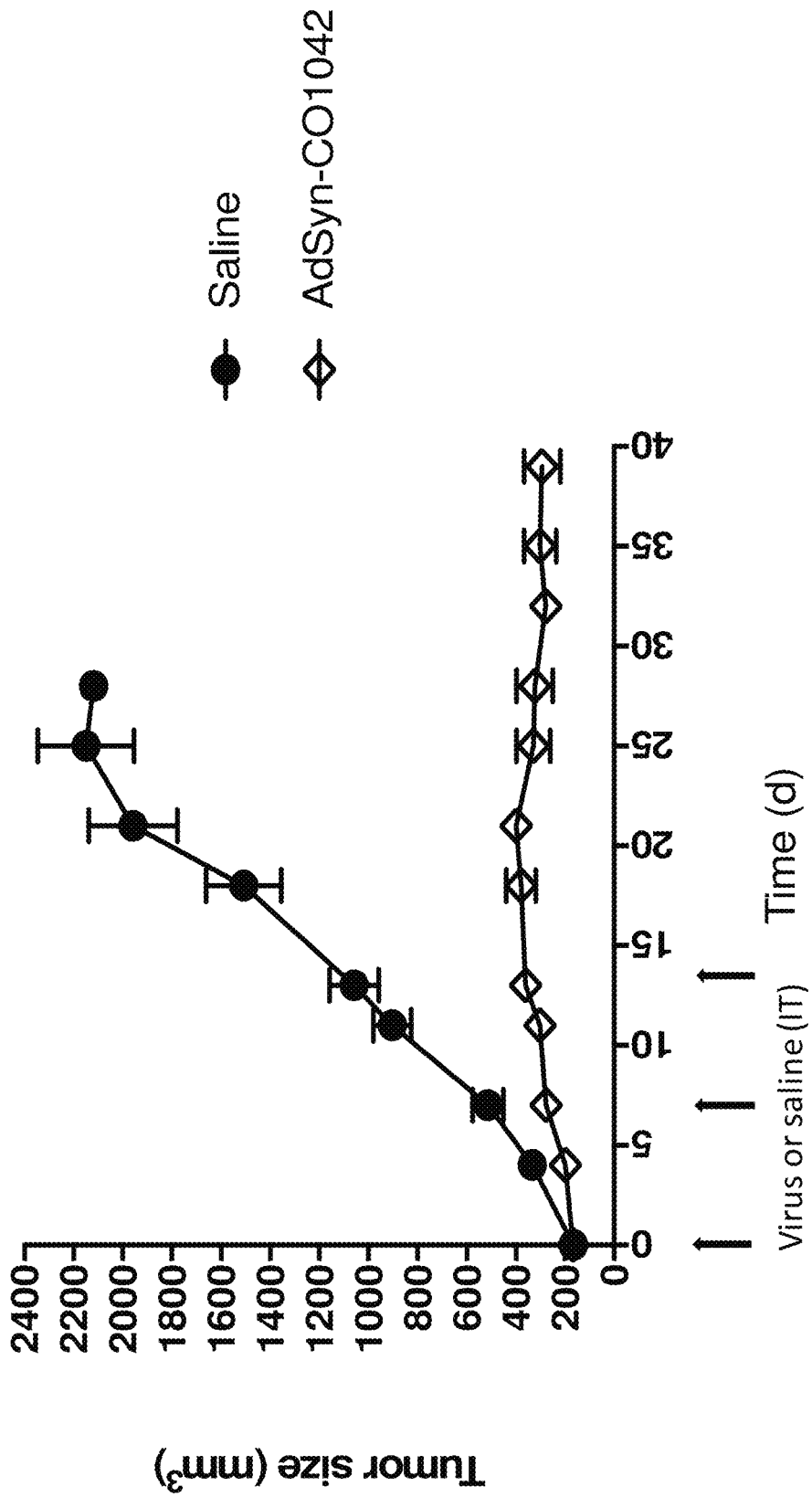
FIG. 6 is a graph showing in vivo efficacy of AdSyn-CO1042 in an orthotopic HS578T triple negative breast cancer model. Human HS578T tumor cells were inoculated into 7 week old NSG mice by injecting $5 \times 10^6$ cells in 100 µl of HBSS into the right mammary fat pad. When tumors reached an average volume of ~168 mm$^3$ (day 0), mice were randomized into different treatment groups (n=8 mice per group). Mice were given 3 doses of either PBS (saline) or AdSyn-CO1042 ($2 \times 10^8$ PFU) in a total volume of 50 µl on days 0, 7 and 14. All animals in the saline treatment group had to be sacrificed before day 30 due to tumor burden.

As shown in FIG. 6, tumor volume of AdSyn-CO1042 treated mice remained low over the 40-day study period. All animals in the PBS treatment group had to be sacrificed before day 30 due to tumor burden.

The studies described below indicate that the combination of tumor selectivity mutations (ΔLXCXE and ΔE4orf6/7) and the liver detargeting hexon mutation (E451Q) results in a better safety/toxicity profile for AdSyn-CO1042 and AdSyn-CO1000 as compared to WT Ad5, which is important in order to allow for the safe delivery of higher doses of these viruses intravenously (IV) for treatment of metastatic cancer. AdSyn-CO102, AdSyn-CO181, AdSyn-CO331 and AdSyn-CO1042 were administered intravenously to different groups of C57BL/6 mice (n=5 mice per group) in a volume of 200 µl on day 0 and again on day 7 at a dose of $8 \times 10^8$, $4 \times 10^9$ or $2 \times 10^{10}$. Mice were then analyzed for survival (FIG. 7A) and elevated liver enzymes (FIG. 7B) to assess liver toxicity.

Figure 7B:
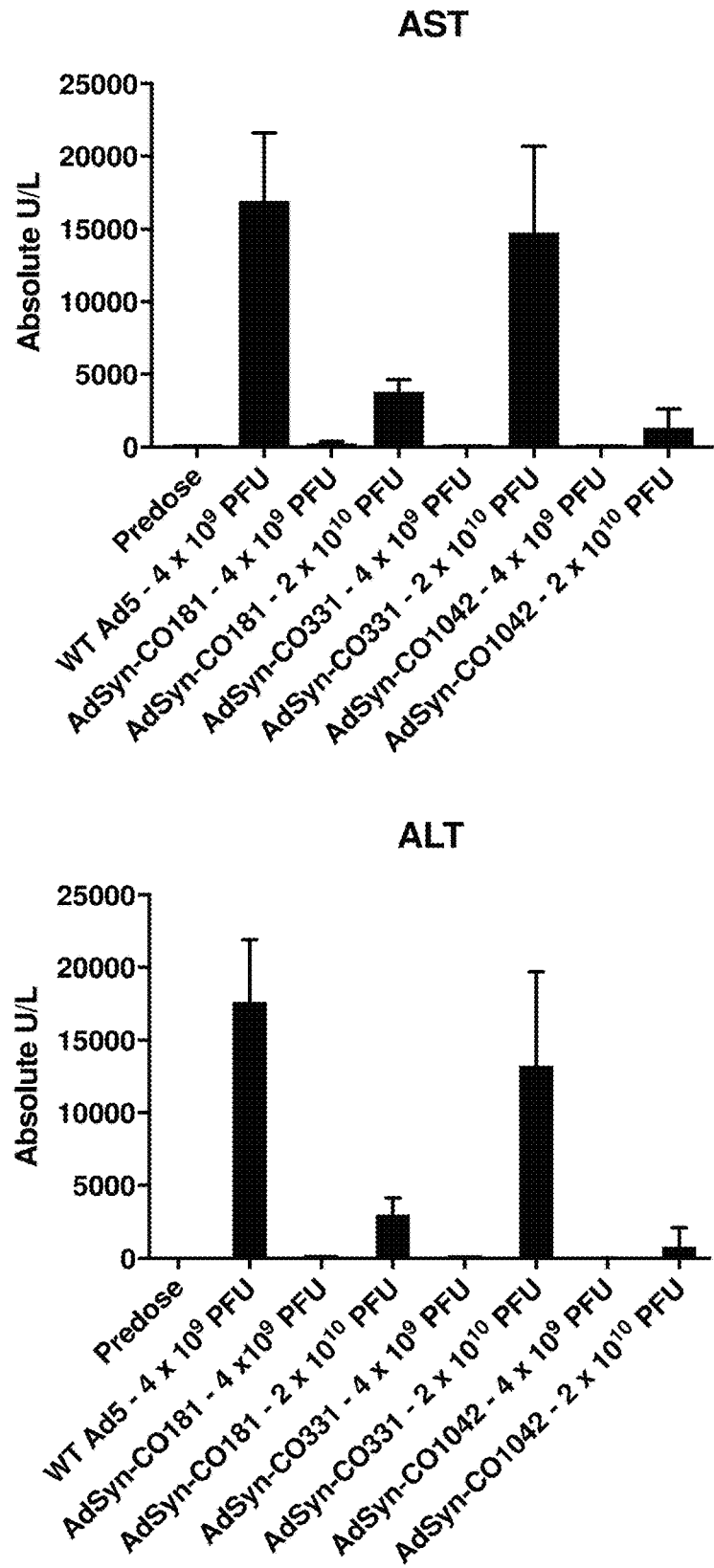

Mice were monitored for survival and gross signs of toxicity until day 14 (FIG. 7A). While WT Ad5 caused lethal toxicity at a dose of $4 \times 10^9$ PFU, both AdSyn-CO181 and AdSyn-CO331 were tolerated at this dose. AdSyn-CO1042 was tolerated at an even higher dose of $2 \times 10^{10}$ PFU. Blood samples were harvested from all mice on day −2 (pre-dose), day 2 (48 hours after dose 1) and day 9 (48 hours after dose 2) and frozen for subsequent analysis. Blood samples were assessed for the presence of various liver enzymes, such as alanine transaminase (ALT) and aspartate transaminase (AST). Results shown are the average AST and ALT levels from day 2 bleeds from the various treatment groups (FIG. 7B). The average pre-dose levels of AST and ALT from all mice are also shown. These data show that the ΔLXCXE and ΔE4orf6/7 mutations that restrict virus replication in normal cells (AdSyn-CO181) and the hexon de-targeting mutation present in AdSyn-CO331 both lead to reduced toxicity as compared to WT Ad5. AdSyn-CO1042 showed reduced liver toxicity even at a higher dose of $2 \times 10^{10}$ PFU, demonstrating that the combination of these different mutations present in AdSyn-CO1042 leads to a further reduction in toxicity.

Figure 8:
FIG. 8 is a table showing toxicity of AdSyn-CO1000 in BALB/c mice. Two different viruses were administered intravenously into different groups of mice (n=5 mice per group) in a volume of 200 µl on day 0, day 6 and day 12 at the indicated doses. Mice were then analyzed for survival to assess toxicity. Whereas WT Ad5 induced lethal toxicity in 2 of 5 mice at a dose of $0.8 \times 10^9$ PFU and killed all mice at a higher dose of 3.2×109 PFU, AdSyn-CO1000 was safer at slightly higher doses of $1 \times 10^9$ PFU and $4 \times 10^9$ PFU.
Figure 8:
Figure 8:

FIG. 8 is a table showing toxicity of AdSyn-CO1000 in BALB/c mice. Two different viruses were administered intravenously into different groups of mice (n=5 mice per group) in a volume of 200 µl on day 0, day 6 and day 12 at the doses listed in the figure. Mice were then analyzed for survival to assess toxicity. Whereas WT Ad5 induced lethal toxicity in 2 of 5 mice at a dose of $0.8 \times 10^9$ PFU and killed all mice at a higher dose of $3.2 \times 10^9$ PFU, AdSyn-CO1000 was safer at slightly higher doses of $1 \times 10^9$ PFU and $4 \times 10^9$ PFU. These data show that, despite its enhanced replication and killing potency in tumor cells, AdSyn-CO1000 demonstrates a better safety profile than WT Ad5 due to the tumor selectivity mutations and the liver de-targeting hexon mutation present in AdSyn-CO1000.

Figure 9:
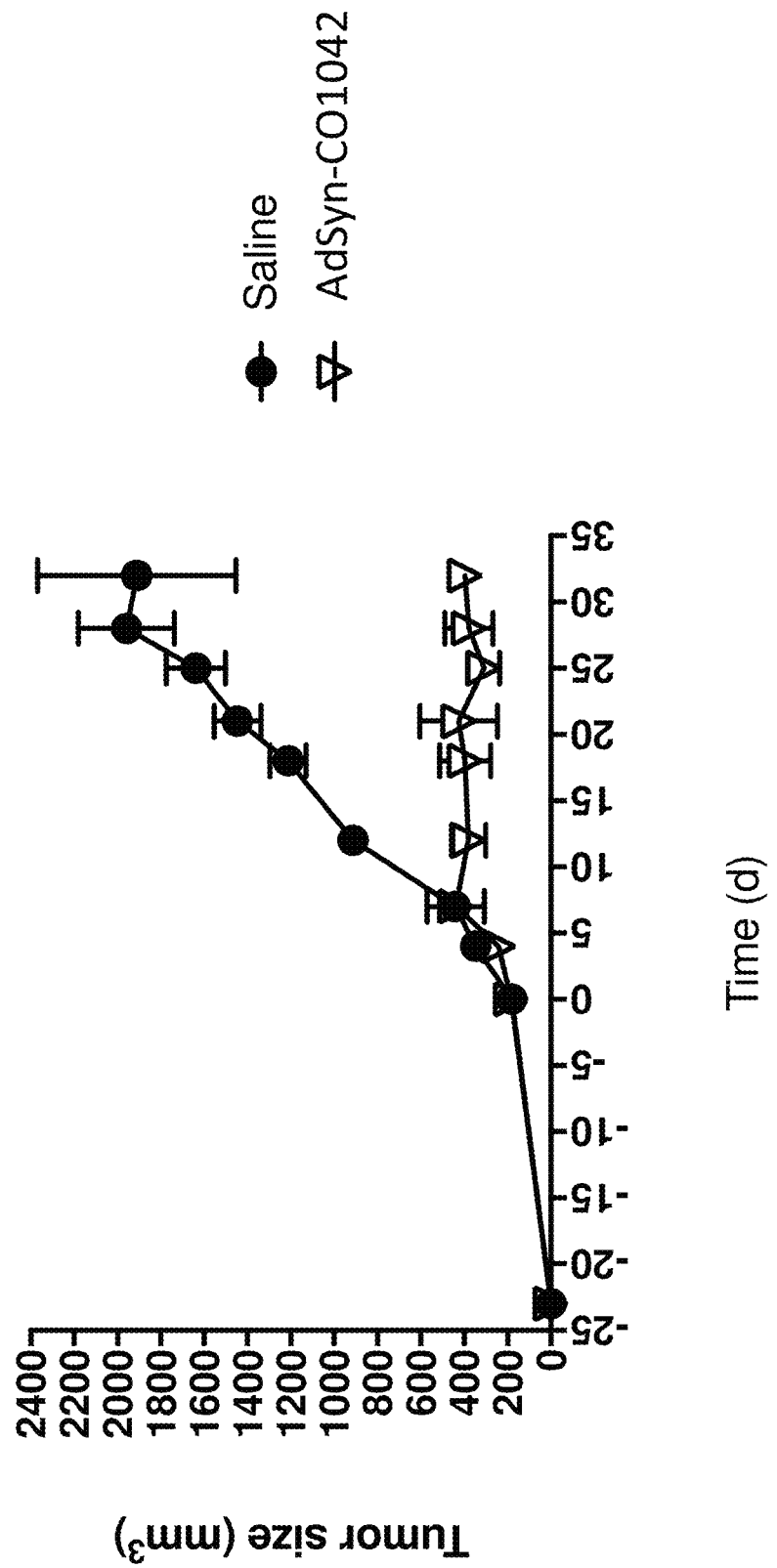
FIG. 9 is a graph showing in vivo efficacy of intravenously delivered AdSyn-CO1042 in an A549 lung tumor xenograft model. Human A549 tumor cells were inoculated into NSG mice by injecting $5 \times 10^6$ cells into the mammary fat pad. When tumors reached an average volume of ~184 mm$^3$ (day 0), mice were randomized into different treatment groups (n=8 mice per group). Mice were given a single injection of PBS (saline) or a single IV injection of $2 \times 10^9$ PFU of AdSyn-CO1042. All animals in the saline treatment group had to be sacrificed before day 33 due to tumor burden. Wild type Ad5 could not be delivered at the $2 \times 10^9$ PFU dose because this dose results in death.

Another study was performed in order to evaluate the efficacy of IV delivery of AdSyn-CO1042 in the A549 lung cancer xenograft model. Human A549 tumor cells were inoculated into NSG mice by injecting $5 \times 10^6$ cells into the mammary fat pad. When tumors reached an average volume of ~184 mm³ (day 0), mice were randomized into different treatment groups (n=8 mice per group). Mice were given a single injection of PBS or a single IV injection of $2 \times 10^9$ PFU of AdSyn-CO1042. As shown in FIG. 9, tumor volume remained low over the 33 day study period in animals treated AdSyn-CO1042. In contrast, all animals in the saline treatment group had to be sacrificed before day 33 due to tumor burden. Wild type Ad5 could not be delivered at the $2 \times 10^9$ PFU dose because this dose results in death.

Figure 10:
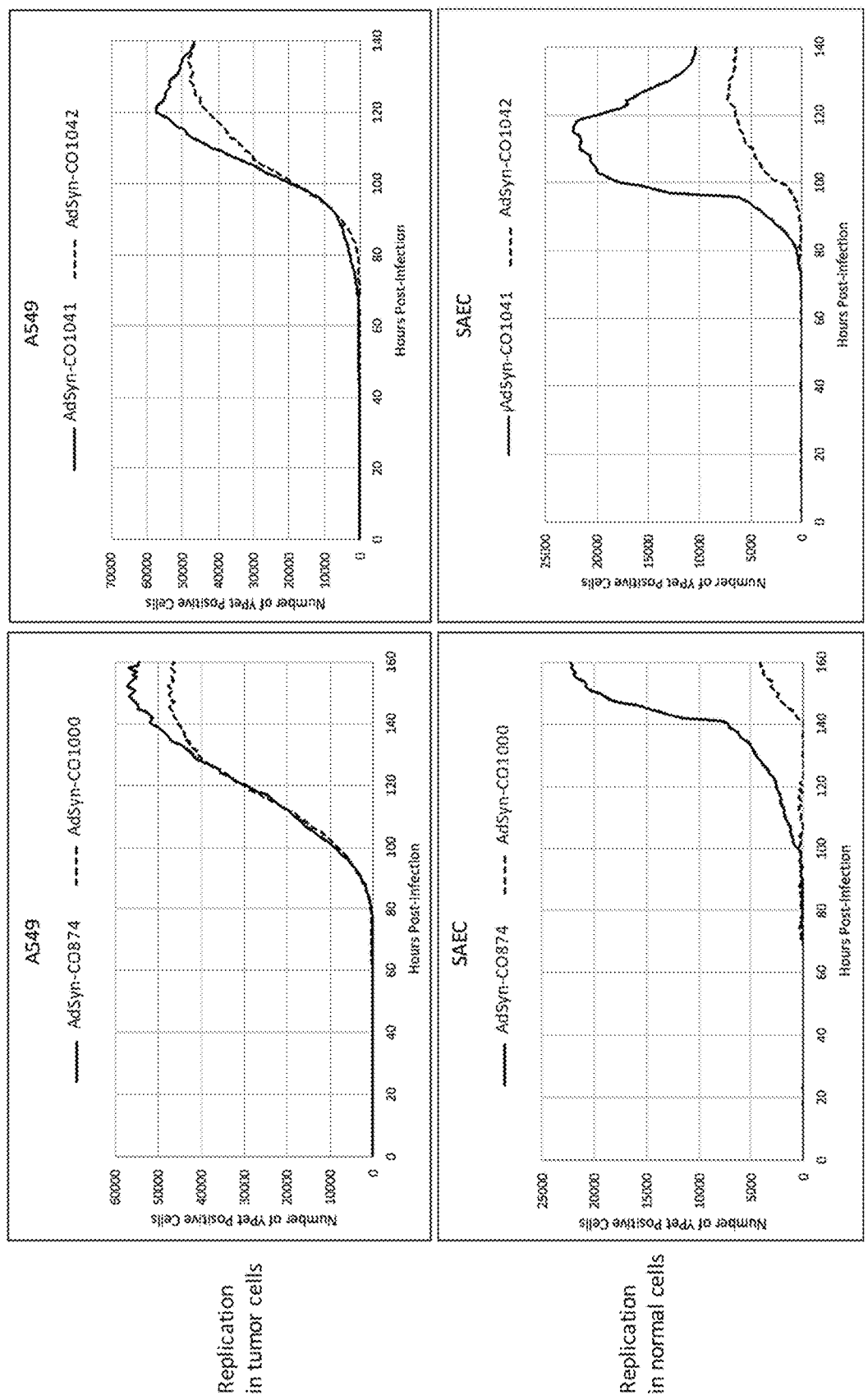
FIG. 10 is a set of graphs showing tumor-selective replication of AdSyn-CO1000 and AdSyn-CO1042. Human A549 cells (lung tumor) or human primary small airway epithelial cells (SAEC—normal lung) were infected at an MOI of 0.12 virus particles per cell with four different oncolytic viruses. All viruses encode the YPet fluorophore as a reporter to allow quantification of virus replication/expansion over time. Immediately after virus infection, virus infected cells were imaged once every hour in an IncuCyte ZOOM imaging system to quantify the number of YPet+ virus infected cells over a period of 6-7 days. Data are expressed as the number of YPet+ cells over time. AdSyn-CO874 and AdSyn-CO1000 are identical viruses except that AdSyn-CO1000 possesses the ΔLXCXE and ΔE4orf6/7 mutations that confer tumor-selective replication and the liver de-targeting hexon mutation. Similarly, AdSyn-CO1041 and AdSyn-CO1042 are identical viruses except that AdSyn-CO1042 possesses the ΔLXCXE and ΔE4orf6/7 mutations and the liver de-targeting hexon mutation. In tumor cells, AdSyn-CO1000 and AdSyn-CO1042 showed similar levels of virus expansion/replication as compared to AdSyn-CO874 and AdSyn-CO1041, respectively. However, in normal lung cells, AdSyn-CO1000 and AdSyn-CO1042 exhibited significantly attenuated expansion/replication as compared to AdSyn-CO874 and AdSyn-CO1041.

AdSyn-CO1000 and AdSyn-CO1042 were then evaluated in normal (non-tumor cells). Human A549 cells (lung tumor) or human primary small airway epithelial cells (SAEC—normal lung) were infected at an MOI of 0.12 virus particles per cell with one of four different oncolytic viruses (AdSyn-CO874, AdSyn-CO1000, AdSyn-CO1041 and AdSyn-CO1042). All viruses encode the YPet fluorophore as a reporter to allow quantification of virus replication/expansion over time. Immediately after virus infection, virus infected cells were imaged once every hour in an IncuCyte ZOOM imaging system to quantify the number of YPet+ virus infected cells over a period of 6-7 days. Data are expressed as the number of YPet+ cells over time. AdSyn-CO874 and AdSyn-CO1000 are identical viruses except that AdSyn-CO1000 possesses the ΔLXCXE and ΔE4orf6/7 mutations that confer tumor-selective replication and the liver de-targeting hexon mutation. Similarly, AdSyn-CO1041 and AdSyn-CO1042 are identical viruses except that AdSyn-CO1042 possesses the ΔLXCXE and ΔE4orf6/7 mutations and the liver detargeting hexon mutation. In tumor cells, AdSyn-CO1000 and AdSyn-CO1042 showed similar levels of virus expansion/replication as compared to AdSyn-CO874 and AdSyn-CO1041, respectively (FIG. 10). However, in normal lung cells, AdSyn-CO1000 and AdSyn-CO1042 exhibited significantly attenuated expansion/replication as compared to AdSyn-CO874 and AdSyn-CO1041. These data show that AdSyn-CO1000 and AdSyn-CO1042 demonstrate potent replication in tumor cells, but their replication is significantly attenuated in normal cells.

Example 5: Deletion or Modification of E3A, E3B and/or E4orf3

Figure 11:
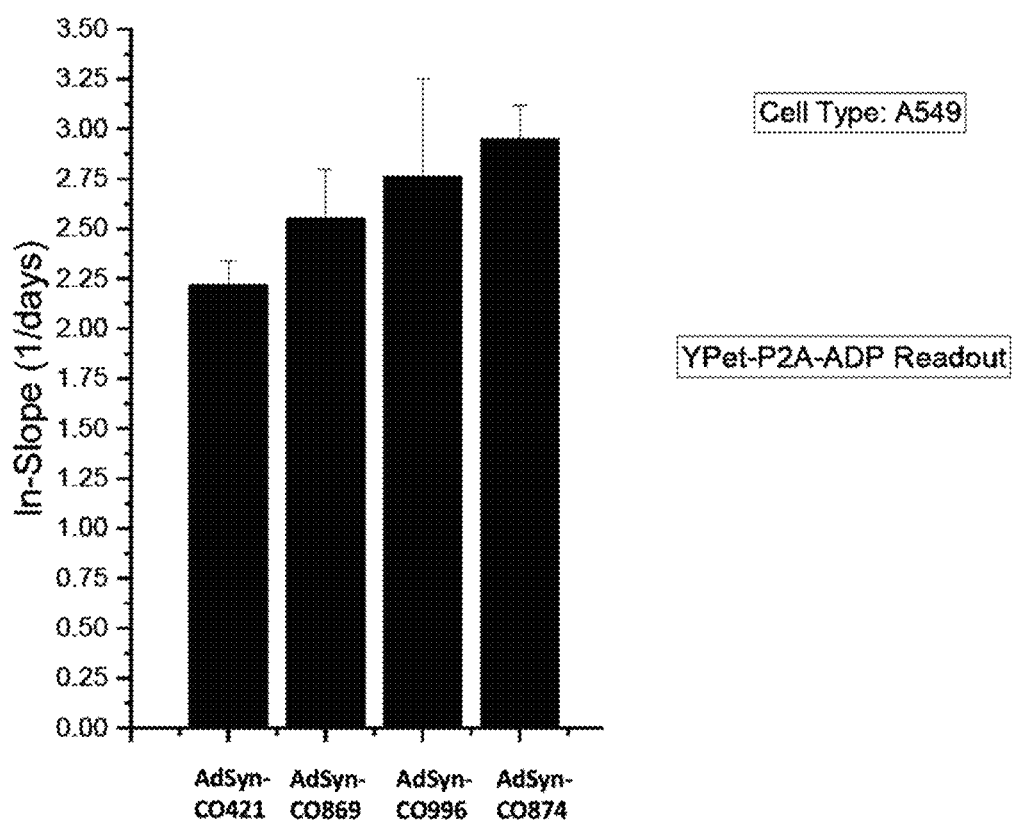
FIG. 11 is a bar graph demonstrating the impact of the deletion or abrogation of the E3B region on adenovirus replication. Four different recombinant viruses were assessed using a fluorescence-based viral kinetic (FBVK) assay to determine the rate of replication in human A549 lung tumor cells. The graph shows the In-slope values for each recombinant adenovirus encoding the Ypet fluorescent protein. In AdSyn-CO869, the RIDα, RIDβ and 14.7 k genes (E3B genes) have all been deleted from the genome. In AdSyn-CO996, expression of the RIDα, RIDβ and 14.7 k genes (E3B genes) has been abrogated either by mutating start codons or by mutating the genome to encode premature stop codons. In AdSyn-CO874, six E3 genes (12.5 k, 6.7 k, 19 k, RIDα, RIDβ, and 14.7 k) have been deleted from the genome.

Studies were conducted to evaluate the effect of abrogation of just the E3A genes or just the E3B genes on adenovirus replication kinetics. To evaluate the role of the E3B genes, AdSyn-CO421, AdSyn-CO869, AdSyn-CO996 and AdSyn-CO874 were assessed using a fluorescence-based viral kinetic (FBVK) assay to determine the rate of replication in human A549 lung tumor cells (FIG. 11). The data are reported as the ln-slope value for each recombinant adenovirus encoding the Ypet fluorescent protein. In AdSyn-CO869, the RIDα, RIDβ and 14.7 k genes (E3B genes) are deleted from the genome. In AdSyn-CO996, expression of the RIDα, RIDβ and 14.7 k genes (E3B genes) is abrogated either by mutating start codons or by mutating the genome to encode premature stop codons. As such, the genes are still present in the genome, but the genes are not expressed during viral infection. In AdSyn-CO874, six E3 genes (12.5 k, 6.7 k, 19 k, RIDα, RIDβ, and 14.7 k) are deleted from the genome. These data show that deletion or abrogation of expression of the RIDα, RIDβ and 14.7 k genes leads to an increase in virus replication. Deletion of additional E3 genes (12.5 k, 6.7 k, and 19 k) in AdSyn-CO874 leads to a further increase in replication kinetics.

Figure 12:
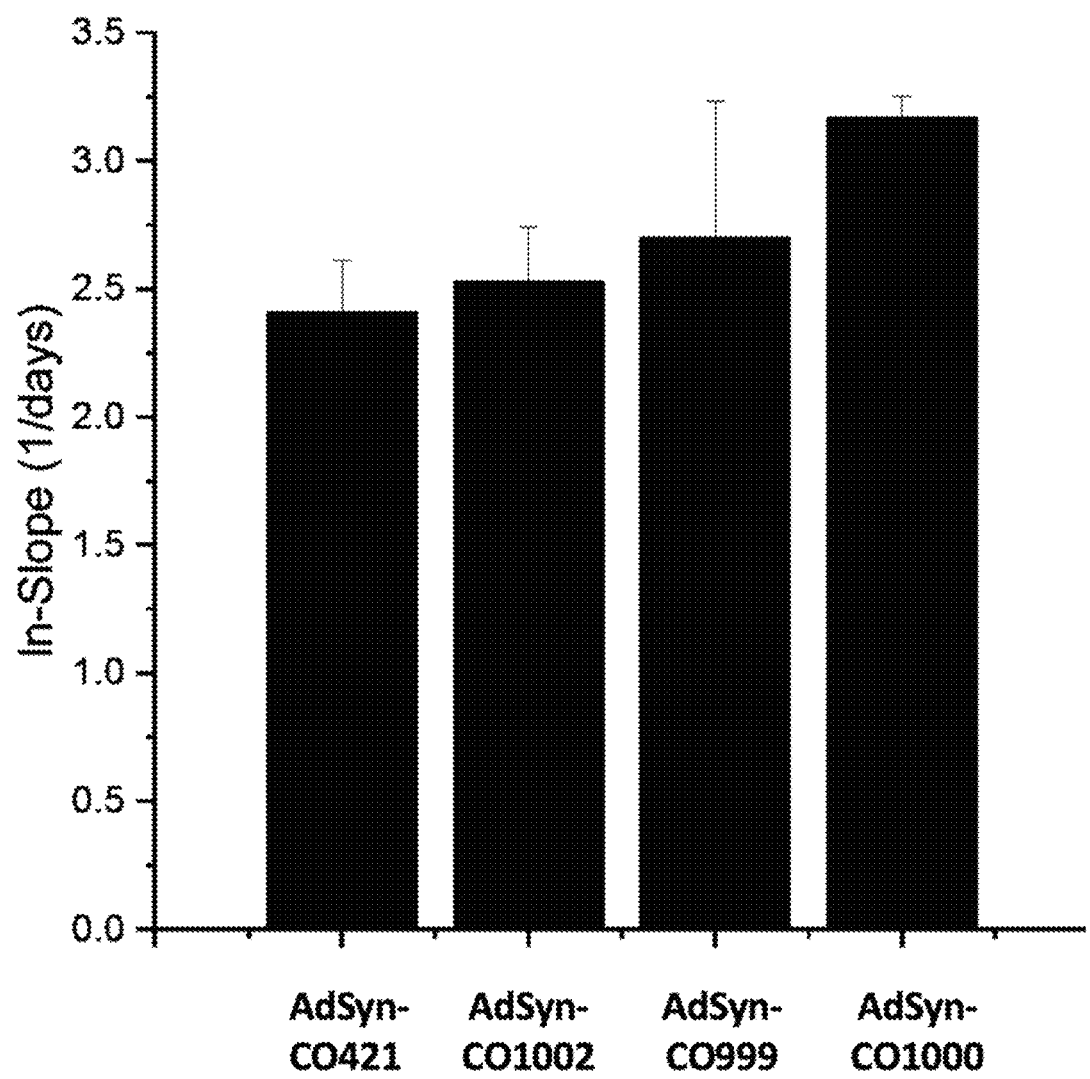
FIG. 12 is a bar graph showing the effect of deleting or abrogating the E3A region on adenovirus replication. Four different viruses were assessed in a FBVK assay to determine the rate of replication in human A549 lung tumor cells. The graph shows the In-slope values for each recombinant adenovirus encoding the Ypet fluorescent protein. In AdSyn-CO1002, the 12.5 k, 6.7 k and 19 k genes (E3A genes) have all been deleted from the genome. In AdSyn-CO999, the same E3A genes have been deleted, and this virus further includes the E1A ΔLXCXE, ΔE4orf6/7 and hexon [E451Q] modifications. In AdSyn-CO1000, the E3A and E3B genes (12.5 k, 6.7 k, 19 k, RIDα, RIDβ, and 14.7 k) have been deleted from the genome, and this virus further includes the E1A ΔLXCXE, ΔE4orf6/7 and hexon[E451Q] modifications.

To evaluate the role of the E3A genes, AdSyn-CO421, AdSyn-CO1002, AdSyn-CO999 and AdSyn-CO1000 were assessed in a FBVK assay to determine the rate of replication in human A549 lung tumor cells (FIG. 12). The data are reported as the ln-slope values for each recombinant adenovirus encoding the Ypet fluorescent protein. In AdSyn-CO1002, the 12.5 k, 6.7 k and 19 k genes (E3A genes) are deleted from the genome. In AdSyn-CO999, the same E3A genes are deleted, and this virus further includes the E1A ΔLXCXE, ΔE4orf6/7 and hexon[E451Q] modifications. In AdSyn-CO1000, the E3A and E3B genes (12.5 k, 6.7 k, 19 k, RIDα, RIDβ, and 14.7 k) are deleted from the genome, and this virus further includes the E1A ΔLXCXE, ΔE4orf6/7 and hexon[E451Q] modifications. These data show that deletion of the E3A genes leads to a modest increase in virus replication. Additional deletion of the E3B genes (RIDα, RIDβ and 14.7 k) in AdSyn-CO1000 leads to a further increase in replication kinetics.

Figure 13:
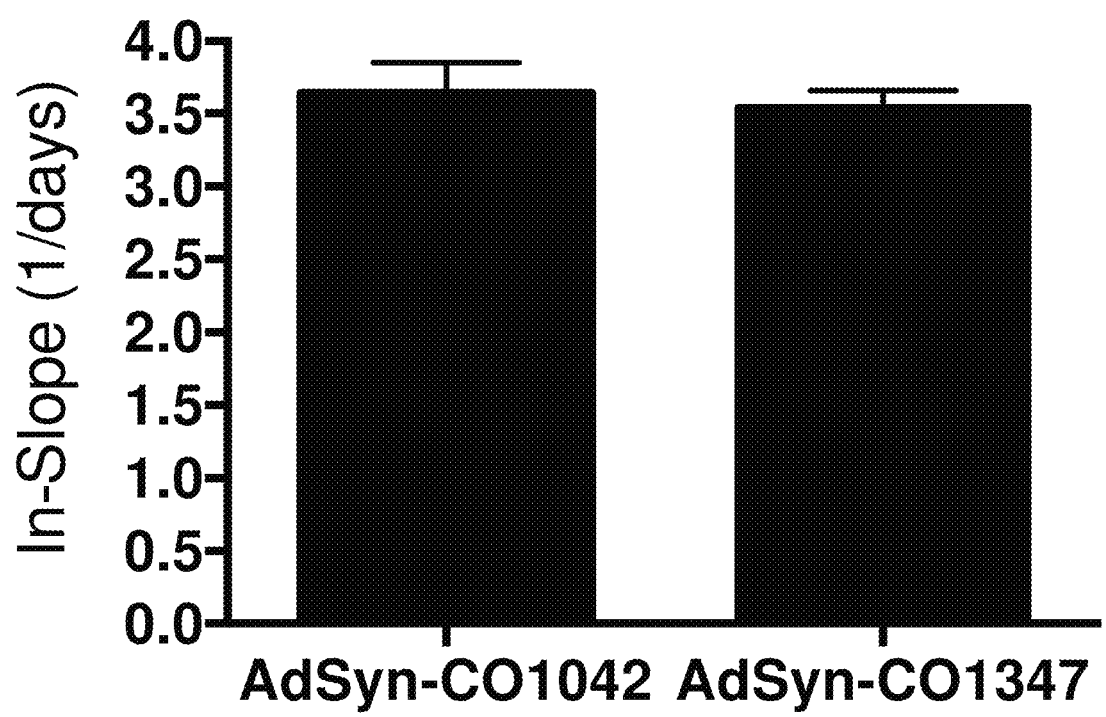
FIG. 13 is a bar graph showing that deletion of E4orf3 has no impact on virus replication. Two viruses were assessed in a FBVK assay to determine the rate of replication in A549 human lung tumor cells. The bar graph shows the In-slope values for each recombinant adenovirus. AdSyn-CO1042 and AdSyn-CO1347 are identical except for the deletion of E4orf3 in AdSyn-CO1347.

A further study was conducted to evaluate the effect of deletion of E4orf3 on virus replication kinetics. AdSyn-CO1042 and AdSyn-CO1347 were assessed in a FBVK assay to determine the rate of replication in A549 human lung tumor cells (FIG. 13). The graph shows the ln-slope values for each recombinant adenovirus. AdSyn-CO1042 and AdSyn-CO1347 are identical except for the deletion of E4orf3 in AdSyn-CO1347. These data demonstrate that E4orf3 can also be deleted in Ad5 without a negative impact on virus replication in tumor cells.

In view of the many possible embodiments to which the principles of the disclosure may be applied, it should be recognized that the illustrated embodiments are only examples of the disclosure and should not be taken as limiting the scope of the disclosure. Rather, the scope of the disclosure is defined by the following claims. We therefore claim as our invention all that comes within the scope and spirit of these claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12365878B2). An electronic copy of the sequence listing will also be available from the USPTO upon request and payment of the fee set forth in 37 CFR 1.19(b)(3).

The invention claimed is:

1. A recombinant adenovirus genome, comprising:
   an E1A region encoding a modified E1a protein;
   an E3 region encoding an adenovirus death protein (ADP) and comprising a modification or deletion of the coding sequences of each of E3 genes 12.5 k, 6.7 k, 19 k, RIDα, RIDβ and 14.7 k, wherein the modification prevents expression of each of the encoded proteins; and
   an E4 region comprising a modification or deletion of the E4orf6/7 coding sequence that prevents expression of the encoded protein, abolishes or impairs its E2F binding site, and/or deletes or impairs the nuclear localization signal.

2. The recombinant adenovirus genome of claim 1, wherein the modified E1a protein comprises:
   a deletion of the LXCXE motif;
   a deletion of residues 2-11;
   a C124G substitution;
   a Y47H substitution;
   a Y47H substitution and a C124G substitution; or
   a Y47H substitution, a C124G substitution and a deletion of residues 2-11,
   wherein the numbering of the preceding modifications is relative to SEQ ID NO: 23.

3. The recombinant adenovirus genome of claim 1, wherein the modification of the coding sequences of each of E3 genes 12.5 k, 6.7 k, 19 k, RIDα, RIDβ and 14.7 k, comprises a mutation of a start codon, a mutation that introduces a premature stop codon, or both.

4. The recombinant adenovirus genome of claim 1, further comprising a modification or deletion of E4orf3, wherein the modification prevents expression of the encoded protein.

5. The recombinant adenovirus genome of claim 1, comprising at least one modification to detarget an adenovirus from the liver.

6. The recombinant adenovirus genome of claim 5, comprising a mutation in the hexon protein.

7. The recombinant adenovirus genome of claim 6, wherein the hexon mutation is an E451Q mutation, wherein the numbering is relative to SEQ ID NO: 34.

8. The recombinant adenovirus genome of claim 1, wherein the genome encodes a chimeric fiber protein.

9. The recombinant adenovirus genome of claim 8, wherein the chimeric fiber protein comprises a fiber shaft from a first adenovirus serotype and a fiber knob from a second adenovirus serotype.

10. The recombinant adenovirus genome of claim 9, wherein the first adenovirus serotype of the chimeric fiber protein is Ad5 and the second adenovirus serotype is Ad3, Ad9, Ad11, Ad12, Ad34 or Ad37.

11. The recombinant adenovirus genome of claim 9, wherein the first adenovirus serotype of the chimeric fiber protein is Ad5 and the second adenovirus serotype is Ad34.

12. The recombinant adenovirus genome of claim 1, further comprising a heterologous open reading frame (ORF).

13. The recombinant adenovirus genome of claim 12, wherein the heterologous ORF is operably linked to and in the same reading frame as a self-cleaving peptide coding sequence and the ADP coding sequence, wherein the self-cleaving peptide coding sequence is disposed between the heterologous ORF and the ADP coding sequence.

14. The recombinant adenovirus genome of claim 13, wherein the self-cleaving peptide is a 2A peptide, or variant thereof.

15. The recombinant adenovirus genome of claim 14, wherein the 2A peptide comprises a porcine teschovirus-1 (PTV1) 2A (P2A) peptide, a foot and mouth disease virus (FMDV) 2A (F2A) peptide, an equine rhinitis A virus (ERAV) 2A (E2A) peptide or a Thosea asigna virus (TaV) 2A (T2A) peptide, or a variant thereof.

16. The recombinant adenovirus genome of claim 1, wherein the nucleotide sequence of the genome is at least 95% identical to SEQ ID NO: 3, SEQ ID NO: 5, SEQ ID NO: 7, SEQ ID NO: 8, SEQ ID NO: 9, SEQ ID NO: 10, SEQ ID NO: 13, SEQ ID NO: 14, SEQ ID NO: 47, SEQ ID NO:

48, SEQ ID NO: 49, SEQ ID NO: 50, SEQ ID NO: 51, SEQ ID NO: 52, SEQ ID NO: 53, SEQ ID NO: 54, or SEQ ID NO: 28.

17. A recombinant adenovirus comprising the recombinant adenovirus genome of claim 1.

18. A composition comprising the recombinant adenovirus of claim 17 and a pharmaceutically acceptable carrier.

19. The recombinant adenovirus genome of claim 1, wherein:
the modified E1a protein comprises a deletion of the LXCXE motif;
the genome comprises at least one modification in the hexon protein to detarget an adenovirus from the liver;
the genome comprises a heterologous ORF operably linked to and in the same reading frame as a self-cleaving peptide coding sequence and the ADP coding sequence; and
the genome encodes a chimeric fiber protein comprising a fiber shaft from a first adenovirus serotype and a fiber knob from a second adenovirus serotype.

20. The recombinant adenovirus genome of claim 19, wherein:
the modification or deletion of the coding sequences of each of the E3 genes 12.5 k, 6.7 k, 19 k, RIDα, RIDβ and 14.7 k, comprises deletion of each of the E3 genes 12.5 k, 6.7 k, 19 k, RIDα, RIDβ and 14.7 k;
the hexon modification is E451Q, wherein the numbering is relative to SEQ ID NO: 34;
the self-cleaving peptide is a 2A peptide;
the first adenovirus serotype of the chimeric fiber protein is Ad5 and the second adenovirus serotype is Ad3, Ad9, Ad11, Ad12, Ad34 or Ad37.

21. The recombinant adenovirus genome of claim 20, wherein the first adenovirus serotype of the chimeric fiber protein is Ad5 and the second adenovirus serotype is Ad34.

22. The recombinant adenovirus genome of claim 20, wherein the adenovirus is Ad5.

23. The recombinant adenovirus genome of claim 20, wherein the heterologous ORF is operably linked to and in the same reading frame as the self-cleaving peptide and the ADP coding sequence encodes YPet-P2A-ADP.

24. The recombinant adenovirus genome of claim 23, wherein the first adenovirus serotype of the chimeric fiber protein is Ad5 and the second adenovirus serotype is Ad34, and wherein the adenovirus is Ad5.

25. The recombinant adenovirus genome of claim 14, wherein the variant comprises a Gly-Ser-Gly at the N-terminus.

26. The recombinant adenovirus genome of claim 25, wherein the heterologous ORF encodes a fluorescent protein.

27. The recombinant adenovirus genome of claim 26, wherein the fluorescent protein is YPet.

28. The recombinant adenovirus genome of claim 1, wherein the nucleotide sequence of the genome comprises SEQ ID NO: 3, SEQ ID NO: 4, SEQ ID NO: 5, SEQ ID NO: 7, SEQ ID NO: 8, SEQ ID NO: 9, SEQ ID NO: 10, SEQ ID NO: 13, SEQ ID NO: 14, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, or SEQ ID NO: 59.

29. The recombinant adenovirus genome of claim 1, wherein the adenovirus genome comprises SEQ ID NO: 13.

30. The recombinant adenovirus genome of claim 1, wherein the adenovirus genome consists of SEQ ID NO: 13.

31. A recombinant adenovirus comprising the recombinant adenovirus genome of claim 24.

32. A recombinant adenovirus comprising the recombinant adenovirus genome of claim 29.

33. A recombinant adenovirus comprising the recombinant adenovirus genome of claim 30.

34. The recombinant adenovirus genome of claim 1, wherein the genome encodes a capsid-swapped adenovirus.

35. The recombinant adenovirus genome of claim 24, wherein the genome encodes a capsid-swapped adenovirus.

* * * * *